(12) United States Patent
Jaffrey et al.

(10) Patent No.: US 10,907,165 B2
(45) Date of Patent: Feb. 2, 2021

(54) METHODS OF ENHANCING TRANSLATION ABILITY AND STABILITY OF RNA MOLECULES, TREATMENTS, AND KITS

(71) Applicant: CORNELL UNIVERSITY, Ithaca, NY (US)

(72) Inventors: Sarnie R. Jaffrey, New York, NY (US); Jan Mauer, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 66 days.

(21) Appl. No.: 16/345,786

(22) PCT Filed: Oct. 31, 2017

(86) PCT No.: PCT/US2017/059265
§ 371 (c)(1),
(2) Date: Apr. 29, 2019

(87) PCT Pub. No.: WO2018/081788
PCT Pub. Date: May 3, 2018

(65) Prior Publication Data
US 2019/0264214 A1  Aug. 29, 2019

Related U.S. Application Data

(60) Provisional application No. 62/496,810, filed on Oct. 31, 2016.

(51) Int. Cl.
| | | |
|---|---|---|
| C12N 15/68 | (2006.01) | |
| C12N 15/85 | (2006.01) | |
| A61K 48/00 | (2006.01) | |
| C12P 19/34 | (2006.01) | |
| C12N 15/67 | (2006.01) | |

(52) U.S. Cl.
CPC .............. *C12N 15/68* (2013.01); *A61K 48/00* (2013.01); *C12N 15/67* (2013.01); *C12N 15/85* (2013.01); *C12P 19/34* (2013.01); *C12N 2710/16632* (2013.01); *C12N 2710/16641* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 8,278,036 | B2 | 10/2012 | Kariko et al. |
| 2006/0252115 | A1 | 11/2006 | Darzynkiewicz et al. |
| 2010/0129877 | A1 | 5/2010 | Sahin et al. |
| 2012/0046346 | A1 | 2/2012 | Rossi et al. |
| 2012/0156751 | A1 | 6/2012 | Kore et al. |
| 2016/0032316 | A1 | 2/2016 | Weissman et al. |
| 2018/0195077 | A1 | 7/2018 | Jaffrey et al. |

FOREIGN PATENT DOCUMENTS

| | | |
|---|---|---|
| EP | 2711008 A1 | 3/2014 |
| WO | 2017/011766 A1 | 1/2017 |

OTHER PUBLICATIONS

PCT International Search Report and Written Opinion for corresponding PCT/US2017/059265, dated Jan. 19, 2018.
Kariko et al., "Incorporation of Pseudouridine into mRNA Yields Superior Nonimmunogenic Vector with Increased Translational Capacity and Biological Stability," Mol. Ther. 16(11):1833-40 (2008).

*Primary Examiner* — Sean McGarry
(74) *Attorney, Agent, or Firm* — Troutman Pepper Hamilton Sanders LLP (Rochester)

(57) ABSTRACT

The present invention relates to methods of enhancing the translation ability and stability of an RNA molecule. The methods involve providing a cell-free composition comprising an RNA molecule to be translated, where the RNA molecule lacks an $N^6,2'O$-dimethyladenosine ("$m^6A_m$") residue. Also disclosed are methods of making RNA molecules and treatment methods using an RNA molecule comprising a 7-methylguanosine ("$m^7G$"), a 5' triphosphate linker ("-ppp-"), and an $N^6,2'$-O-dimethyladenosine ($m^6A_m$).

26 Claims, 16 Drawing Sheets
Specification includes a Sequence Listing.

SEQUENCE LISTING

```
<160> NUMBER OF SEQ ID NOS: 18

<210> SEQ ID NO 1
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: G at position 1 is N7-methylguanosine

<400> SEQUENCE: 1
gacacuugcu uuugacacaa cu                                               22

<210> SEQ ID NO 2
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: G at position 1 is N7-methylguanosine
<220> FEATURE:
<221> NAME/KEY: misc_feature
<222> LOCATION: (2)..(2)
<223> OTHER INFORMATION: A at position 2 is N6-methyladenosine

<400> SEQUENCE: 2
gacacuugcu uuugacacaa cu                                               22

<210> SEQ ID NO 3
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: G at position 1 is N7-methylguanosine
<220> FEATURE:
<221> NAME/KEY: misc_feature
<222> LOCATION: (2)..(2)
<223> OTHER INFORMATION: N at position 2 is 2'-O-dimethyladenosine

<400> SEQUENCE: 3
gncacuugcu uuugacacaa cu                                               22

<210> SEQ ID NO 4
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: G at position 1 is N7-methylguanosine
<220> FEATURE:
<221> NAME/KEY: misc_feature
<222> LOCATION: (2)..(2)
<223> OTHER INFORMATION: N at position 2 is N6,2'-O-dimethyladenosine

<400> SEQUENCE: 4
gncacuugcu uuugacacaa cu                                               22
```

```
<210> SEQ ID NO 5
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: G at position 1 is N7-methylguanosine
<220> FEATURE:
<221> NAME/KEY: misc_feature
<222> LOCATION: (4)..(4)
<223> OTHER INFORMATION: A at position 4 is N6-methyladenosine

<400> SEQUENCE: 5
gacacuugcu uuugacacaa cu                                              22

<210> SEQ ID NO 6
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: N at position 2 is N6,2'-O-dimethyladenosine

<400> SEQUENCE: 6
gncacuugcu uuugacacaa cu                                              22

<210> SEQ ID NO 7
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: A at position 6 is N6-methyladenosine

<400> SEQUENCE: 7
aguggacuaa ccaccaugga aggu                                            24

<210> SEQ ID NO 8
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: N at position 1 is N6,2'-O-dimethyladenosine

<400> SEQUENCE: 8
ncacuugcuu uugacacaac u                                               21

<210> SEQ ID NO 9
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: N at position 1 is N6,2'-O-dimethyladenosine
```

```
<400> SEQUENCE: 9
ncacuugcuu uugacacaac u                                              21

<210> SEQ ID NO 10
<211> LENGTH: 22
<212> TYPE: RNA
<213> ORGANISM: Artificial
<220> FEATURE:
<223> OTHER INFORMATION: Oligonucleotide

<400> SEQUENCE: 10
agcacuugcu uuugacacaa cu                                             22

<210> SEQ ID NO 11
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: A at position 1 is N6-methyladenosine

<400> SEQUENCE: 11
agcacuugcu uuugacacaa cu                                             22

<210> SEQ ID NO 12
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: N at position 1 is N6,2'-O-dimethyladenosine

<400> SEQUENCE: 12
ngcacuugcu uuugacacaa cu                                             22

<210> SEQ ID NO 13
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: N at position 1 is 2'-O-dimethyladenosine

<400> SEQUENCE: 13
ngcacuugcu uuugacacaa cu                                             22

<210> SEQ ID NO 14
<211> LENGTH: 20
<212> TYPE: RNA
<213> ORGANISM: Artificial
<220> FEATURE:
<223> OTHER INFORMATION: CRISPR guide RNA

<400> SEQUENCE: 14
uaucaaagac uauauuugua                                                20

<210> SEQ ID NO 15
<211> LENGTH: 20
```

```
<212> TYPE: RNA
<213> ORGANISM: Artificial
<220> FEATURE:
<223> OTHER INFORMATION: CRISPR guide RNA

<400> SEQUENCE: 15
aaccaguuuc uucaaagacc                                              20

<210> SEQ ID NO 16
<211> LENGTH: 21
<212> TYPE: DNA
<213> ORGANISM: Artificial
<220> FEATURE:
<223> OTHER INFORMATION: nLuc forward primer

<400> SEQUENCE: 16
atgtcgatct tcagcccatt t                                            21

<210> SEQ ID NO 17
<211> LENGTH: 20
<212> TYPE: DNA
<213> ORGANISM: Artificial
<220> FEATURE:
<223> OTHER INFORMATION: nLuc reverse primer

<400> SEQUENCE: 17
ggaggtgtgt ccagtttgtt                                              20

<210> SEQ ID NO 18
<211> LENGTH: 24
<212> TYPE: DNA
<213> ORGANISM: Artificial
<220> FEATURE:
<223> OTHER INFORMATION: nLuc cDNA probe

<400> SEQUENCE: 18
atccaaagga ttgtcctgag cggt                                         24
```

METHODS OF ENHANCING TRANSLATION ABILITY AND STABILITY OF RNA MOLECULES, TREATMENTS, AND KITS

This application is a national stage application under 35 U.S.C. § 371 of PCT International Application Serial No. PCT/US2017/059265, filed Oct. 31, 2017, which claims the priority benefit of U.S. Provisional Patent Application Ser. No. 62/496,810, filed, Oct. 31, 2016, which are hereby incorporated by reference in their entirety.

This invention was made with government support under 5R01CA186702-02 awarded by National Cancer Institute. The government has certain rights in the invention.

FIELD OF THE INVENTION

This invention relates to methods of enhancing the translation ability and stability of RNA molecules, treatments, and a kit.

BACKGROUND OF THE INVENTION

An emerging concept in gene expression regulation is that a diverse set of modified nucleotides is found internally within mRNA, and these modifications constitute an epitranscriptomic code. The initial concept of the epitranscriptome was introduced with the transcriptome-wide mapping of $N^6$-methyladenosine ("$m^6A$"), which revealed that $m^6A$ is found in at least a fourth of all mRNAs, typically near stop codons (Meyer et al., "Comprehensive Analysis of mRNA Methylation Reveals Enrichment in 3' UTRs and Near Stop Codons," *Cell* 149:1635-1646 (2012) and Dominissini et al., "Topology of the Human and Mouse m6A RNA Methylomes Revealed by m6A-Seq," *Nature* 485:201-206 (2012)). Notably, adenosine methylation to form $m^6A$ may be reversible. FTO and AlkB family member 5 ("ALKBH5") both show demethylation activity towards RNA containing $m^6A$ (Zheng et al., "ALKBH5 is a Mammalian RNA Demethylase that Impacts RNA Metabolism and Mouse Fertility," *Mol. Cell* 49:18-29 (2013) and Jia et al., "N6-Methyladenosine in Nuclear RNA is a Major Substrate of the Obesity-Associated FTO," *Nat. Chem. Biol.* 7:885-887 (2011)). Thus, the epitranscriptome may be highly dynamic and subject to reversible base modifications that influence mRNA function.

In addition to internal base modifications, the 5' end of mRNAs contains methyl modifications that are thought to be constitutive. mRNA biogenesis involves the addition of an $N^7$-methylguanosine ("$m^7G$") cap with a triphosphate linker to the 5' end of mRNAs. mRNAs are also methylated at the 2'-hydroxyl position of the ribose sugar of the first, and sometimes the second, nucleotide adjacent to the $m^7G$ cap (Adams et al., "Modifed Nucleosides and Bizarre 5'-Termini in Mouse Myeloma mRNA," *Nature* 255:28-33 (1975) and Wei et al., "Methylated Nucleotides Block 5' Terminus of HeLa Cell Messenger RNA," *Cell* 4:379-386 (1975)). These modifications recruit translation initiation factors to mRNA and allow the cell to discriminate host from viral mRNA (Dafs et al., "2'-O Methylation of the Viral mRNA Cap Evades Host Restriction by IFIT Family Members," *Nature* 468:452-456 (2010)).

Although the extended 5' cap structure contains these fixed methyl modifications, early studies showed that one additional methyl modification can be detected in up to 30% of mRNA caps (Wei et al., "N6, O2'-Dimethyladenosine a Novel Methylated Ribonucleoside Next to the 5' Terminal of Animal Cell and Virus mRNAs," *Nature* 257:251-253 (1975)). If the first nucleotide following the $m^7G$ cap is 2'-O-methyladenosine ("$A_m$"), it can be further methylated at the $N^6$-position by an unidentified nucleocytoplasmic methyltransferase to form $N^6$,2'-O-dimethyladenosine ("$m^6A_m$") (Wei et al., "N6, O2'-Dimethyladenosine a Novel Methylated Ribonucleoside Next to the 5' Terminal of Animal Cell and Virus mRNAs," *Nature* 257:251-253 (1975), which is hereby incorporated by reference in its entirety). Since 2'-O-methylation is essentially always detected at the first nucleotide, mRNAs can have either $A_m$ or $m^6A_m$ as the first nucleotide, but not A or $m^6A$ (Wei et al., "5'-Terminal and Internal Methylated Nucleotide Sequences in HeLa cell mRNA," *Biochemistry* 15:397-401 (1976)). The function of $m^6A_m$ is unknown.

The present invention is directed to overcoming deficiencies in the art.

SUMMARY OF THE INVENTION

One aspect of the present invention relates to a method of enhancing the translation ability and stability of an RNA molecule. This method involves providing a cell-free composition comprising an RNA molecule to be translated, where the RNA molecule lacks an $N^6$,2'-O-dimethyladenosine ($m^6A_m$) residue; introducing an $m^6A_m$ residue at the first 5' nucleotide of the RNA molecule; and adding an $m^7G$ nucleotide and triphosphate linker to the $m^6A_m$ residue to create a cap structure to enhance translation ability and stability of the RNA molecule relative to the RNA molecule lacking an $m^6A_m$ or a $m^7G$-ppp-$m^6A_m$ at the 5' end of the RNA molecule.

A further aspect of the present invention relates to a method of enhancing the translation ability and stability of an RNA molecule. This method involves providing a cell-free composition comprising an RNA molecule to be translated, where the RNA molecule lacks an $m^6A$ residue; introducing an $m^6A$ residue at the first 5' nucleotide of the RNA molecule; adding an $m^7G$ nucleotide and triphosphate linker to the $m^6A$ residue to create a cap structure; and methylating the $m^6A$ residue to form an $m^6A_m$ residue to enhance translation ability and stability of the RNA molecule relative to the RNA molecule lacking an $m^6A_m$ or a $m^7G$-ppp-$m^6A_m$ at the 5' end of the RNA molecule.

Another aspect of the present invention relates to a method of enhancing the translation and stability of an RNA molecule. This method involves providing an RNA molecule and adding to the RNA molecule a 5' cap structure comprising a 7-methylguanosine ($m^7G$), a 5' triphosphate linker ("-ppp-"), and an $N^6$,2'-O-dimethyladenosine ($m^6A_m$).

A further aspect of the present invention relates to a method of making an RNA molecule. This method involves providing an RNA molecule having a methylated adenosine ($m^6A$) residue at the first transcribed base of an mRNA molecule and capping the RNA molecule with a $m^7G$ cap under conditions effective to convert the $m^6A$ residue to an $N^6$,2'-O-dimethyladenosine ($m^6A_m$) residue to make an RNA molecule comprising an $m^6A_m$ residue at the first 5' nucleotide of the RNA molecule.

Another aspect of the present invention relates to a method of making an RNA molecule. This method involves transcribing an RNA molecule in the presence of a primer comprising a methylated adenosine ($m^6A$) residue at the 5' end of the primer in the presence of primer-dependent RNA polymerase and capping the RNA molecule with a $m^7G$ cap under conditions effective to convert the $m^6A$ residue to an $N^6$,2'-O-dimethyladenosine ($m^6A_m$) residue to make an RNA molecule comprising an m⁶A$_m$ residue in the first 5' nucleotide of the RNA molecule.

A further aspect of the present invention relates to a method of making an RNA molecule. This method involves transcribing an RNA molecule in the presence of a primer comprising an m⁷G cap followed by an N⁶,2'-O-dimethyladenosine (m⁶A$_m$) residue at the 5' end of the primer under conditions effective to make an RNA molecule comprising an m⁶A$_m$ residue in the first 5' nucleotide of the RNA molecule.

Another aspect of the present invention relates to a method of making an RNA molecule. This method involves providing a reaction solution comprising an mRNA molecule comprising a 5' m⁷G cap followed by an adenosine residue as the first 5' residue and enzymes capable of 2'-O-methylating and N⁶-methylating the adenosine residue to make an RNA molecule comprising an m⁶A$_m$ residue in the first 5' nucleotide of the RNA molecule.

A further aspect of the present invention relates to a method of making an RNA molecule. This method involves providing an RNA molecule comprising a 5' N⁶-methyladenosine (m⁶A) residue and adding to the RNA molecule a 5' m⁷G cap.

Another aspect of the present invention relates to a treatment method. This method involves contacting a cell with an RNA molecule comprising an N⁶,2'-O-dimethyladenosine (m⁶A$_m$) residue at the first 5' nucleotide of the RNA molecule under conditions effective to cause translation of the RNA molecule to treat the cell.

A further aspect, the invention relates to a treatment method that involves contacting a cell with a DNA molecule encoding an RNA molecule that will contain upon in-cell or in vivo transcription a 5' m⁷G cap and an N⁶,2'-O-dimethyladenosine (m⁶A$_m$) residue in the first encoded 5' nucleotide of the RNA molecule under conditions effective for the DNA molecule to be transcribed to produce an RNA molecule comprising an m⁶A$_m$ residue in the first 5' nucleotide of the RNA molecule such that the RNA molecule is translated to treat the cell.

Another aspect of the present invention relates to a method of synthesizing an RNA molecule. This method involves transcribing a DNA molecule in a cell-free composition to synthesize an RNA molecule comprising a cap structure at the 5' end of the RNA molecule, where the cap structure comprises an m⁷G or m⁷G-like residue, a phosphate linker, and an m⁶A$_m$ residue (m⁷G-(p)-m⁶A where p is a phosphate and n is an integer from 1-20), where the phosphate linker links the m⁷G or m⁷G-like residue to the m⁶A$_m$ residue.

As described herein, the extended mRNA cap carries dynamic and reversible epitranscriptomic information. In particular, m⁶A$_m$ in its physiological context adjacent to the m⁷G cap can be readily converted to A$_m$ by FTO in vitro and in vivo. Furthermore, m⁶A$_m$ and not m⁶A$_m$ is the preferred cellular substrate for FTO. m⁶A$_m$ transcripts were found to be markedly more stable than mRNAs beginning with A$_m$ or other nucleotides. Manipulation of m⁶A$_m$ levels by FTO depletion or FTO overexpression results in selective control of the abundance of m⁶A$_m$-containing mRNAs in cells. m⁶A$_m$ transcript stability is in part due to resistance to the mRNA-decapping enzyme DCP2. The significance of m⁶A$_m$-mediated mRNA stabilization can be seen by examining DCP2-dependent mRNA degradation processes in cells, such as the pattern of mRNA degradation induced by microRNAs. These findings show that the cap-associated modified nucleotide m⁶A$_m$ is a dynamic and reversible epitranscriptomic modification that confers stability to mRNA in mammalian cells.

BRIEF DESCRIPTION OF THE DRAWINGS

FIG. 1A is a graph showing a cumulative distribution plot of the translation efficiency for mRNAs that start with m⁶A$_m$, A$_m$, C$_m$, G$_m$, and U$_m$. The translation efficiency of mRNAs starting with an m⁶A$_m$ is significantly higher compared to mRNAs starting with A$_m$, C$_m$, G$_m$, or U$_m$ (n=3,024 (m⁶A$_m$); 921 (A$_m$); 1,788 (C$_m$); 1,351 (G$_m$); 2,008 (U$_m$); data represent the average from two independent previously published ribosome profiling data sets (Iwasaki et al., "Rocaglates Convert DEAD-Box Protein eIF4A Into a Sequence-Selective Translational Repressor," Nature 534: 558-561 (2016), which is hereby incorporated by reference in its entirety); each box shows the first quartile, median, and third quartile; whiskers represent 1.5× interquartile ranges; grey dots represent outliers; one-way ANOVA with Tukey's post hoc test, *P≤2.3×10⁻² versus m⁶A$_m$). mRNA translation efficiency is associated with the modification state of the first encoded nucleotide in HEK293 cells. FIG. 1B shows the correlation of translation efficiency replicates derived from HEK293T cells. The Pearson correlation coefficient (r) is shown. FIG. 1C is a graph showing the distribution of reads between the coding sequence ("CDS") and UTRs. High coverage in the CDS compared to UTRs verifies ribosome-derived footprints. FIG. 1D is a pair of bar graphs showing the total number of ribosome footprints near the start and stop codon of transcripts. FIG. 1E is a graph showing that three-nucleotide periodicity demonstrates ribosome-derived footprints. FIG. 1F is a bar graph showing the position of ribosome footprints relative to the reading frame.

FIG. 3B is a representative HPLC chromatogram of synthetic standards that were used to determine retention times of adenosine ("A"), 2'-O-methyladenosine ("A$_m$"), N$^6$-methyladenosine (m$^6$A), or N$^6$,2'-O-dimethyladenosine (m$^6$A$_m$). mAU, milli absorbance units. FIGS. 3C-3F are reaction curves for FTO with the different substrates that were used to calculate reaction velocity for Michaelis-Menten analysis. FTO concentrations that allowed initial velocity conditions were used for individual oligonucleotides (20 nM FTO for m$^7$Gpppm$^6$A$_m$ (FIG. 3C) and m$^7$Gpppm$^6$A (FIG. 3D): 200 nM FTO for m$^7$Gpppm$^6$A$_m$ (FIG. 3E) and internal m$^6$A (FIG. 3F) in a GGACU context; n 3 biological replicates; mean±s.e.m.). FIG. 3G is a Michaelis-Menten plot of FTO for either m$^6$A$_m$ or m$^6$A Michaelis-Menten curves of FTO reacting with m$^7$Gpppm$^6$A$_m$, m$^7$Gpppm$^6$A$_m$, m$^7$GpppACm$^6$A, or m$^6$A in a GGACU context. Owing to the increased reaction speed of FTO with m$^6$A$_m$ and m$^6$A adjacent to the m$^7$G compared to more distal m$^6$A$_m$ the enzyme concentration was tenfold. lower when we assessed reaction rates for m$^6$A$_m$ (20 nM FTO for the m$^7$Gpppm$^6$A$_m$ and m$^7$Gpppm$^6$A$_m$ oligonucleotide; 200 nM FTO for the m$^7$Gpppm$^6$A and for internal m$^6$A in a GGACU context). FIG. 4D, in contrast and discussed below, shows a plot in which the data. are normalized to enzyme concentration. However, here the plot shows data that were not normalized to enzyme concentration (n 3 biological replicates; mean s.e.m.).

FIGS. 4A-4D illustrate that FTO prefers m$^6$A$_m$ to m$^6$A as a substrate. FIG. 4A is a schematic illustration showing modifications of the extended mRNA cap. The first nucleotide (here shown as adenosine) adjacent to the m$^7$G and the 5'-to-5' triphosphate ("ppp") linker is subjected to 2'-O-methylation on the ribose, forming cap1. Cap1 can be further 2'-O-methylated at the second nucleotide to form cap2 (not depicted). 2'-O-methyladenosine ("A$_m$") can be further converted to cap1m by N$^6$-methylation, which results in N$^6$,2'-O-dimethyladenosine (m$^6$A$_m$). FIG. 4B is a pair of plots showing that FTO efficiently converts m$^6$A$_m$ to A$_m$. A synthetic oligonucleotide with a 5'-m$^7$Gpppm$^6$A$_m$ (2 µM) was incubated with FTO (100 nM FTO, 1 hour), which readily converted m$^6$A$_m$ to A$_m$ (representative high-performance liquid chromatography (HPLC) track of n=3 biological replicates). mAU, milli absorbance units. FIG. 4C is a pair of plots showing that FTO preferentially demethylates m$^6$A$_m$ compared to m$^6$A. An oligonucleotide with a 5'-m$^7$Gpppm$^6$A$_m$ cap was mixed in an equimolar ratio with an oligonucleotide containing internal m$^6$A. FTO (100 nM, 1 hour) almost completely converted m$^6$A$_m$ to A$_m$. Demethylation of m$^6$A was not detectable (representative HPLC track of n=3 biological replicates). FIG. 4D is a plot showing the Michaelis-Menten kinetics of FTO for m$^6$A$_m$ and m$^6$A. Owing to the increased activity of FTO with m$^6$A$_m$ compared to m$^6$A enzyme concentration was tenfold lower for m$^6$A$_m$ (20 nM FTO for m$^6$A$_m$, 200 nM FTO for m$^6$A). The data was normalized to enzyme concentration (m$^7$Gpppm$^6$A$_m$, m$^7$GpppACm$^6$A$_m$ internal m$^6$A; n=3 biological replicates; mean±s.e.m; V$_0$=initial reaction velocity).

FIG. 5A shows the structure-activity relationship of FTO and its substrate. ALKBH5 preferentially demethylates m$^6$A in its physiological sequence context but FTO does not require a sequence context to demethylate m$^6$A (Zheng et al., "ALKBH5 is a Mammalian RNA Demethylase That Impacts RNA Metabolism and Mouse Fertility," *Mol. Cell* 49:18-29 (2013) and Xu et al., "Structures of Human ALKBH5 Demethylase Reveal a Unique Binding Mode for Specific Single-Stranded N6-Methyladenosine RNA Demethylation," *J. Biol. Chem.* 289:17299-17311 (2014), which are hereby incorporated by reference in their entirety). This lack of a sequence preference suggests that m$^6$A is not a preferred substrate for FTO. Whether FTO preferentially demethylates m$^6$A$_m$ in its natural sequence context as the first nucleotide adjacent to the m$^7$G cap was next investigated. To determine the specific structural elements of the extended cap that are required for efficient N$^6$-demethylation of m$^6$A$_m$, oligonucleotides with different 5' ends were synthesized, as indicated in boxes 1-7. Shown is the amount of product (A$_m$ for substrates 1, 2, 4, 5; A for substrates 3, 6, 7) generated by FTO (200 nM) after 30 minutes when incubated with different oligonucleotides (20 µM) containing m$^6$A$_m$ or N$^6$-methyladenosine (m$^6$A). The highest FTO demethylation activity was on the full cap1m structure m$^7$Gpppm$^6$A$_m$ (1). Removal of the N$^7$-methyl from the guanosine (2) reduced FTO activity by 30% (2), whereas removal of either the 2'-O-methyl from the adenosine (3) or the m$^7$G (4) resulted in a 50% activity loss. FTO activity was further reduced by removal of m$^7$Gpp (5). The lowest FTO demethylation activity was observed when using m$^6$A as a substrate, either at the +3 position after the cap (6) or internally in a GGACU context (7). Thus, an adjacent m$^7$G cap does not activate m$^6$A as a substrate for FTO. These results indicate that FTO activity is dependent on the presence of a full cap structure, including the 2'-O-methyl at the +1 position, whereas m$^6$A is a poor substrate for FTO (one-way ANOVA with Tukey's post hoc test; *P0.001; n=3 biological replicates; mean±s.e.m.). FIG. 5B is a graph showing the structure-activity relationship of FTO and its substrate. Shown is the amount of substrate converted by FTO in a time-dependent manner at the same reaction conditions as in a (two-way ANOVA with Tukey's post hoc test; *P<0.001 versus all other structures; n=3 biological replicates; mean±s.e.m.). FIGS. 5C-5D are plots showing that FTO demethylates m$^7$Gpppm$^6$A$_m$ at the N$^6$-position through oxidization of m$^7$Gpppm$^6$A$_m$ to an N$^6$-hydroxymethyl intermediate ("m$^7$Gppphm$^6$A$_m$"). The final reaction product is m$^7$GpppA$_m$. Liquid chromatography/mass spectrometry analysis of m$^7$Gpppm$^6$A$_m$ RNA either left untreated (FIG. 5C; FTO) or after incubation with 3 µM FTO for 10 min (FIG. 5D; +FTO). Shown are representative mass-to-charge (m/z) ratios of precursor ions. In the absence of FTO, the dinucleotide shows a measured m/z ratio of 813.1173, 0.98 p.p.m. mass accuracy from the exact m/z of 813.1165 (formula C$_{23}$H$_{33}$N$_{10}$O$_{17}$P$_3$). Incubation with FTO generates m$^7$Gppphm$^6$A$_m$, shown as a measured m/z of 829.1123, 1.01 p.p.m. mass accuracy from the exact m$^7$Gppphm$^6$A$_m$ m/z of 829.1114 (formula C$_{23}$H$_{33}$N$_{10}$O$_{18}$P$_3$). The demethylated final product m$^7$GpppA$_m$ and residual non-demethylated m$^7$Gpppm$^6$A$_m$ were also detected in the FTO reaction mixture, with m$^7$GpppA$_m$ showing a measured m/z of 799.1064, 6.9 p.p.m. mass accuracy from the exact m/z of 799.1009 (formula C$_{22}$H$_{31}$N$_{10}$O$_{17}$P$_3$).

FIG. 6A is a schematic illustration showing modifications of the extended mRNA cap. The first nucleotide adjacent to the m$^7$G and the 5'-to-5'-triphosphate ("ppp") linker is subjected to 2'-O-methylation on the ribose, forming cap1. Cap1 can be further 2'-O-methylated at the second nucleotide to form cap2 (not depicted here). If cap1 contains a 2'-O-methyladenosine ("$A_m$"), it can be further converted to caplm by $N^6$-methylation, which results in $N^6$,2'-O-dimethyladenosine ($m^6A_m$). FIG. 6B are images showing the relative abundance of $m^6A$ in mRNA treated with recombinant FTO. Internal $m^6A$ residues that follow G in mRNA can be labelled and quantified in a 2D TLC method (Zhong et al., "MTA is an *Arabidopsis* Messenger RNA Adenosine Methylase and Interacts With a Homolog of a Sex-Specific Splicing Factor," Plant Cell 20:1278-1288 (2008), which is hereby incorporated by reference in its entirety). The relative abundance of $m^6A$ versus (A+C+U) in 400 ng mRNA that was either left untreated (−FTO) or incubated for 1 hour with 1 µM bacterially expressed recombinant human FTO (+FTO) was determined by 2D TLC. No decreases of $m^6A$ in FTO-treated mRNA was observed, indicating that FTO does not efficiently demethylate $m^6A$ in its physiological context in mRNA in vitro (representative images shown; n=3 biological replicates; mean±s.e.m.). FIG. 6C are images showing that FTO with a nuclear export signal is localized in the cytoplasm. Immunofluorescence staining of DDDDK/Flag tag in HEK293T cells transfected with Flag-tagged wild type FTO ("Flag-FTO") or Flag-tagged FTO with an N-terminal nuclear export signal ("NES-FTO"). FTO is primarily nuclear while NES-FTO is readily detected in the cytosol. DAPI was used to stain nuclei (representative images shown). FIG. 6D provides Western blot analyses performed to verify successful knockdown, overexpression, and knockout. Upper left, cell extracts from HEK293T cells with FTO knockdown were blotted with anti-FTO antibody. Knockdown efficiency was approximately 75%. The cell extracts were from the same samples used for RNA-seq analysis in FIG. 10D. GAPDH was used as loading control. Upper right, Western blot analysis of HEK293T expressing Flag vector (Ctrl) or FTO with an N-terminal nuclear export signal ("NES-FTO") that were used for RNA-seq half-life analysis in FIG. 10C. An antibody directed against β-actin was used as a loading control. The lower band represents endogenous FTO, whereas the upper band represents exogenous NES-FTO, which showed approximately tenfold overexpression. Upper left, cell extracts from ALKBH5-knockdown HEK293T cells were blotted with anti-ALKBH5 antibody. Knockdown efficiency was approximately 90%. The cell extracts were from the same samples used for RNA-seq analysis in FIG. 11E. β-Actin was used as loading control. Upper right, Western blot analysis of three different HEK293T clonal lines with CRISPR-mediated knockout of DCP2 that were used for RNA-seq analysis. GAPDH was used as loading control. FIG. 6E provides images and a graph showing that FTO expression decreases $m^6A_m$ in HEK293T cells. The relative abundance of modified adenosines in mRNA caps of HEK293T expressing Flag vector (Ctrl) or Flag-tagged FTO with an N-terminal nuclear export signal ("Flag-NES-FTO") was determined by 2D TLC. When determining the ratio of $m^6A_m$ to $A_m$, a significant decrease of $m^6A_m$ in Flag-NES-FTO-overexpressing cells was observed, indicating that FTO can convert cytoplasmic $m^6A_m$ to $A_m$ in vivo. Notably, the ratios of $m^6A_m/A_m$ that were observed upon FTO expression (both with and without the NES) may under-represent the true effect of FTO: $A_m$ mRNAs are generally less stable than $m^6A_m$ mRNAs owing to their degradation in cells via DCP2-mediated pathways (see FIGS. 10A-D and FIGS. 12A-D). Thus the $A_m$ mRNAs generated by FTO-mediated demethylation of $m^6A_m$ may not efficiently accumulate in cells compared to $m^6A_m$ mRNAs (representative images shown; n=3 biological replicates; mean±s.e.m.; unpaired Student's t-test, *P≤0.01). FIG. 6F contains images and a graph showing that FTO expression does not affect $m^6A$ in HEK293T cells. The relative abundance of $m^6A$ versus (A+C+U) in mRNA of HEK293T expressing empty vector (Ctrl) or FTO with an N-terminal nuclear export signal ("NES-FTO") was determined by 2D TLC. No decrease of $m^6A$ was observed upon NES-FTO expression, indicating that FTO does not readily influence levels of $m^6A$ in HEK293T cells at this level of expression. Notably, under these same expression conditions, $m^6A_m$ is readily demethylated (see FIG. 6E) (representative images shown; n=3 biological replicates; mean±s.e.m.). Control experiments measuring $m^6A$ and $m^6A_m$ levels following ALKBH5-knockdown and expression in HEK293T cells are shown in FIGS. 8A-D. FIG. 6G contains images and a graph showing that FTO deficiency increases $m^6A_m$ in vivo. Relative abundance of modified adenosines in mRNA caps of embryonic day ("E") 14 wild-type ("WT") littermate controls and Fto knockout ("Fto$^{-/-}$") mouse embryos (representative images shown; n=3 biological replicates; mean±s.e.m.; unpaired Student's t-test, P≤0.01). FIG. 6H contains images and graphs showing that FTO knockdown does not affect $m^6A$ in HEK293T cells. The relative abundance of $m^6A$ versus (A+C+U) in mRNA of HEK293T cells transfected with scrambled siRNA ("siCtrl") or siRNA directed against FTO ("siFTO") was determined by 2D TLC. No increase of $m^6A$ was observed upon FTO knockdown, indicating that FTO does not readily influence levels of $m^6A$ in vivo (representative images shown; n=3 biological replicates; mean±s.e.m.). FIG. 6I** contains images and a graph showing the relative abundance of $m^6A$ in Fto-knockout mouse embryos. The relative abundance of $m^6A$ versus (A+C+U) in mRNA of embryonic day 14 wild-type littermate controls and Fto-knockout ("Fto$^{-/-}$") mouse embryos was determined by 2D TLC. No increase of $m^6A$ was observed in Fto-deficient embryos, indicating that FTO does not influence the levels of $m^6A$ in this embryonic stage (representative images shown; n=3 biological replicates; mean±s.e.m.).

FIG. 7A is a pair of images and a graph showing that FTO readily demethylates $m^6A_m$ in mRNA. Relative abundance of modified adenosines in mRNA caps derived from mRNA treated with FTO (1 µM, 1 h; representative images shown; n=3 biological replicates; mean±s.e.m.; unpaired Student's t-test, P≤; 0.001). FIG. 7B** is a pair of images and a graph showing that FTO expression decreases $m^6A_m$ in HEK293T cells. Relative abundance of modified adenosines in mRNA caps of HEK293T cells expressing GFP ("Flag-GFP") or wild-type FTO ("Flag-FTO") (representative images shown; n=3 biological replicates; mean±s.e.m.; unpaired Student's t-test, *P≤0.05). FIG. 7C is a pair of images and a graph showing that FTO knockdown increases $m^6A_m$ in HEK293T cells. Relative abundance of modified adenosines in mRNA caps of HEK293T cells transfected with scrambled siRNA ("siCtrl") or siRNA directed against FTO ("siFTO") (representative images shown; n=3 biological replicates; mean±s.e.m.; unpaired Student's t-test, *P≤0.05).

FIG. 8A is a pair of images and a graph showing that ALKBH5 expression does not decrease $m^6A_m$ in HEK293T cells. The relative abundance of modified adenosines in mRNA caps of HEK293T cells expressing GST vector ("Ctrl") or ALKBH5 with an N-terminal GST tag ("GST-ALKBH5") was determined by 2D TLC. When determining the ratio of $m^6A_m$ to $A_m$, a significant decrease of $m^6A_m$ in ALKBH5-overexpressing cells was not observed, indicating that ALKBH5 does not convert m$^6$A$_m$ to A$_m$ in vivo (representative images show n; n=3 biologic al replicates; me an ±s.e.m.). FIG. 8B is a pair of images and a graph showing that ALKBH5 knockdown does not increase m$^6$A$_m$ in HEK293T cells. The relative abundance of modified adenosines in mRNA caps of HEK293T cells transfected with scrambled siRNA ("siCtrl") or siRNA directed against ALKBH5 ("siALKBH5") was determined by 2D TLC. When determining the ratio of m$^6$A$_m$ to A$_m$, a significant increase of m$^6$A$_m$ in ALKBH5-expressing cells was not observed, indicating that ALKBH5 does not convert m$^6$A$_m$ to A$_m$ in vivo (representative images shown; n=3 biological replicates; mean±s.e.m.). FIG. 8C is a pair of images and a graph showing that ALKBH5 knockdown increases m$^6$A in HEK293T cells. The relative abundance of m$^6$A versus (A+C+U) in mRNA of HEK293T cells transfected with scrambled siRNA ("siCtrl") or siRNA directed against ALKBH5 ("siALKBH5") was determined by 2D TLC. An approximately 30% increase of m$^6$A was observed upon ALKBH5 knockdown, indicating that ALKBH5 readily influences the levels of m$^6$A in vivo (representative images shown; n=3 biological replicates; mean±s.e.m.; unpaired Student's t-test, *P≤0.05). FIG. 8D is a pair of images and a graph showing that ALKBH5 expression decreases m$^6$A in HEK293T cells. The relative abundance of m$^6$A versus (A+C+U) in mRNA of HEK293T cells expressing GST vector ("Ctrl") or ALKBH5 with an N-terminal GST tag ("GST-ALKBH5") was determined by 2D TLC. A significant decrease of m$^6$A was observed upon ALKBH5 expression, indicating that SLKBH5 readily influences levels of m$^6$A in vivo (representative images shown; n=3 biological replicates; mean±s.e.m.; unpaired Student's t-test, **P≤0.01).

FIG. 9C is a pair of scatterplots related to FIGS. 10A and 10C and shows the correlation of half-life replicates derived from Flag-transfected (Ctrl, left scatter plot) or Flag-NES-FTO-transfected (NES-FTO, right scatter plot) HEK293T cells. The Pearson correlation coefficient (r) is shown for each comparison and indicates high correlation between replicates. FIG. 9D shows that mRNA stability is determined by the modification state of the first encoded nucleotide in HeLa cells. Cumulative distribution plot of the half-life for mRNAs that start with m$^6$A$_m$, A$_m$, C$_m$, G$_m$, and U$_m$. The half-life of mRNAs starting with an m$^6$A$_m$ is approximately 2.5 h longer compared to mRNAs starting with A$_m$, C$_m$, G$_m$, or U$_m$. Notably, for this analysis m$^6$A$_m$ mRNAs identified in HEK293T cells were used to analyze published half-life data sets from HeLa cells (Wang et al., "N6-Methyladenosine-Dependent Regulation of Messenger RNA Stability," Nature 505:117-120 (2014), which is hereby incorporated by reference in its entirety). This allowed the determination of whether the stabilizing effect of m$^6$A$_m$ on mRNA half-lives is conserved across different cell types. Indeed, the increase in m$^6$A$_m$ mRNA half-life compared to other starting nucleotides was similar to what was observed in FIG. 10A (n=2, 401 (m$^6$A$_m$); 645 (A$_m$); 1,310 (C$_m$); 988 (G$_m$); 1,533 (U$_m$); data represents the average from two independent data sets; each box shows the first quartile, median, and third quartile; whiskers represent 1.5× interquartile ranges; grey dots represent outliers; one-way ANOVA with Tukey's post hoc test, *P<2.2×10$^{-16}$ versus m$^6$A$_m$). FIG. 9E is a scatterplot related to FIG. 9D and FIG. 9G and shows the correlation of half-life replicates derived from published HeLa cell datasets (Wang et al., "N6-Methyladenosine-Dependent Regulation of Messenger RNA Stability," Nature 505:117-120 (2014), which is hereby incorporated by reference in its entirety). The Pearson correlation coefficient (r) is shown and indicates high correlation between replicates. FIG. 9F is a graph showing that stable mRNAs show enrichment of m$^6$A$_m$ miCLIP reads in HEK293T cells. miCLIP involves recovery of RNA fragments that interact with a m$^6$A-specific antibody, and thus recover m$^6$A- and m$^6$A$_m$-containing RNA fragments. The sequenced fragments, or miCLIP reads, map internally when they are m$^6$A. However, m6A$_m$ maps at the 5' ends of transcripts. To determine whether mRNAs with long half-life show m$^6$A$_m$ enrichment, metagene analysis of HEK293T cell-derived miCLIP tag distribution was performed in mRNAs that are in the top quartile of mRNA stability and the bottom quartile of mRNA stability. The miCLIP tag distribution of all mRNAs is shown as a grey dashed line. On all mRNAs, miCLIP reads were enriched around the stop codon, a pattern that reflects the typical distribution of m$^6$A in mRNA. Additional enrichment of miCLIP reads was seen in the 5' UTR, which were previously shown to primarily reflect m$^6$A$_m$ residues (Linder et al., "Single-Nucleotide-Resolution Mapping of m6A and m6Am Throughout the Transcriptome," Nat. Methods 12:767-772 (2015), which is hereby incorporated by reference in its entirety). However, when mRNAs with a long half-life (≥10 hours) were examined, a pronounced enrichment of miCLIP reads in the 5' UTR was observed. In contrast, mRNAs with a short half-life (≤3 hours) exhibit markedly fewer miCLIP reads in the 5' UTR. These data suggest that m$^6$A$_m$ is associated with increased mRNA stability (n=10,123 (all mRNAs); 820 (short half-life); 2,871 (long half-life)). FIG. 9G is a graph showing that stable mRNAs show enrichment of m$^6$A$_m$ miCLIP reads in HeLa cells. Similar to FIG. 9F, however, for this analysis miCLIP reads derived from HEK293T cells were used to analyze published half-life datasets from HeLa cells (Wang et al., "N6-Methyladenosine-Dependent Regulation of Messenger RNA Stability," Nature 505:117-120 (2014), which is hereby incorporated by reference in its entirety). A marked enrichment of miCLIP reads was seen in the 5' UTR of stable mRNAs, indicating elevated prevalence of m$^6$A$_m$ in these mRNAs. These data suggest that m$^6$A$_m$ is associated with increased mRNA stability, not only in HEK293T cells but also in HeLa cells. Importantly, the results are quantitatively similar to the results shown in FIG. 9F**, indicating that m$^6$A$_m$ mRNAs identified in HEK293T cells behave similarly in HeLa cells (n=18,286 (all mRNAs); 4,552 (short half-life); 3,619 (long half-life)).

FIG. 10A shows that mRNA stability is determined by the first encoded nucleotide in HEK293T cells. Cumulative distribution plot of the half-life for mRNAs that start with m$^6$A$_m$, A$_m$, C$_m$, G$_m$, and U$_m$ (n=2,515 (m$^6$A$_m$); 762 (A$_m$); 1,442 (C$_m$); 1,119

($G_m$); 1,486 ($U_m$); data represent the average from two independent datasets; each box shows the first quartile, median, and third quartile; whiskers represent 1.5× interquartile ranges; one-way ANOVA with Tukey's post hoc test, *$P \leq 2 \times 10^{-8}$ versus $m^6A_m$; $N_m=A_m$, $C_m$, $G_m$ or $U_m$). FIG. 10B shows that mRNA expression level is influenced by the modification state of the first encoded nucleotide in HEK293T cells. Cumulative distribution plot of the expression for mRNAs that start with $m^6A_m$, $A_m$, $C_m$, $G_m$, and $U_m$ (n=2,536 ($m^6A_m$); 1,063 ($A_m$); 2,098 ($C_m$); 1,577 ($G_m$); 2,071 ($U_m$); data represent the average from two independent datasets; each box shows the first quartile, median, and third quartile; whiskers represent 1.5× interquartile ranges; one-way ANOVA with Tukey's post hoc test, *$P \leq 2.2 \times 10^{-16}$ versus $m^6A_m$). FIG. 10C shows that FTO expression leads to a global decrease of $m^6A_m$ mRNA half-life in HEK293T cells. Changes in half-life of mRNAs containing either $m^6A_m$ or $A_m$ in cells transfected with either Flag vector (Ctrl) or FTO with an N-terminal nuclear export signal (NES-FTO) (n=2,049 ($m^6A_m$); 951 ($A_m$); 1,442 ($C_m$); 1,119 ($G_m$); 1,486 ($U_m$); data represent the average from two independent datasets; each box shows the first quartile, median, and third quartile; whiskers represent 1.5× interquartile ranges; one-way ANOVA with Tukey's post hoc test, $P \leq 4.6 \times 10^{-3}$ versus $m^6A_m$). FIG. 10D shows that FTO knockdown leads to a global increase of $m^6A_m$ mRNAs in HEK293T cells. Expression of mRNAs containing either $m^6A_m$ or $A_m$ upon FTO knockdown (n=3,410 ($m^6A_m$); 1,355 ($A_m$); 2,636 ($C_m$); 1,994 ($G_m$); 2,558 ($U_m$); data represent the average from two independent mRNA expression datasets; each box shows the first quartile, median, and third quartile; whiskers represent 1.5× interquartile ranges; one-way ANOVA with Tukey's post hoc test $P \leq 7.4 \times^{-3}$ $m^6A_m$ versus $A_m$ and $U_m$).

FIG. 11A is a graph showing that $m^6A_m$ mRNAs exhibit increased half-life compared to $A_m$ mRNAs in vivo. HEK293T cells were electroporated with in vitro-synthesized mRNAs starting with either of two extended caps: $m^7$Gppp $A_m$ or $m^7$Gpppm$^6A_m$. Next, cellular poly(A) RNA was isolated and the in vivo half-life of the electroporated $A_m$- and $m^6A_m$-containing mRNA was determined by qRT-PCR. In control siRNA-treated HEK293T cells ("siCtrl"), the $m^6A_m$ mRNA showed a trend towards increased half-life compared to the $A_m$ mRNA (unpaired Student's t-test, P=0.08). Notably, when the same experiment was performed in FTO siRNA-treated cells ("siFTO") to prevent demethylation of $m^6A_m$, the $m^6A_m$ mRNA half-life was significantly increased (n=3 biological replicates; mean±s.e.m.; unpaired Student's t-test, P≤0.05). FIG. 11B is a graph showing that NES-FTO expression preferentially affects the half-life of $m^6A_m$ mRNAs compared to $m^6A$ mRNAs. Changes in half-life of mRNAs containing either $m^6A_m$ or $m^6A$ in HEK293T cells transfected with either Flag vector ("Ctrl") or FTO with an N-terminal nuclear export signal ("NES-FTO") were determined by RNA-seq. $m^6A_m$ mRNAs are generally long-lived (see FIG. 10A) and show reduced half-lives after NES-FTO expression. Whether FTO could elicit a similar effect on mRNAs containing $m^6A$ was next investigated. For this experiment, a set of mRNAs with annotated $m^6A$ residues was used (Linder et al., "Single-Nucleotide-Resolution Mapping of m6A and m6Am Throughout the Transcriptome," *Nat. Methods* 12:767-772 (2015), which is hereby incorporated by reference in its entirety), excluding those which also contain an annotated $m^6A_m$. NES-FTO expression reduced the half-life of $m^6A_m$ mRNAs but did not have any substantial effect on the half-life of $m^6A$ mRNAs. These data support the idea that FTO preferentially targets $m^6A_m$ compared to $m^6A$ (n=2,049 ($m^6A_m$); 2,495 ($m^6A$); data represent the average from two independent datasets; each box shows the first quartile, median, and third quartile; whiskers represent 1.5× interquartile ranges; grey dots represent outliers; one-way ANOVA with Tukey's post hoc test, ***$P \leq 2.2 \times 10^{-16}$ versus $m^6A$). FIG. 11C is a graph showing that NES-FTO expression preferentially affects the half-life of $m^6A_m$ mRNAs compared to $A_m$ mRNAs. Changes in half-life of $A_m$ mRNAs (FUCA1, PCK1, SCFD2) and $m^6A_m$ mRNAs (PCNA, PSMD3, MAGOHB) in HEK293T cells transfected with either Flag vector ("Ctrl") or FTO with an N-terminal nuclear export signal ("NES-FTO") were determined by BrU pulse-chase analysis and subsequent qRT-PCR. $m^6A_m$ mRNAs show a significant reduction in half-life after NES-FTO expression whereas the half-life of $A_m$ mRNAs is less affected. These data examine specific mRNAs in contrast to the whole-transcriptome analysis presented in FIG. 10C and also demonstrate the stabilization effect of $m^6A_m$ using a different method to measure mRNA half-life (that is, BrU pulse-chase labelling) other than transcriptional inhibition (n=3 biological replicates; mean±s.e.m.; unpaired Student's t-test, *P≤0.05, P≤0.01). FIG. 11D is a graph showing the expression of mRNAs containing either $m^6A_m$ or $A_m$ upon Fto knockout as determined by RNA-seq. FTO depletion ("Fto$^{-/-}$") results in increased abundance of mRNAs with an annotated $m^6A_m$ residue in liver tissue derived from Fto-knockout mice. Fold change was measured relative to the RNA levels measured in the same tissue obtained from wild-type littermates (n=2,048 ($m^6A_m$); 1,025 ($A_m$); 2,081 ($C_m$); 1,742 ($G_m$); 1,242 ($U_m$); data represent the average from two independent data sets; each box shows the first quartile, median, and third quartile; whiskers represent 1.5× interquartile ranges; grey dots represent outliers; one-way ANOVA with Tukey's post hoc test, *$P \leq 7.5 \times 10^{-6}$ $m^6A_m$ versus $A_m$ and $U_m$). FIG. 11E is a graph showing that knockdown of ALKBH5 does not increase the levels of $m^6A_m$ mRNAs. The expression of mRNAs containing either $m^6A_m$ or $A_m$ upon ALKBH5 knockdown in HEK293T cells was determined by RNA-seq. In contrast to knockdown or knockout of FTO, $m^6A_m$ mRNAs are slightly less abundant than $A_m$ mRNAs in ALKBH5-knockdown cells. This suggests that ALKBH5 does not target $m^6A_m$-containing mRNAs in vivo (n=3,111 ($m^6A_m$); 1,928 ($A_m$); 4,382 ($C_m$); 3,110 ($G_m$); 3,998 ($U_m$); data represent the average from two independent datasets; each box shows the first quartile, median, and third quartile; whiskers represent 1.5× interquartile ranges; grey dots represent outliers; one-way ANOVA with Tukey's post hoc test, **$P \leq 1.2 \times 10^{-3}$ $m^6A_m$ versus $A_m$ and $U_m$).

FIG. 12A is a schematic representation of the DCP2 in vitro decapping assay. The 5' end of oligonucleotides containing the indicated form of adenosine (A, $A_m$, $m^6A_m$ or $m^6A_m$) was enzymatically capped with [$\alpha$-$^{32}$P]-$m^7$GTP. DCP2 causes the release of [$\alpha$-$^{32}$P]-$m^7$GDP, which is detected by TLC. FIG. 12B is an image and a graph showing that $N^6$-methylation of the cap-adjacent adenosine inhibits mRNA decapping in vitro. The presence of a 2'-O-methyl did not affect DCP2 activity relative to adenosine. However, addition of an $N^6$-methyl group decreased decapping efficiency (n=3 biological replicates; mean±s.e.m.; two-way ANOVA with Tukey's post hoc test, P≤0.01). FIG. 12C is a graph showing that DCP2 deficiency primarily increases expression of non-$m^6A_m$ mRNAs in the HEK293T cell transcriptome. Cumulative distribution plot of the expression of mRNAs that start with $m^6A_m$, $A_m$, $C_m$, $G_m$, and $U_m$ (n=3,287 ($m^6A_m$); 2,350 ($A_m$); 3,963 ($C_m$); 3,540 ($G_m$); 3,496 ($U_m$); data represent the average from two independent datasets; each box shows the first quartile, median, and third quartile; whiskers represent 1.5× interquartile ranges; one-way ANOVA with Tukey's post hoc test, $P \leq 2.2 \times 10^{-16}$ versus $m^6A_m$). FIG. 12D is a graph showing that $m^6A_m$ reduces mRNA susceptibility to microRNA-mediated degradation. Cumulative distribution plot of the expression of mRNAs that start with $m^6A_m$, $A_m$, $C_m$, $G_m$, or $U_m$ (n=2,090 ($m^6A_m$); 623 ($A_m$); 1,109 ($C_m$); 852 ($G_m$); 1,322 ($U_m$); data represent the average from two independent datasets; each box shows the first quartile, median, and third quartile; whiskers represent 1.5× interquartile ranges; one-way ANOVA with Tukey's post hoc test, **$P \leq 2.2 \times 10^{16}$ versus $m^6A_m$).

FIG. 13A is an image showing that DCP2 decapping products are $m^7GDP$. These results confirm the identity of the putative $m^7GDP$ decapping product in the decapping assay by treatment with nucleoside-diphosphate kinase ("NDPK"). The shift to the $m^7GTP$ position confirms that the released product is $m^7GDP$. A cap-labelled RNA with a guanosine as the first nucleotide was used as a positive control (lanes 3, 6, 9; the 'p' denotes the position of the $^{32}P$). FIG. 13B is a graph showing Michaelis-Menten curves of 10 nM DCP2 reacting with $m^7Gpppm^6A_m$ or $m^7GpppA_m$ for 30 minutes at 37° C. DCP2 shows higher decapping activity towards $m^7GpppA_m$ than to $m^7Gpppm^6A_m$ (the dashed lines indicate the $K_m$ on the x axis; n=3 biological replicates; mean±s.e.m.). FIG. 13C is a graph showing that DCP2 depletion preferentially stabilizes $A_m$ mRNAs compared to $m^6A_m$ mRNAs. Changes in half-life of $A_m$ mRNAs (FUCA1, PCK1, SCFD2) and $m^6A_m$ mRNAs (PCNA, PSMD3, MAGOHB) in HEK293T cells transfected with either Flag vector ("Ctrl") or DCP2-knockout cells ("DCP2$^{-/-}$") were determined by BrU pulse-chase analysis and subsequent qRT-PCR. $A_m$ mRNAs show a significant increase in half-life after DCP2 depletion whereas the half-life of $m^6A_m$ mRNAs was not significantly increased. These data are related to the whole-transcriptome expression analysis presented in FIG. 12C and indicate that, in addition to the observed abundance changes of non-$m^6A_m$ mRNAs versus $m^6A_m$ mRNAs, DCP2 also selectively affects the half-life of specifically examined mRNAs (n=3 biological replicates; mean±s.e.m.; unpaired Student's t-test, *$P \leq 0.05$, $P \leq 0.01$). In FIG. 12D, it was found that $m^6A_m$ mRNAs show less upregulation upon DICER knockdown than mRNAs beginning with other nucleotides. This concept was further examined using additional independent datasets of gene expression following depletion of proteins required for microRNA-mediated mRNA degradation, such as members of the Argonaute protein family. Measurement of mRNA expression in AGO2-knockdown HEK293T cells ("siAGO2") compared to control cells ("siCtrl") (Schmitter et al., "Effects of Dicer and Argonaute Down-Regulation on mRNA Levels in Human HEK293 Cells," Nucleic Acids Res. 34:4801-4815 (2006), which is hereby incorporated by reference in its entirety) revealed more pronounced upregulation of non-$m^6A_m$ mRNAs compared to those that have $m^6A_m$ (n=2,080 ($m^6A_m$); 596 ($A_m$); 1,085 ($C_m$); 805 ($G_m$); 1,274 ($U_m$); data represent the average from two independent datasets; each box shows the first quartile, median, and third quartile; whiskers represent 1.5× interquartile ranges; grey dots represent outliers; one-way ANOVA with Tukey's post hoc test, *$P \leq 1 \times 10^4$ $m^6A_m$ versus $A_m$, $C_m$ and $U_m$). FIG. 13E is similar to FIG. 12D, but only looks at the expression changes of mRNAs that contain TargetScan-predicted microRNA-binding sites. Applying this filter criteria, it was observed that DICER knockdown in HEK293T cells (siDICER) (Schmitter et al., "Effects of Dicer and Argonaute Down-Regulation on mRNA Levels in Human HEK293 Cells," Nucleic Acids Res. 34:4801-4815 (2006), which is hereby incorporated by reference in its entirety) resulted in more pronounced upregulation of non-$m^6A_m$ miRNA target mRNAs compared to those that have $m^6A_m$ (n=1,208 ($m^6A_m$); 359 ($A_m$); 607 ($C_m$); 467 ($G_m$); 713 ($U_m$); data represent the average from two independent datasets; each box shows the first quartile, median, and third quartile; whiskers represent 1.5× interquartile ranges; grey dots represent outliers; one-way ANOVA with Tukey's post hoc test, ***$P \leq 9.6 \times 10^4$ versus $m^6A_mN_m$, where $N_m=A_m$, $C_m$, $G_m$ or $U_m$). FIG. 13F is a graph related to FIG. 12D and FIG. 13E, which show that $m^6A_m$ mRNAs exhibit less upregulation upon DICER knockdown than mRNAs beginning with other nucleotides. To examine this concept further using additional filtering criteria, whether $m^6A_m$ mRNA resistance to DICER depletion is dependent on the number of microRNA-binding sites was investigated. To this end, mRNAs were divided into five groups: mRNAs that do not contain a predicted microRNA-binding site (0) and mRNAs that belong to specific quartiles that were assigned depending on the number of microRNA-binding sites (low (1) to high (4)). Notably, no expression differences were observed between $m^6A_m$ mRNAs and non-$m^6A_m$ mRNAs that do not carry predicted microRNA-binding sites. However, there was a clear increase in mRNA expression for mRNAs that contain microRNA-binding sites, and this increase was dependent on the number of microRNA-binding sites. Notably, for each quartile, $m^6A_m$ mRNAs were significantly less upregulated than $N_m$ mRNAs (n=91 versus 89 ($m^6A_m$ versus $N_m$; 1); 252 versus 339 ($m^6A_m$ versus $N_m$; 1); 311 versus 454 ($m^6A_m$ versus $N_m$; 2); 247 versus 541 ($m^6A_m$ versus $N_m$; 3); 229 versus 512 ($m^6A_m$ versus $N_m$; 4); data represent the average from two independent datasets; number of microRNA-binding sites in each quartile: 1=1-3; 2=4-6; 3=7-12; 4=13-54; each box shows the first quartile, median, and third quartile; whiskers represent 1.5× interquartile ranges; one-way ANOVA with Tukey's post hoc test, *$P \leq 0.05$, *$P \leq 0.001$, n.s., not significant). FIG. 13G is a graph related to FIG. 12D and FIGS. 2D-2F, which show that $m^6A_m$ mRNAs are largely resistant to expression changes upon global inhibition of the microRNA machinery. Whether introduction of a single microRNA also leads to differential responses of $m^6A_m$ mRNAs compared to non-$m^6A_m$ mRNAs was next investigated using a published dataset where HeLa cells were transfected with a miR-155 duplex to achieve microRNA-specific mRNA degradation (Guo et al., "Mammalian MicroRNAs Predominantly Act to Decrease Target mRNA Levels," Nature 466:835-840 (2010), which is hereby incorporated by reference in its entirety). For this analysis, $m^6A_m$ mRNAs mapped in HEK293T cells were used. It was first whether a differential effect of mRNA degradation on miR-155 target (Yang et al., "StarBase: A Database for Exploring MicroRNA-mRNA Interaction Maps from Argonaute CLIP-Seq and Degradome-Seq Data," Nucleic Acids Res. 39: D202-D209 (2011), which is hereby incorporated by reference in its entirety) and non-target mRNAs in the HeLa cell dataset could be observed. Indeed, miR-155 target mRNAs were significantly more suppressed in miR-155-transfected HeLa cells. This confirms that miR-155 target mRNA degradation can be detected in this dataset (n=1,131 (target); 7,700 (non-target; data represent the average from two independent datasets; each box shows the first quartile, median, and third quartile; whiskers represent 1.5× interquartile ranges; grey dots represent outliers; one-way ANOVA with Tukey's post hoc test, P≤2.2×10$^{-16}$). FIG. 13H is a graph showing that m$^6$A$_m$ mRNAs show resistance to miR-155-mediated mRNA degradation. Whether the identity of the first nucleotide affects the response of miR-155 target mRNAs to miR-155-mediated mRNA degradation was next tested. miR-155 target mRNAs that start with m$^6$A$_m$ were observed to show no significant suppression upon miR-155 transfection compared to non-target mRNAs that start with m$^6$A$_m$. However, expression of miR-155 target mRNAs that start with A$_m$, C$_m$, G$_m$, or U$_m$ was significantly suppressed compared to non-target mRNAs that start with A$_m$, C$_m$, G$_m$, or U$_m$. These data suggest that the presence m$^6$A$_m$ can reduce the silencing efficiency of a single microRNA in vivo (n=1,714 versus 232 (m$^6$A$_m$, non-target versus target); 953 versus 158 (A$_m$, non-target versus target); 1,848 versus 281 (C$_m$, non-target versus target); 1,394 versus 182 (G$_m$); 1,809 versus 278 (U$_m$, non-target versus target); each box shows the first quartile, median, and third quartile; whiskers represent 1.5× interquartile ranges; one-way ANOVA with Tukey's post hoc test, *P≤0.05 non-target versus miR-155 target, P≤0.01 non-target versus miR-155 target, *P≤0.001 non-target versus miR-155 target).

DETAILED DESCRIPTION OF THE INVENTION

Figures 1A, 1B, 1C, 1D, 1E, 1F:
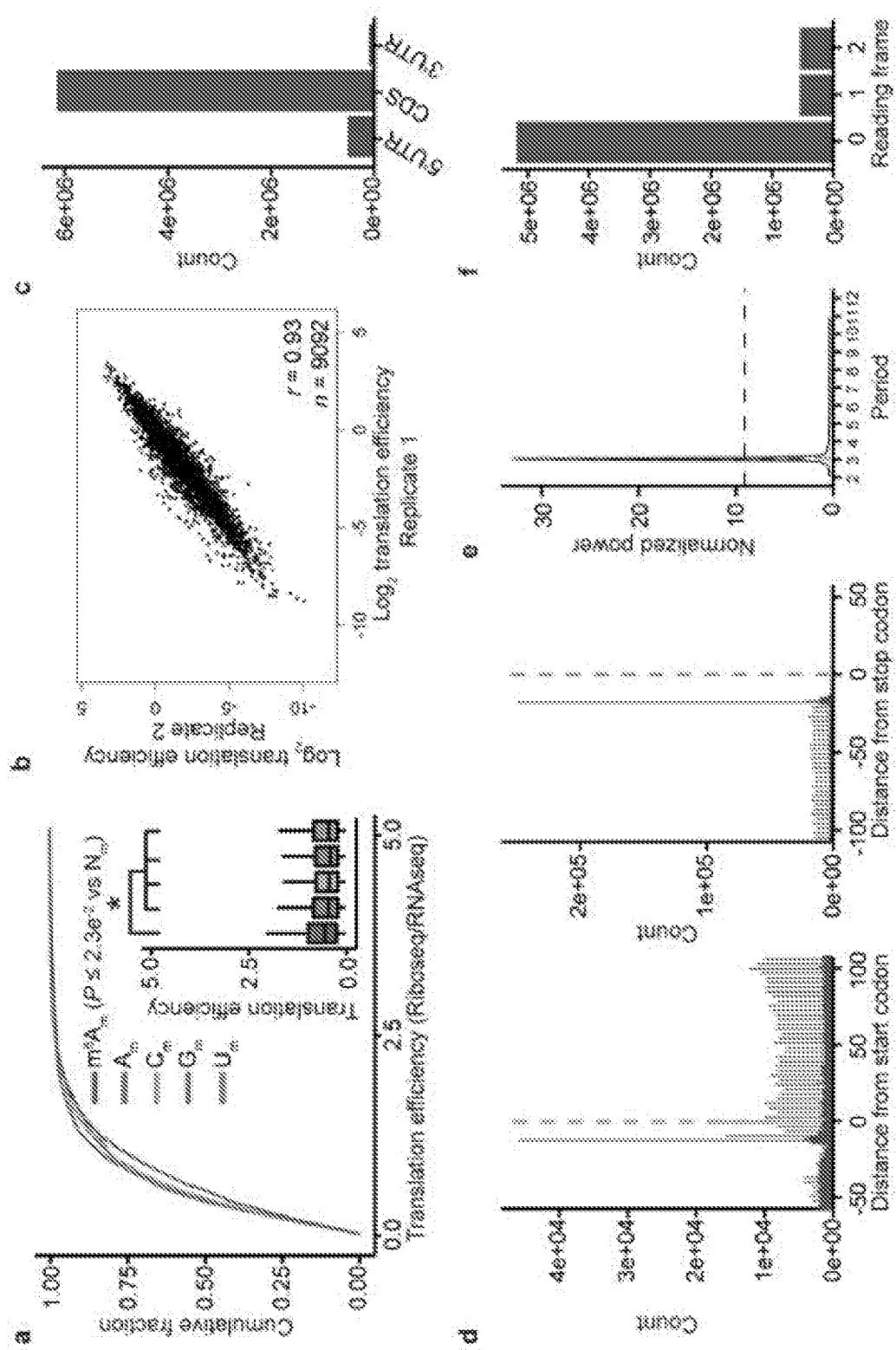
FIGS. 1A-1F show that m⁶A$_m$ mRNAs show increased translation efficiency.

The present invention relates to methods of making RNA modifications to enhance the translation ability and/or stability of RNA molecules, to methods and kits for enhancing translation of RNA molecules and providing treatment, and to the synthesis of RNA molecules.

In one aspect, the present invention relates to a method of enhancing the translation ability and stability of an RNA molecule. This method involves providing a cell-free composition comprising an RNA molecule to be translated, where the RNA molecule lacks an N$^6$,2'-O-dimethyladenosine (m$^6$A$_m$) residue; introducing an m$^6$A$_m$ residue at the first 5' nucleotide of the RNA molecule; and adding an m$^7$G nucleotide and triphosphate linker to the M$^6$A$_m$ residue to create a cap structure to enhance translation ability and stability of the RNA molecule relative to the RNA molecule lacking an m$^6$A$_m$ or a m$^7$G-ppp-m$^6$A$_m$ at the 5' end of the RNA molecule.

As used herein, the term "cell-free composition" refers to a composition substantially free of intact cells. An exemplary cell-free composition comprises a cell lysate or extract. The term "cell lysate" refers to a fluid containing the contents of lysed cells. Cell lysates may be crude (i.e., unpurified) or partially purified (e.g., to remove cellular debris/particulate such as damaged outer cell membranes). Methods of forming cell lysates are well-known in the art and include, without limitation, sonication, homogenization, enzymatic lysis using lysozyme, freezing, grinding, and high pressure lysis. Cell-free compositions may comprise, for example, ribosomes, amino acids, tRNAs, aminoacyl synthetases, elongation factors, and initiation factors. The cell-free composition may be derived from eukaryotic cells or prokaryotic cells and include, for example, E. coli cell lysates or extracts. A "cell-free composition" may also include an in vitro reaction medium for carrying out the well-known steps and reactions of protein synthesis.

A person of ordinary skill in the art will appreciate that there are many types of RNA molecules, including coding RNA (i.e., RNA that is translated into a protein, e.g., mRNA) and non-coding RNA. According to one embodiment, in the present invention, the RNA molecule referred to is an mRNA molecule.

The RNA molecule may be a synthetic RNA molecule or a naturally-occurring RNA molecule. As used herein, the term "synthetic RNA molecule" means an engineered or non-naturally-occurring RNA molecule (e.g., an RNA molecule comprising a heterologous sequence, synthetic nucleotides, a mixture of nucleotides and other chemical moieties, or nucleotide modifications). Synthetic RNA molecules include RNA molecules synthesized using any in vitro method known in the art. For example, synthetic RNA molecules may be produced using in vitro transcription reactions or by using an RNA synthesizer. Synthetic RNA molecules may contain one or more modified ribonucleotides or other nucleotides, for example and without limitation, 2'-O-methylated nucleotides, deoxy nucleotides, or 2'-fluoro nucleotides. A "naturally-occurring RNA molecule" means an RNA molecule consisting of a sequence that occurs in nature.

According to one embodiment of the present invention, the RNA molecule has a 5' untranslated region. As used herein, the terms "5' untranslated region" or "5' UTR" refer to an untranslated nucleotide segment in an RNA molecule immediately preceding an AUG start codon. The 5' untranslated region may be located at the 5' end of an RNA molecule or at an internal position of an mRNA sequence.

By "enhancing the translation ability" of the RNA molecule, it is meant that the RNA molecule is more likely to be translated, is more efficiently translated, is translated at a higher rate, is translated under more challenging conditions than what normally exist in nature, or is translated under conditions that require fewer reagents than the same RNA molecule that lacks the methylated adenosine residue in the 5' untranslated region.

Many eukaryotic cellular mRNAs are blocked at their 5'-ends with the 7-methylguanosine five-prime (5') cap structure, m$^7$GpppX (where X is any nucleotide). This structure is involved in several cellular processes including enhanced translational efficiency, splicing, mRNA stability, and RNA nuclear export.

Methods of translating RNA molecules include the use of cell-based (i.e., in vivo) and cell-free (i.e., in vitro) expression systems. Translation or expression of a protein can be carried out by introducing a nucleic acid molecule encoding a protein or protein fragment into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted protein coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express a protein encoding sequence in a cell. Primarily, the vector system must be compatible with the host cell used. Host-vector systems include, but are not limited to, the following: microorganisms such as yeast containing yeast expression vectors; mammalian cell systems infected with a virus (e.g., vaccinia virus, adenovirus, etc.); insect cell systems infected with a virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used.

Depending on the vector system and host utilized, any number of suitable transcription and/or translation elements, including constitutive, inducible, and repressible promoters, as well as minimal 5' promoter elements may be used.

The protein-encoding nucleic acid, a promoter molecule of choice, a suitable 3' regulatory region and, if desired, polyadenylation signals and/or a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a protein is inserted into a vector in the sense (i.e 5'→3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct.

Once the isolated nucleic acid molecule encoding the protein has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, New York (1989), which is hereby incorporated by reference in its entirety. Suitable hosts include, but are not limited to, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In some embodiments of the methods of the present invention, translating the RNA molecule is carried out in a cell-free system. Cell-free expression allows for fast synthesis of recombinant proteins and enables protein labeling with modified amino acids, as well as expression of proteins that undergo rapid proteolytic degradation by intracellular proteases. As described above, exemplary cell-free systems comprise cell-free compositions, including cell lysates and extracts. Whole cell extracts may comprise all the macromolecule components needed for translation and post-translational modifications of eukaryotic proteins. As described above, these components include, but are not limited to, regulatory protein factors, ribosomes, and tRNA.

Introducing a $m^6A_m$ residue in a 5' untranslated region of an RNA molecule and adding an $m^7G$ nucleotide and triphosphate linker to the $m^6A_m$ residue in carrying out the methods of the present invention may be carried out by various means. In one embodiment, introducing a $m^6A_m$ residue in a 5' UTR of the RNA molecule and adding an $m^7G$ nucleotide and triphosphate linker to the $m^6A_m$ residue is carried out by ligating an RNA molecule comprising an $m^7G$-ppp-$m^6A_m$ structure at the 5' end of the RNA molecule to the RNA molecule to be translated. As used herein, the term "ligating" refers to an enzymatic reaction which catalyzes the joining of two nucleic acid molecules by forming a new chemical bond. This method may involve using a T4 DNA ligase and a bridging DNA oligonucleotide complementary to the RNAs, where the T4 DNA ligase is effective to join the RNA molecules to each other when they are in an RNA:DNA hybrid.

In another aspect, the present invention relates to a method of enhancing the translation ability and stability of an RNA molecule. This method involves providing a cell-free composition comprising an RNA molecule to be translated, where the RNA molecule lacks an $m^6A$ residue; introducing an $m^6A$ residue at the first 5' nucleotide of the RNA molecule; adding an $m^7G$ nucleotide and triphosphate linker to the $m^6A$ residue to create a cap structure; and methylating the $m^6A$ residue to form an $m^6A_m$ residue to enhance translation ability and stability of the RNA molecule relative to the RNA molecule lacking an $m^6A_m$ or a $m^7G$-ppp-$m^6A_m$ at the 5' end of the RNA molecule.

Methylating the $m^6A$ residue to form an $m^6A_m$ residue may involve the use of a methyltransferase. As used herein, the term "methyltransferase" refers to transferase class enzymes that are able to transfer a methyl group from a donor molecule to an acceptor molecule, e.g., an adenine base of an RNA molecule. This includes, for example and without limitation, methylation enzymes that are engineered or which are fusions of naturally occurring methylation enzymes and their binding partners. Methyltransferases typically use a reactive methyl group bound to sulfur in S-adenosyl methionine ("SAM") as the methyl donor. In some embodiments, a methyltransferase described herein is an mRNA (2'-O-methyladenosine-N6-)-methyltransferase.

As described in detail above, the RNA molecule may be a synthetic or naturally-occurring RNA molecule.

A further aspect of the present invention relates to a method of enhancing the translation and stability of an RNA molecule. This method involves providing an RNA molecule and adding to the RNA molecule a 5' cap structure comprising a 7-methylguanosine ($m^7G$), a 5' phosphate linker (e.g., a triphosphate linker ("-ppp-")), and an $N^6,2'$-O-dimethyladenosine ($m^6A_m$).

In one embodiment, the RNA molecule comprises ribonucleotides, modified nucleotides, deoxynucleotides, or nucleotide mimetics compatible with ribosome-mediated translation.

The method may further involve adding a poly(A) tail to the RNA molecule.

Another aspect of the present invention relates to a method of making an RNA molecule. This method involves providing an RNA molecule having a methylated adenosine ($m^6A$) residue at the first transcribed base of an mRNA molecule and capping the RNA molecule with a $m^7G$ cap under conditions effective to convert the $m^6A$ residue to an $N^6,2'$-O-dimethyladenosine ($m^6A_m$) residue to make an RNA molecule comprising an $m^6A_m$ residue at the first 5' nucleotide of the RNA molecule.

In one embodiment, the RNA molecule is capped with a capping enzyme (e.g., a Vaccinia capping enzyme, available from, e.g., New England Biolabs) to produce an $m^7G$ capped RNA molecule. In accordance with this embodiment, the first transcribed bases of the $m^7G$ capped RNA molecule, $m^6A_m$ is methylated to form an $N^6,2'$-O-dimethyladenosine ($m^6A_m$) residue with a mRNA Cap 2'-O-Methyltransferase (e.g., a Vaccinia mRNA Cap 2'-O-Methyltransferase).

In another aspect, the present invention relates to a method of making an RNA molecule that involves transcribing an RNA molecule in the presence of a primer comprising a methylated adenosine ($m^6A$) residue at the 5' end of the primer in the presence of primer-dependent RNA polymerase and capping the RNA molecule with a $m^7G$ cap under conditions effective to convert the $m^6A$ residue to an $N^6,2'$-O-dimethyladenosine ($m^6A_m$) residue to make an RNA molecule comprising an $m^6A_m$ residue in the first 5' nucleotide of the RNA molecule.

According to one embodiment of this and other methods of making an RNA molecule of the present invention, the primer-dependent RNA polymerase is TGK polymerase. TGK polymerase is well known in the art as a thermostable RNA polymerase which enables RNA synthesis with an RNA primer from a DNA template (see PCT Publication No. WO 2011/135280, which is hereby incorporated by reference in its entirety).

In carrying out this and other methods of making an RNA molecule of the present invention, the method may further involve adding a poly(A) tail to the mRNA molecule. As used herein, the term "poly(A) tail" refers to a consecutive sequence of adenylic acids that are normally present at the 3' terminal of eukaryotic mRNA. The poly(A) tail is involved in stabilization, translation, and transport of mRNA from nucleus to cytoplasm. Methods of polyadenylating mRNA are well known in the art.

In yet another aspect, the present invention relates to a method of making an RNA molecule that involves transcribing an RNA molecule in the presence of a primer comprising a $m^7G$ cap followed by an $N^6,2'$-O-dimethyladenosine ($m^6A_m$) residue at the 5' end of the primer under conditions effective to make an RNA molecule comprising an $m^6A_m$ residue in the first 5' nucleotide of the RNA molecule.

In another aspect, the present invention further relates to a method of making an RNA molecule. This method involves providing a reaction solution comprising an mRNA molecule comprising a 5' $m^7G$ cap followed by an adenosine residue as the first 5' residue and enzymes capable of 2'-O-methylating and $N^6$-methylating the adenosine residue to make an RNA molecule comprising an $m^6A_m$ residue in the first 5' nucleotide of the RNA molecule.

Enzymes capable of 2'-O-methylating $m^6A$ residues include, but are not limited to, the Vaccinia mRNA Cap 2'-O-Methyltransferase. Enzymes capable $N^6$-methylating the adenosine residues include, but are not limited to, $m^6A$-Methyltransferases.

In yet another aspect, the present invention relates to a method of making an RNA molecule. This method involves providing an RNA molecule comprising a 5' $N^6$-methyladenosine ($m^6A$) residue and adding to the RNA molecule a 5' $m^7G$ cap.

In one embodiment of this method, adding to the RNA molecule a 5' $m^7G$ cap is carried out in the presence of a vaccinia capping enzyme.

In another embodiment, modifying the RNA molecule involves introducing into the RNA molecule a 2'-O-methyl group on the $m^6A$ residue to form $m^6A_m$.

In yet another embodiment, the method further involves adding a poly(A) tail to the RNA molecule.

A further aspect of the present invention relates to a treatment. This method involves contacting a cell with an RNA molecule comprising an $N^6,2'$-O-dimethyladenosine ($m^6A_m$) residue at the first 5' nucleotide of the RNA molecule under conditions effective to cause translation of the RNA molecule to treat the cell.

In one embodiment, the RNA molecule comprising an $m^6A_m$ residue at the first 5' nucleotide means that the RNA molecule has an $m^6A_m$ residue at the first position, or the first position after an $m^7G$ cap.

According to one embodiment, this and other treatment methods described herein are effective to treat a cell under a stress or disease condition. Exemplary cell stress conditions may include, without limitation, exposure to a toxin; exposure to chemotherapeutic agents, irradiation, or environmental genotoxic agents such as polycyclic hydrocarbons or ultraviolet ("UV") light; exposure of cells to conditions such as glucose starvation, inhibition of protein glycosylation, disturbance of $Ca^{2+}$ homeostasis and oxygen; exposure to elevated temperatures, oxidative stress, or heavy metals; exposures to a pathological disease state (e.g., diabetes, Parkinson's disease, cardiovascular disease (e.g., myocardial infarction, end-stage heart failure, arrhythmogenic right ventricular dysplasia, and Adriamycin-induced cardiomyopathy), and various cancers (Fulda et al., "Cellular Stress Responses: Cell Survival and Cell Death," *Int. J. Cell Biol.* (2010), which is hereby incorporated by reference in its entirety)), and combinations thereof.

Additional exemplary stress or disease conditions include those of a cell undergoing a viral infection. By impairing cap-dependent ribosome recruitment to host mRNAs, many viruses globally interfere with host mRNA translation, crippling host antiviral responses, and favoring viral protein synthesis. Some viruses directly target degradation of cellular translation factors to prevent ribosome recruitment by host mRNAs. For example, poliovirus (an enterovirus), feline calicivirus, and retroviruses each encode proteases that cleave eIF4Q separating its (amino-terminal) eIF4E-interacting domain from its eIF4A- and eIF3-binding segment, thereby inhibiting cap-dependent protein synthesis in a eukaryotic cell. Vesicular stomatitis virus ("VSV"), influenza virus, and adenovirus ("Ad") decrease eIF4E phosphorylation, resulting in the accumulation of unphosphorylated eIF4E. Other viruses, including encephalomyocarditis virus ("EMCV"), poliovirus, cricket paralysis virus ("CrPV"), VSV, Sindbis virus ("SINV"), Dengue virus ("DENV"), and reovirus, as well as small DNA viruses such as SV40, impact initiation factors indirectly by, for example, inducing the accumulation of proteins which sequester the cap-binding subunit eIF4E and preventing eIF4F assembly.

In some embodiments, contacting a cell with an RNA molecule involves introducing an RNA molecule into a cell. Suitable methods of introducing RNA molecules into cells are well known in the art and include, but are not limited to, the use of transfection reagents, electroporation, microinjection, or via RNA viruses.

The cell may be a eukaryotic cell. Exemplary eukaryotic cells include a yeast cell, an insect cell, a fungal cell, a plant cell, and an animal cell (e.g., a mammalian cell). Suitable mammalian cells include, for example without limitation, human, non-human primate, cat, dog, sheep, goat, cow, horse, pig, rabbit, and rodent cells.

In certain embodiments of the treatment methods of the present invention, the RNA molecule encodes a therapeutic protein or peptide sequence. The therapeutic protein may be endogenous or heterologous to the cell. The therapeutic protein may be down-regulated in a disease state, a stress state, or during a pathogen infection of a cell.

Treating cells also includes treating the organism in which the cells reside. Thus, by this and the other treatment methods of the present invention, it is contemplated that treatment of a cell includes treatment of a subject in which the cell resides.

In a further aspect, the invention relates to a treatment method that involves contacting a cell with a DNA molecule encoding an RNA molecule that will contain upon in-cell or in vivo transcription a 5' $m^7G$ cap and an $N^6,2'$-O-dimethyladenosine ($m^6A_m$) residue in the first encoded 5' nucleotide of the RNA molecule under conditions effective for the DNA molecule to be transcribed to produce an RNA molecule comprising an $m^6A_m$ residue in the first 5' nucleotide of the RNA molecule such that the RNA molecule is translated to treat the cell.

Another aspect of the present invention relates to a method of synthesizing an RNA molecule. This method involves transcribing a DNA molecule in a cell-free composition to synthesize an RNA molecule comprising a cap structure at the 5' end of the RNA molecule, where the cap structure comprises an $m^7G$ or $m^7G$-like residue, a phosphate linker, and an $m^6A_m$ residue ($m^7G$-(p)-$m^6A_m$, where p is a phosphate and n is an integer from 1-20), where the phosphate linker links the $m^7G$ or $m^7G$-like residue to the $m^6A_m$ residue.

In one embodiment, the $m^7G$-(p)-$m^6A_m$ cap structure enhances the translation ability of the RNA molecule relative to the RNA molecule lacking the $m^7G$-(p)-$m^6A_m$ cap structure. In another embodiment, the $m^7G$-(p)-$m^6A_m$ cap structure enhances the stability of the RNA molecule relative to the RNA molecule lacking the $m^7G$-(p)-$m^6A_m$ cap structure. In a further embodiment, the $m^7G$-(p)-$m^6A_m$ cap structure enhances both the translation ability and stability of the RNA molecule relative to the RNA molecule lacking the $m^7G$-(p)-$m^6A_m$ cap structure.

In one embodiment, an RNA molecule comprising a cap structure at the 5' end of the RNA molecule according to this and other aspects of the present invention, may be carried out by ligating an RNA molecule comprising an $m^7G$-(p)-$m^6A_m$ structure to the 5' end of an RNA molecule to be translated. As used herein, the term "ligating" refers to an enzymatic reaction which catalyzes the joining of two nucleic acid molecules by forming a new chemical bond. This method may involve using a T4 DNA ligase and a bridging DNA oligonucleotide complementary to the RNAs, where the T4 DNA ligase is effective to join the RNA molecules to each other when they are in an RNA:DNA hybrid.

The method may further involve adding a poly(A) tail to the RNA molecule.

These aspects of the present invention are further illustrated by the examples below.

EXAMPLES

Materials and Method for Examples 1-7

Synthesis and Characterization of Synthetic Oligonucleotides:

The sequences of all the oligonucleotides used in this study are shown in Table 1. The oligonucleotide containing an internal $N^6$-methyladenosine ($m^6A$) in a DRACH context was synthesized by TriLink BioTechnologies.

TABLE 1

Characterization of Oligonucleotide Sequences

| | | MALDI-TOF MS | |
|---|---|---|---|
| Oligonucleotide sequence | SEQ ID NO. | Calculated m/z | Found m/z |
| 5'-$m^7$GpppACACUUGCUUUUGACACAACU-3' | SEQ ID NO: 1 | 7097.13 | 7096.86 |
| 5'-$m^7$Gpppm$^6$ACACUUGCUUUUGACACAACU-3' | SEQ ID NO: 2 | 7111.15 | 7110.47 |
| 5'-$m^7$GpppA$_m$CACUUGCUUUUGACACAACU-3' | SEQ ID NO: 3 | 7111.15 | 7111.63 |
| 5'-$m^7$Gpppm$^6$A$_m$CACUUGCUUUUGACACAACU-3' | SEQ ID NO: 4 | 7125.18 | 7126.49 |
| 5'-$m^7$GpppACm$^6$ACUUGCUUUUGACACAACU-3' | SEQ ID NO: 5 | 7111.15 | 7110.57 |
| 5'-Gpppm$^6$A$_m$CACUUGCUUUUGACACAACU-3' | SEQ ID NO: 6 | 7110.14 | 7111.3 |
| 5'-AGUGGm$^6$ACUAACCACCAUGGAAGGU-3' | SEQ ID NO: 7 | — | — |

TABLE 1-continued

Characterization of Oligonucleotide Sequences

| Oligonucleotide sequence | SEQ ID NO. | MALDI-TOF MS Calculated m/z | Found m/z |
|---|---|---|---|
| 5'-pm$^6$A$_m$CACUUGCUUUUGACACAACU-3' | SEQ ID NO: 8 | 6684.96 | 6686.48 |
| 5'-pppm$^6$A$_m$CACUUGCUUUUGACACAACU-3' | SEQ ID NO: 9 | 6844.92 | 6846.4 |
| 5'-pppAGCACUUGCUUUUGACACAACU-3' | SEQ ID NO: 10 | 7162.07 | 7162.04 |
| 5'-pppm$^6$AGCACUUGCUUUUGACACAACU-3' | SEQ ID NO: 11 | 7176.1 | 7176.2 |
| 5'-pppm$^6$A$_m$GCACUUGCUUUUGACACAACU-3' | SEQ ID NO: 12 | 7190.12 | 7191.25 |
| 5'-pppA$_m$GCACUUGCUUUUGACACAACU-3' | SEQ ID NO: 13 | 7176.1 | 7177.14 |

All other synthetic RNA oligonucleotides were chemically assembled on an ABI 394 DNA synthesizer (Applied Biosystems) from commercially available long-chain alkylamine controlled-pore glass ("LCAA-CPG") solid support with a pore size of 1,000 Å derivatized through the succinyl linker with 5'-O-dimethoxytrityl-2'-O—Ac-uridine (Link Technologies). All RNA sequences were prepared using phosphoramidite chemistry at 1 µmol scale in Twist oligonucleotide synthesis columns (Glen Research) from commercially available 2'-O-pivaloyloxymethyl amidites (5'-O-DMTr-2'-O-PivOM-[U, $C^{Ac}$, $A^{Pac}$, or $G^{Pac}$]-3'-O—(O-cyanoethyl-N,N-diisopropylphosphoramidite) (Debart et al., Current Protocols in Nucleic Acid Chemistry, Beaucage S, et al., eds. Vol. 43, John Wiley & Sons, Inc.; 2010. pp. 3.19.11-3.19.27, which is hereby incorporated by reference in its entirety) (Chemgenes). The 5' terminal adenosine can be unmodified A, methylated in 2'-OH ("A$_m$"), or in N$^6$ position (m$^6$A), or in both positions (m$^6$A$_m$). The 5'-O-DMTr-2'-O-Me-A$^{Pi}$-3'-O—(O-cyanoethyl-N,N-diisopropylphosphoramidite) (Chemgenes) was used to introduce A$_m$ at the 5'-end of RNA. For the production of m$^6$A-RNAs or m$^6$A$_m$-RNAs, the preparation of m$^6$A and m$^6$A$_m$ phosphoramidite building blocks was performed by a selective one-step methylation of the commercially available 2'-O-PivOM-Pac-A-CE phosphoramidite or 2'-O-Me-Pac-A-CE phosphoramidite, respectively. All oligoribonucleotides were synthesized using standard protocols for solid-phase RNA synthesis with the PivOM methodology (Lavergne et al., "A Base-Labile Group for 2'-OH Protection of Ribonucleosides: A Major Challenge for RNA Synthesis," Chemistry 14:9135-9138 (2008), which is hereby incorporated by reference in its entirety).

After RNA assembly, the 5'-hydroxyl group of the 5'-terminal adenosine ("A"): A, A$_m$, m$^6$A or m$^6$A$_m$ of RNA sequences, still anchored to solid support, was phosphorylated and the resulting H-phosphonate derivative was oxidized and activated into a phosphoroimidazolidate derivative to react with either pyrophosphate (for ppp(A)-RNA synthesis) (Zlatev et al., "Chemical Solid-Phase Synthesis of 5'-Triphosphates of DNA, RNA, and Their Analogues," Org. Lett. 12:2190-2193 (2010), which is hereby incorporated by reference in its entirety) or guanosine diphosphate (for Gppp(A)-RNA synthesis) (Thillier et al., "Synthesis of 5' Cap-0 and Cap-1 RNAs Using Solid-Phase Chemistry Coupled with Enzymatic Methylation by Human (Guanine-N7)-Methyl Transferase," RNA 18:856-868 (2012), which is hereby incorporated by reference in its entirety). To obtain the monophosphate of m$^6$A$_m$-RNA ("pm$^6$A$_m$-RNA"), the 5'-H-phosphonate RNA was treated with a mixture of N,O-bis-trimethylacetamide and triethylamine in acetonitrile, and then oxidized with a tert-butyl hydroperoxide solution (Paesen et al., "X-ray Structure and Activities of an Essentia Mononegavirales L-Protein Domain," Nat. Commun. 6:8749 (2015), which is hereby incorporated by reference in its entirety).

After deprotection and release from the solid support upon basic conditions (DBU then aqueous ammonia treatment for 4 hours at 37° C.), all RNA sequences were purified by IEX-HPLC (Banal et al., "Development of Specific Dengue Virus 2'-O- and N7-Methyltransferase Assays for Antiviral Drug Screening," Antiviral Res 99:292-300 (2013), which is hereby incorporated by reference in its entirety), they were obtained with high purity (>95%) and they were unambiguously characterized by MALDI-TOF spectrometry (Table 1).

N$^7$ methylation of the purified Gppp(A)-RNAs to give m$^7$Gppp(A)-RNAs was carried out quantitatively using human mRNA guanine-N$^7$-methyltransferase and S-adenosylmethionine as previously described (Thillier et al., "Synthesis of 5' Cap-0 and Cap-1 RNAs Using Solid-Phase Chemistry Coupled with Enzymatic Methylation by Human (Guanine-N7)-Methyl Transferase," RNA 18:856-868 (2012), which is hereby incorporated by reference in its entirety).

Measurement of Enzymatic Properties of FTO In Vitro:

Demethylation measurements were performed essentially as described previously (Jia et al., "N6-Methyladenosine in Nuclear RNA is a Major Substrate of the Obesity-Associated FTO," Nat. Chem. Biol. 7:885-887 (2011), which is hereby incorporated by reference in its entirety), with the exception that all reactions were carried out at 37° C. The demethylation activity assay was performed in 20-50 µl of reaction mixture containing the indicated quantities of synthetic RNA oligonucleotide or mRNA, the indicated quantities of FTO, 75 mM of $(NH_4)_2Fe(SO_4)_2$, 300 mM α-ketoglutarate, 2 mM sodium L-ascorbate, 150 mM KCl, and 50 mM HEPES buffer, pH 7.0. The reaction was incubated at 37° C. for the indicated times, quenched by the addition of 1 mM of EDTA followed by inactivation of the enzymes for 5 min at 95° C.

Sample Preparation for HPLC Analysis:

After demethylation by FTO, oligonucleotides were decapped with 25 units of RppH (NEB) in ThermoPol buffer for 2 hours at 37° C. RNA was subsequently digested to single nucleotides with 180 units of S1 nuclease (Takara) for 1 hour at 37° C. 5' phosphates were removed with 5 units of rSAP (NEB) for 1 hour at 37° C. Before loading the samples onto the HPLC column, proteins were removed by size-exclusion chromatography with a 10 kDa cut-off filter (VWR).

HPLC Analysis of Demethylation Activity:

The HPLC analysis of nucleosides was performed on an Agilent 1100 system (Agilent Technologies). Separation was performed on a Poroshell 120 EC-C18 column (4 µm, 150×4.6 mm, Agilent Technologies) equipped with an EC-C18 Guard cartridge (Agilent Technologies) at 22° C. The mobile phase consisted of buffer A (25 mM $NaH_2PO_4$) and buffer B (100% acetonitrile). Pump control and peak integration was achieved using the Chem Station software (Rev. A.10.02, build 1757, Agilent Technologies). Samples were analyzed at 2 ml $min^{-1}$ flow rate with the following buffer A/B gradient: 7.5 min 95%/5%, 0.5 min 90%/10%, 2 min 10%/90%, 1 min 95%/5%. Retention times of the individual nucleosides was determined with synthetic standards (3.2 min for adenosine (A), 5.8 min for 2'-O-methyladenosine ($A_m$), 5.9 min for $N^6$-methyladenosine ($m^6A$), 7.9 min for $N^6,2'$-O-dimethyladenosine ($m^6A_m$)). Guanosine was used as an internal control. After normalization of each peak area to the area of the guanosine peak area, the relative and absolute amount of individual nucleotides in each sample was determined based on the sequence of the input oligonucleotide.

Sample Preparation for Mass Spectrometry:

$m^6A_m$ demethylation intermediates were generated essentially as described previously (Fu et al., "FTO-Mediated Formation of N6-hydroxymethyladenosine and N6-Formyladenosine in Mammalian RNA," *Nat. Commun.* 4:1798 (2013), which is hereby incorporated by reference in its entirety), with the difference that all reactions were carried out at 37° C. Capped oligonucleotides were incubated with 100 nM FTO for 10 min at 37° C. followed by digestion with 2 units of P1 nuclease for an additional 15 minutes. Notably, P1 nuclease does not cleave the triphosphate linker of the cap and thus specifically releases the $m^7Gpppm^6A_m$ dinucleotide, while digesting the RNA backbone down to single nucleotides. To preserve the unstable demethylation intermediates (Fu et al., "FTO-Mediated Formation of N6-Hydroxymethyladenosine and N6-Formyladenosine in Mammalian RNA," *Nat. Commun.* 4:1798 (2013), which is hereby incorporated by reference in its entirety), the nucleotide mixture was immediately frozen in liquid nitrogen until further analysis.

Detection of Demethylation Intermediates by Mass Spectrometry:

FTO reaction products were extracted by cold 80% methanol: $H_2O$ at 1:20 volume ratio. After removal of precipitated protein, 4 µl of supernatant was injected into LC/MS for accurate mass measurement of demethylation intermediates. The LC/MS-MS system comprised an Agilent Model 1260 Bio-inert infinity liquid chromatography system coupled to an Agilent iFunnel 6550 quadrupole time-of-flight mass spectrometer. Chromatography of the reaction products was performed using aqueous normal phase ("ANP") gradient separation, on Cogent Diamond Hydride ("ANP") column (2.1×150 mm, 3.5 µm particle size; Microsolv Technology Corp). A precolumn filter (0.5 µm, Microsolv) was placed in front of the ANP column, to prevent column clogging. Mobile phases consisted of: (A) 50% isopropanol, containing 0.025% acetic acid; and (B) 90% acetonitrile containing 5 mM ammonium acetate. To eliminate the interference of metal ions on the chromatographic peak integrity and electrospray ionization, EDTA was added to the mobile phase at a final concentration of 6 µM. The following gradient was applied: 0-1.0 min, 99% B; 1.0-15.0 min, to 20% B; 15.0-29.0 min, 0% B; 29.1-37 min, 99% B. To minimize potential salt and other contaminants in the ESI source, a time segment was set to direct the first 0.5 min of column elute to waste.

Negative ion mass spectra in both profile and centroid mode were acquired in 2 GHz (extended dynamic range) mode, scanned at 1 spectrum per second over a mass/charge range of 20-1,000 Daltons. The QTOF capillary voltage was set 3,500 V and the fragmentor was set to 140 V. The nebulizer pressure was 35 p.s.i. and the nitrogen drying gas was 200° C., delivered at a flow rate of 14 l $min^{-1}$. The sheath gas temperature was at 350° C. with sheath gas flow of 11 l $min^{-1}$. Raw data was analyzed with Agilent MassHunter Qualitative Analysis software (version B6.0). Profile data was used to provide measured mass.

Cell Culture and Animals:

HEK 293T/17 (ATCC CRL-11268; passage number 3-10; no further verification of cell line identity was performed) cells were maintained in DMEM (11995-065, ThermoFisher Scientific) with 10% FBS and antibiotics (100 units $ml^{-1}$ penicillin and 100 µg $ml^{-1}$ of streptomycin) under standard tissue culture conditions. Cells were split using TrypLE Express (Life Technologies) according to the manufacturer's instructions. *Mycoplasma* contamination in cells was routinely tested by Hoechst staining. To obtain embryonic day (E) 14 Fto-knockout mouse embryos and livers, Fto-knockout mice were bred as previously described (Fischer et al., "Inactivation of the Fto Gene Protects From Obesity," Nature 458:894-898 (2009), which is hereby incorporated by reference in its entirety). Only male animals were used in the study.

Antibodies:

Antibodies used for western blot analysis or immunostaining were as follows: rabbit anti-DDDDK/Flag (ab1162, Abcam), rabbit anti-FTO (ab124892, Abcam), rabbit anti-GAPDH (ab9485, Abcam), mouse anti-ALKBH5 (ab69325, Abcam), mouse (β-actin (A2228, Sigma), and goat anti-rabbit IgG Alexa Fluor 546 (A11035, ThermoFisher Scientific). For $m^6A$ individual-nucleotide-resolution cross-linking and immunoprecipitation (miCLIP), rabbit anti-$m^6A$ (ab151230, Abcam) was used. An in-house-generated rabbit anti-DCP2 serum was used for detection of DCP2.

Knockdown and Overexpression Studies in HEK293T Cells:

FTO and ALKBH5 knockdown experiments were carried out in HEK293T cells using either Pepmute transfection reagent (Signagen) or Lipofectamine RNAiMAX (ThermoFisher Scientific) with 20 nM dsiRNA duplex directed against FTO (HSC.RNAI. N001080432.12.1, Integrated DNA Technologies) or 50 nM Silencer Select siRNA duplex pool targeting ALKBH5 (s29686, s29687, s29688, ThermoFisher Scientific), respectively. Scrambled siRNA was used as non-targeting control.

FTO and ALKBH5 expression experiments were carried out in HEK293T cells using LipoD293 transfection reagent (Signagen) with Flag-tagged full length human wild-type FTO, human wild-type FTO containing a Flag tag and two nuclear export signals ("NES") at the N terminus, GST-tagged ALKBH5 lacking 66 N-terminal amino acids, or respective control vectors.

Cells were maintained at 70-80% confluency and harvested 48-72 hours after the transfection. Knockdown and overexpression were confirmed by Western blot. Total RNA was isolated using TRIzol (ThermoFisher Scientific) according to the manufacturer's instructions. If indicated, two rounds of poly(A) mRNA enrichment from total RNA was carried out with oligo d(T)25 Magnetic Beads (NEB) according to the manufacturer's instructions.

Immunostaining of HEK293T Cells:

HEK293T cells transfected with either Flag-tagged full-length human wild-type FTO or human wild-type FTO containing two nuclear export signals ("NES") at the N terminus were grown on cover slips coated with poly-d-lysine, fixed with 4% paraformaldehyde in PEM buffer (80 mM potassium PIPES, 5 mM EGTA, 2 mM $MgCl_2$, pH 7.0) for 10 minutes and permeabilized with 0.5% Triton™ X-100 in PEM buffer for 30 minutes. After blocking with 1% BSA in TBS-T for 1 hour, cells were incubated with anti-DDDDK/Flag antibody (1:1,000 dilution in 1% BSA TBS-T) for 2 hours followed by incubation with a goat anti-rabbit IgG antibody (1:1,000 dilution in 1% BSA TBS-T) for 1 hour. Nuclei were stained with DAPI. All immunostaining steps were carried out at room temperature. Image acquisition was carried out on a Nikon Eclipse Ti microscope (Nikon), using NIS-Elements AR software (Version 3.2).

Generation of DCP2 CRISPR Knockout Cells:

DCP2-knockout cell lines were generated by CRISPR/Cas9 technology using two guide RNAs (gRNAs; 5'-UAU-CAAAGACUAUAUUUGUA-3' (SEQ ID NO:14) and 5'-AACCAGUUUCUUCAAAG ACC-3' (SEQ ID NO:15)) designed to target the DCP2 genomic region corresponding to its catalytic site. Double-stranded DNA oligonucleotides corresponding to the gRNAs were inserted into the pSpCas9n(BB)-2A-Puro vector (Addgene). Equal amounts of the two gRNA plasmids were mixed and transfected into HEK293T cells using FuGENE 6 (Promega). The transfected cells were then subject to puromycin selection for three days and viable cells were used for serial dilution to generate single-cell clones. The genomic modification was screened by PCR and sequencing. In DCP2-knockout line 1, the two alleles were disrupted to generate out-of-frame mutation after V145 and I153, respectively. Line 2 contained a 55 nucleotide homozygous deletion that removed the splicing site between intron 4 and exon 5. Line 3 contained one allele with a 194 nucleotide deletion that removed the splicing site between intron 4 and exon 5, and the other allele was disrupted to generate out-of-frame mutation after V145. Loss of DCP2 protein expression was confirmed by Western blot with in-house-generated anti-DCP2 sera (Wang et al., "The hDcp2 Protein is a Mammalian mRNA Decapping Enzyme," *PNAS* 99:12663-12668 (2002), which is hereby incorporated by reference in its entirety).

Protein Expression and Purification:

N-terminal HIS-tagged human FTO was generated by standard PCR-based cloning strategy and its identity was confirmed by sequencing FTO as described previously (Jia et al., "N6-Methyladenosine in Nuclear RNA is a Major Substrate of the Obesity-Associated FTO," *Nat. Chem. Biol.* 7:885-887 (2011), which is hereby incorporated by reference in its entirety), with minor modifications. FTO was overexpressed in *E. coli* BL21 Rosetta (DE3) using pET-28(+) (Novagen). Cells expressing FTO were induced with 0.5 mM isopropyl β-D-1-thiogalactopyranoside) ("IPTG") for 16 hours at 18° C. Cells were collected, pelleted, and then resuspended in buffer A (50 mM $NaH_2PO_4$ pH 7.2, 300 mM NaCl, 20 mM imidazole-HCl pH 7.2, 5 mM (3-mercaptoethanol)). The cells were lysed by sonication and then centrifuged at 10,000 g for 20 minutes. The soluble proteins were purified using Talon Metal Affinity Resin (Contech) and eluted in buffer B (50 mM $NaH_2PO_4$ pH 7.2, 300 mM NaCl, 250 mM imidazole-HCl pH 7.2, 5 mM (3-mercaptoethanol). Further concentration and purification was performed using Amicon Ultra-4 spin columns (Merck-Millipore). Recombinant protein was stored in enzyme storage buffer (20 mM HEPES pH 8.0, 50 mM NaCl, 10% glycerol) at −80° C. All protein purification steps were performed at 4° C.

Determination of Relative $m^6A_m$, $A_m$', and $m^6A$ Levels by Thin Layer Chromatography ("TLC"):

Levels of internal $m^6A$ in mRNA were determined by TLC essentially as previously described (Jia et al., "N6-Methyladenosine in Nuclear RNA is a Major Substrate of the Obesity-Associated FTO," *Nat. Chem. Biol.* 7:885-887 (2011), which is hereby incorporated by reference in its entirety). In brief, poly(A) RNA (100 ng) was digested with 2 units of RNase T1 (Thermo Fisher Scientific) for 2 hours at 37° C. in the presence of RNasin RNase Inhibitor (Promega). Ti cuts after every guanosine and exposes the 5'-hydroxyl of the following nucleotide, which can be A, C, U, or $m^6A$. Thus, this method quantifies $m^6A$ in a GA sequence context. 5' ends were subsequently labelled with 10 units of T4 PNK (NEB) and 0.4 mBq [γ-$^{32}$P] ATP at 37° C. for 30 minutes followed by removal of the γ-phosphate of ATP by incubation with 10 units Apyrase (NEB) at 30° C. for 30 minutes. After phenol-chloroform extraction and ethanol precipitation, RNA samples were resuspended in 10 μl of DEPC-$H_2O$ and digested to single nucleotides with 2 units of P1 nuclease (Sigma) for 3 hours at 37° C. 1 μl of the released 5' monophosphates from this digest were then analyzed by 2D TLC on glass-backed PEI-cellulose plates (Merck-Millipore) as described previously (Kruse et al., "A Novel Synthesis and Detection Method for Cap-Associated Adenosine Modifcations in Mouse mRNA," *Sci. Rep.* 1:126 (2011), which is hereby incorporated by reference in its entirety).

The protocol to detect the $m^6A_m/A_m$ ratio was based on the protocol developed by others (Kruse et al., "A Novel Synthesis and Detection Method for Cap-Associated Adenosine Modifcations in Mouse mRNA," *Sci. Rep.* 1:126 (2011), which is hereby incorporated by reference in its entirety), with some modifications. Poly(A) RNA (1 μg) was used for the assay. Free 5'-OH ends were phosphorylated using 30 units of T4 polynucleotide kinase (PNK, NEB) and 1 mM ATP, according to the manufacturer's instructions. 5' phosphorylated RNA fragments were digested with 2 units of Terminator 5'-Phosphate-Dependent Exonuclease (Epicentre). Capped RNAs are unaffected by this treatment. After phenol-chloroform extraction and ethanol precipitation, RNA samples were resuspended in 10 μl of DEPC-$H_2O$ and 400 ng of the RNA was decapped with 25 units of RppH (NEB) for 3 hours at 37° C. The 5' phosphates of the exposed cap-adjacent nucleotide were removed by the addition of 5 units of rSAP (NEB) and further incubated for 30 minutes at 37° C. Up to this point, all enzymatic reactions were performed in the presence of SUPERase In RNase Inhibitor (Thermo Fisher Scientific). After phenol-chloroform extraction and ethanol precipitation, RNA samples were resuspended in 10 μl of DEPC-$H_2O$ and 5' ends were labelled using 30 units T4 PNK and 0.8 mBq [γ-$^{32}$P] ATP at 37° C. for 30 minutes. PNK was heat inactivated at 65° C. for 20 minutes and the reaction was passed through a P-30 spin column (Bio-Rad) to remove unincorporated isotope. 10 μl of labelled RNA were then digested with 4 units of P1 nuclease (Sigma) for 3 hours at 37° C. 4 μl of the released 5' monophosphates from this digest were then analyzed by 2D TLC on glass-backed PEI-cellulose plates (Merck-Millipore) as described previously (Kruse et al., "A Novel Synthesis and Detection Method for Cap-Associated Adenosine Modifications in Mouse mRNA," *Sci. Rep.* 1:126 (2011), which is hereby incorporated by reference in its entirety).

Signal acquisition was carried out using a storage phosphor screen (GE Healthcare Life Sciences) at 200 μm resolution and ImageQuantTL software (GE Healthcare Life Sciences). Quantification was carried out with ImageJ (V2.0.0-rc-24/1.49 m). For $m^6A_m$ experiments, the $m^6A./A_m$ ratio was calculated. The use of this ratio has been described previously (Kruse et al., "A Novel Synthesis and Detection Method for Cap-Associated Adenosine Modifications in Mouse mRNA," *Sci. Rep.* 1:126 (2011), which is hereby incorporated by reference in its entirety). The assay was confirmed as being linear by spotting twice the sample material and confirming that the signal intensity doubles for the unmodified nucleotides (A, C, and U). Furthermore, exposure time of the TLC plates to the phosphor screen was chosen so that the signal was not saturated. For $m^6A$ quantification, $m^6A$ was calculated as a percentage of the total of the A, C, and U spots, as described previously (Jia et al., "N6-Methyladenosine in Nuclear RNA is a Major Substrate of the Obesity-Associated FTO," *Nat. Chem. Biol.* 7:885-887 (2011), which is hereby incorporated by reference in its entirety). The use of relative ratios for each individual sample is important since it reduces the error derived from possible differences in loading. To minimize the effects of culturing conditions on the measured $m^6A_m/A_m$ ratios of each experimental group (e.g., control versus knockdown), all replicates were processed in parallel to minimize any source of variability between samples being compared. Of note, the control conditions for siRNA transfection and plasmid transfection utilize different transfection reagents, which could affect baseline $m^6A_m/A_m$ ratios.

In Vitro Decapping Assays:

22-nucleotide-long RNA oligonucleotides that have an A, $A_m$, $m^6A$, or $m^6A_m$ at their 5' end were enzymatically capped with the vaccinia capping enzyme with [α-$^{32}$P]—$N^7$-methylguanosine triphosphate ($m^7GTP$) as previously described (Liu et al., "Analysis of mRNA Decapping," *Methods Enzymol.* 448:3-21 (2008), which is hereby incorporated by reference in its entirety). Decapping reactions were carried out according to Liu et al., "Analysis of mRNA Decapping," *Methods Enzymol.* 448:3-21 (2008), which is hereby incorporated by reference in its entirety. In brief, 10 nM recombinant DCP2 protein was incubated with the indicated cap-labelled RNAs in decapping buffer (10 mM Tris-HCl pH 7.5, 100 mM KCl, 2 mM $MgCl_2$, 2 mM DTT, 0.5 mM $MnCl_2$, 40 U $ml^{-1}$ recombinant RNase inhibitor) and incubated at 37° C. for 30 minutes. Reactions were stopped with 25 mM EDTA at the indicated time points. The identity of decapping products of the indicated modified cap adenosines subjected to 20 nM recombinant human DCP2 protein at 37° C. for 30 minutes were confirmed to be $m^7GDP$ by treatment with 0.5 U nucleoside diphosphate kinase ("NDPK") at 37° C. for 30 minutes in the presence of 0.5 mM ATP. A cap labelled RNA with a guanosine as the first nucleotide generated as previously described (Liu et al., "Analysis of mRNA Decapping," *Methods Enzymol.* 448:3-21 (2008), which is hereby incorporated by reference in its entirety) was used as a positive control. Decapping products were resolved by PEI-cellulose TLC plates (Sigma-Aldrich) and developed in 0.45 M $(NH_4)_2SO_4$ in a TLC chamber at room temperature. Reaction products were visualized and quantitated with a Molecular Dynamics PhosphorImager (Storm860) with ImageQuant-5 software.

Synthesis of mRNAs with Specific Forms of Methylated Caps:

To generate mRNAs that begin with either $m^7GpppA_m$ or $m^7Gpppm^6A_m$ thermostable TGK polymerase (Cozens et al., "A Short Adaptive Path from DNA to RNA Polymerases," *PNAS* 109:8067-8072 (2012), which is hereby incorporated by reference in its entirety), which enables RNA synthesis with an RNA primer from a DNA template, was used. The primers contained either $m^7GpppA_m$ or $m^7Gpppm^6A_m$ as the extended cap. The use of TGK polymerase and specific methylated forms of the primer ensures that all synthesized mRNAs begin with the desired extended cap structure. The DNA template for RNA synthesis was prepared by PCR using the pNL1.1 [Nluc] vector (Promega) as a template and Phusion High-Fidelity PCR Master Mix (NEB). Since the template needs to be single-stranded, a strategy of selectively degrading one of the strands of the PCR product was utilized. To achieve this, PCR was performed with a 5'-phosphorylated forward primer and a 5'-OH reverse primer. The undesired 5'-phosphorylated strand was digested with lambda exonuclease (Lucigen) (1 U per 1-2 μg double-stranded DNA) for 2 hours at 37° C. The digestion was stopped by phenol chloroform extraction and ethanol precipitation of the single-strand template.

RNA forward synthesis was performed from either an $m^7GpppA_m$ (20 nucleotide) or an $m^7Gpppm^6A_m$ (20 nucleotide) primer in a 50 μl reaction consisting of 1× Thermopol buffer (NEB) supplemented with 3 mM $MgSO_4$ and 2.5 mM NTP with a 1:1 primer/template ratio at 100 pmol each and 150 nM TGK polymerase. The primer extension was performed at two cycles of 10 s at 94° C., 1 minute at 50° C., and 1 hour at 65° C. After RNA synthesis, the template DNA strand was degraded using TURBO DNase (Thermo Fisher Scientific) and the capped nLuc mRNAs were purified with an RNeasy column (Qiagen). An approximately 250 nt poly(A) tail was added with A-Plus Poly(A) Polymerase Tailing Kit (Cellscript). The polyadenylated mRNAs were purified with oligo d(T)25 Magnetic Beads (NEB) according to the manufacturer's instructions.

Electroporation of mRNA:

Electroporation was used to deliver $m^7GpppA_m$-nLuc and $m^7Gpppm^6A_m$-nLuc mRNAs into HEK293T cells. HEK293T cells were trypsinized and resuspended in Ingenio Electroporation Solution (Minis) at $5\times10^6$ cells $ml^{-1}$. 100 μl of cell suspension was added to 2 μg of mRNA. Electroporation was carried out with Nucleofector II (Amaxa) using program Q-001. The cell suspension was immediately transferred to 37° C. pre-warmed growth medium supplemented with 5 mM $CaCl_2$ and 200 U $ml^{-1}$ micrococcal nuclease (Clontech). After a 15 minute incubation period at 37° C. to remove any residual extracellular RNA, cells were transferred to 24-well plates at $1.25\times10^5$ and incubated until adherent. Cells were then either collected immediately or after 2 hours of incubation for RNA extraction and quantification by qRT-PCR.

RNA Half-Life Measurement after Transcriptional Inhibition:

RNA half-lives after transcriptional inhibition were determined essentially as previously described (Wang et al., "N6-Methyladenosine-Dependent Regulation of Messenger RNA Stability," *Nature* 505:117-120 (2014) and Geula et al., "Stem Cells m6A mRNA Methylation Facilitates Resolution of Naive Pluripotency Toward Differentiation," *Science* 347:1002-1006 (2015), which are hereby incorporated by reference in their entirety). In brief, to achieve transcriptional inhibition for calculation of mRNA half-life, Flag- and NES-FTO-transfected HEK293T cells were either left untreated (that is, 0 h time point) or treated with actinomycin D (Sigma) for 6 hours at a final concentration of 5 μg ml$^{-1}$. Cells were then harvested for RNA isolation using TRIzol (Thermo Fisher Scientific). The total RNA derived from Flag- and NES-FTO-transfected HEK293T cells, was spiked-in with ERCC RNA controls (Ambion) before the isolation of mRNA and RNA-seq. Read count tables were generated using STAR aligner (Dobin et al., "STAR: Ultrafast Universal RNA-Seq Aligner," *Bioinformatics* 29:15-21 (2013), which is hereby incorporated by reference in its entirety). DESeq2 (Love et al., "Moderated Estimation of Fold Change and Dispersion for RNA-Seq Data With DESeq2," *Genome Biol.* 15:550 (2014), which is hereby incorporated by reference in its entirety) was used to calculate ERCC spike-in RNA size factors, which were then applied to normalize for library size changes in each replicate. As shown in FIG. 1C, the half-lives derived from the transcriptional inhibition experiments showed high correlation between independent replicates.

RNA Half-Life Measurements by 5-Bromouridine ("BrU") Pulse-Chase:

RNA half-life measurements by BrU pulse-chase was carried out essentially as described previously (Imamachi et al., "BRIC-Seq: A Genome-Wide Approach for Determining RNA Stability in Mammalian Cells," *Methods* 67:55-63 (2014), which is hereby incorporated by reference in its entirety). Briefly, HEK293T cells were pulsed with 150 μM 5-bromouridine (Santa Cruz Biotechnology) for 24 hours. Chase was initiated by changing to medium containing 1.5 mM uridine (Sigma) and cells were collected for RNA extraction after 6 and 16 hours. BrU-pulsed cells without uridine-chase were used as basal (0 h) controls. Total RNA was extracted with TRIzol reagent (Thermo Fisher Scientific) according to the manufacturer's instructions. Immunoprecipitation of BrU-labelled RNA from total RNA was carried out as previously described (Imamachi et al., "BRIC-Seq: A Genome-Wide Approach for Determining RNA Stability in Mammalian Cells," *Methods* 67:55-63 (2014), which is hereby incorporated by reference in its entirety). A BrU-labelled NanoLuc luciferase ("nLuc") RNA was generated by in vitro transcription as previously described (Imamachi et al., "BRIC-Seq: A Genome-Wide Approach for Determining RNA Stability in Mammalian Cells," *Methods* 67:55-63 (2014), which is hereby incorporated by reference in its entirety) and used as a spike-in immunoprecipitation control at 10 pgp per 1 μg input RNA.

Quantitative Real-Time PCR:

1-2 μg total RNA or 500 ng BrU-labelled RNA was reverse transcribed using the High Capacity cDNA Kit (Thermo Fisher Scientific) according to the manufacturer's instructions. The cDNA was subjected to quantitative real-time PCR analysis with the TaqMan Gene Expression Master Mix (Thermo Fisher Scientific) using Taqman Gene Expression Assays (Thermo Fisher Scientific) on a ViiA 7 Realtime-PCR System (Thermo Fisher Scientific). The following predesigned Taqman Gene expression assays were used in the study: FUCA1 (Hs00609173_m1), MAGOHB (Hs00970279_m1), PCNA(Hs00427214_g1), PCK1 (Hs01572978_g1), PSMD3 (Hs00160646_m1), SCFD2 (Hs00293797_m1).

ACTB (Hs01060665_g1) was used as a housekeeping gene to normalize the level of transfected nLuc mRNA. A custom probe and primer set was designed to detect nLuc cDNA (forward 5'-ATGTCGATCTTCAGCCCATTT-3' (SEQ ID NO: 16); reverse 5'-GGA GGTGTGTCCAGTTTGTT-3' (SEQ ID NO: 17); probe 5'-/56-FAM/ATCCAAAGGATTGTC CTGAGCGGT/ 3IABkFQ/-3' (SEQ ID NO: 18)). Amplification of nLuc cDNA was linear over seven orders of magnitude. The $2^{-\Delta\Delta c_t}$ method was used to calculate relative gene expression changes between time points and biological replicates.

m$^6$A Peak Enrichment Analyses:

m$^6$A peaks were based on previous MeRIP-seq analysis of Fto-knockout midbrain tissue (Hess et al., "The Fat Mass and Obesity Associated Gene (Fto) Regulates Activity of the Dopaminergic Midbrain Circuitry," *Nat. Neurosci.* 16:1042-1048 (2013), which is hereby incorporated by reference in its entirety). For analysis of m$^6$A peak distribution, m$^6$A peaks were individually binned based on their location within mRNA and mapped onto a virtual transcript in a metagene analysis to show their collective distribution within mRNA. Bin numbers were chosen such that each bin is on average 50 nucleotides long. Peak counts were smoothed using a spline function. Each peak was weighted by a coefficient corresponding to the number of MeRIP-seq reads in the immunoprecipitated samples relative to the reads obtained before immunoprecipitation. This peak mass value represents the enrichment of methylated mRNA at individual m$^6$A sites after immunoprecipitation and reflects the degree to which an mRNA is methylated at a particular m$^6$A site. To generate the peak height ratio plot, ratios between Fto-knockout peak mass over wild-type peak mass were used. The same bin numbers and sizes were used for all analyses.

Mapping and Validation of m$^6$A$_m$ Sites:

To further increase the number of miCLIP-based detection of m$^6$A$_m$ sites, the miCLIP pipeline was utilized (Linder et al., "Single-Nucleotide-Resolution Mapping of m6A and m6A$_m$ Throughout the Transcriptome," *Nat. Methods* 12:767-772 (2015), which is hereby incorporated by reference in its entirety) with the following modifications. Raw miCLIP reads were trimmed of their 3' adaptor and demultiplexed as previously described (Linder et al., "Single-Nucleotide-Resolution Mapping of m6A and m6Am Throughout the Transcriptome," Nat. Methods 12:767-772 (2015) and U.S. Patent Application Publication No. 2016/0060622, which are hereby incorporated by reference in their entirety). Then, PCR-duplicated reads of identical sequences were removed using the pyDuplicateRemover.py script of the pyCRAC tool suite (version 1.2.2.3). Unique reads were mapped with Bowtie (version 1.1.1) to hg19. Files of aligned reads were processed with samtools (version 1.2), bedtools (version 2.25.0), and custom bash commands to derive the 5' ends of each aligned read. 5'-end coordinates of the reads were then combined into 'piles' at each single nucleotide throughout the genome using the tag2cluster.pl script of the CIMS software package (Moore et al., "Mapping Argonaute and Conventional RNA-Binding Protein Interactions with RNA at Single-Nucleotide Resolution using HITS-CLIP and CIMS Analysis," *Nat. Protocols* 9:263-293 (2014), which is hereby incorporated by reference in its entirety) (parameters: -v -s -maxgap "-1"). Piles were then filtered to contain at least five 5' ends at a single nucleotide. Adjacent piles (zero nucleotides apart) were clustered together using a custom perl script. The resulting clusters were annotated with their transcript ID and transcript region (5' UTR, CDS, or 3' UTR) using a custom perl script and custom bash commands. After annotation, clusters were filtered for those found in the 5' UTR of annotated mRNAs. To remove noise, clusters with a width of one nucleotide were removed using custom bash commands. Finally, custom bash commands were used to filter for clusters found only at the very beginning of 5' UTRs.

To verify that these are indeed $m^6A_m$ residues, applicant took advantage of fact that $m^6A_m$ occurs only at transcription start sites ("TSS"). Thus, the known TSS and transcription initiation sequences were compared around each $m^6A_m$-containing region. To identify genome-wide positions of the TSS from published CAGE-seq datasets (Forrest et al., "A Promoter-Level Mammalian Expression Atlas," Nature 507: 462-470 (2014), which is hereby incorporated by reference in its entirety) and genome-wide positions of the consensus initiator motif, YYANW (Y=C or T; N=A, C, G, or T; W=A or T) (Xi et al., "Analysis of Overrepresented Motifs in Human Core Promoters Reveals Dual Regulatory Roles of YY1," Genome Res 17:798-806 (2007), which is hereby incorporated by reference in its entirety), a custom perl script was used. The CAGE sites in this data set are combined from RLE (relative log expression)-normalized robust CAGE-seq analysis of multiple cell lines and tissues, and therefore provide high sensitivity for detecting transcription start sites.

Next, the distribution of TSS or the YYANW sequence around $m^6A_m$-containing regions was determined. To do so, the 'closest' tool of the bedtools suite was used to determine distances between each $m^6A_m$-containing region and the nearest TSS or YYANW sequence. The following commands were used to find TSS or YYANW sequences nearest to the 5'-most nucleotide of each $m^6A_m$-containing region.

To measure the distance of TSS or YYANW sequences that overlap with $m^6A_m$-containing regions: bedtools closest -a m6Am.reference.points.bed -b feature.locations.bed -s>m6Am. distance.overlap.bed.

To measure the distance of TSS or YYANW sequences that do not overlap with $m^6A_m$-containing regions: bedtools closest -a m6Am.reference.points.bed -b TSS.locations.bed -s -io>m6Am.feature.distance.bed.

The total distributions of the distances of TSS or YYANW sequences to $m^6A_m$-containing regions (regardless of overlap) were then plotted as a histogram.

These results demonstrated that TSS and the YYANW core initiator sequence are highly clustered at $m^6A_m$-containing regions. This suggests that the called $m^6A_m$-containing regions reflect true transcription initiation sites. All newly identified $m^6A_m$ mRNAs are listed in Table 2 together with CAGE and initiator overlap. Notably, $m^6A_m$ sites are distinct from the recently described 5' UTR $m^6A$ sites (Meyer et al., "5' UTR m6A Promotes Cap-Independent Translation," Cell 163:999-1010 (2015), which is hereby incorporated by reference in its entirety) since they are found in a different sequence context and overlap with transcription start sites (Linder et al., "Single-Nucleotide-Resolution Mapping of m6A and m6Am Throughout the Transcriptome," Nat. Methods 12:767-772 (2015), which are hereby incorporated by reference in its entirety). Furthermore, the previously described ex vivo m'A to $m^6A$ conversion is unlikely to generate artefacts during $m^6A$ mapping. m'A to $m^6A$ conversion requires extreme conditions (Dominissini et al., "The Dynamic N1-Methyladenosine Methylome in Eukaryotic Messenger RNA," Nature 530:441-446 (2016), which is hereby incorporated by reference in its entirety) that are not used in miCLIP or MeRIP-seq. Additionally, $m^6A$ peaks are not detected at the annotated $m^1A$ site in the 28S rRNA (Linder et al., "Single-Nucleotide-Resolution Mapping of m6A and m6Am Throughout the Transcriptome," Nat. Methods 12:767-772 (2015), which is hereby incorporated by reference in its entirety), indicating that no detectable $m^1A$ to $m^6A$ conversion is occurring during miCLIP.

TABLE 2

Exemplary Newly Identified m6Am mRNAs

| chrom | start | end | strand | refseq_mrna | gene_symbol | position | region | width | cage_overlap | yyanw_overlap |
|---|---|---|---|---|---|---|---|---|---|---|
| chr1 | 894659 | 894663 | - | NM_015658 | NOC2L | 21 | 5utr | 4 | no | yes |
| chr1 | 935501 | 935504 | - | NM_001142467 | HES4 | 52 | 5utr | 3 | yes | no |
| chr1 | 1167360 | 1167363 | - | NM_016176 | SDF4 | 88 | 5utr | 3 | yes | yes |
| chr1 | 1209211 | 1209214 | - | NM_194457 | UBE2J2 | 24 | 5utr | 3 | yes | yes |
| chr1 | 1260031 | 1260033 | - | NM_001256456 | CPSF3L | 37 | 5utr | 2 | yes | yes |
| chr1 | 1310578 | 1310580 | - | NM_001127229 | AURKAIP1 | 3 | 5utr | 2 | yes | yes |
| chr1 | 1310587 | 1310590 | - | NM_017900 | AURKAIP1 | 232 | 5utr | 3 | yes | yes |
| chr1 | 1334714 | 1334716 | - | NM_001039577 | CCNL2 | 5 | 5utr | 2 | yes | yes |
| chr1 | 1342677 | 1342679 | - | NM_017971 | MRPL20 | 17 | 5utr | 2 | yes | yes |
| chr1 | 1407214 | 1407216 | + | NM_031921 | ATAD3B | 53 | 5utr | 2 | no | no |
| chr1 | 1447540 | 1447544 | + | NM_018188 | ATAD3A | 22 | 5utr | 4 | yes | yes |
| chr1 | 1510009 | 1510011 | - | NM_014188 | SSU72 | 254 | 5utr | 2 | yes | yes |
| chr1 | 1624093 | 1624095 | - | NM_001290264 | SLC35E2B | 151 | 5utr | 2 | no | no |
| chr1 | 1677368 | 1677370 | - | NM_001199787 | SLC35E2 | 71 | 5utr | 2 | no | no |
| chr1 | 1770668 | 1770673 | - | NM_001282538 | GNB1 | 308 | 5utr | 5 | yes | no |
| chr1 | 1822508 | 1822510 | - | NM_001282539 | GNB1 | 49 | 5utr | 2 | yes | yes |
| chr1 | 2126209 | 2126211 | - | NM_001282673 | FAAP20 | 6 | 5utr | 2 | yes | no |

TABLE 2-continued

Exemplary Newly Identified m6Am mRNAs

| chrom | start | end | strand | refseq_mrna | gene_symbol | position | region | width | cage_overlap | yyanw_overlap |
|---|---|---|---|---|---|---|---|---|---|---|
| chr1 | 2458034 | 2458036 | - | NM_018216 | PANK4 | 2 | 5utr | 2 | yes | yes |
| chr1 | 3713053 | 3713055 | - | NM_020710 | LRRC47 | 16 | 5utr | 2 | yes | yes |
| chr1 | 3773774 | 3773777 | - | NM_014704 | CEP104 | 24 | 5utr | 3 | yes | yes |
| chr1 | 6259668 | 6259670 | - | NM_000983 | RPL22 | 12 | 5utr | 2 | yes | yes |
| chr1 | 6453819 | 6453821 | - | NM_007274 | ACOT7 | 8 | 5utr | 2 | yes | yes |
| chr1 | 6685245 | 6685247 | + | NM_001195752 | THAP3 | 38 | 5utr | 2 | yes | yes |
| chr1 | 7831359 | 7831361 | + | NM_004781 | VAMP3 | 33 | 5utr | 2 | yes | yes |
| chr1 | 8021721 | 8021728 | + | NM_001123377 | PARK7 | 15 | 5utr | 7 | yes | yes |
| chr1 | 8021801 | 8021803 | + | NM_007262 | PARK7 | 90 | 5utr | 2 | no | yes |
| chr1 | 8938763 | 8938780 | - | NM_001428 | ENO1 | 389 | 5utr | 17 | yes | yes |
| chr1 | 9884020 | 9884024 | - | NM_001009566 | CLSTN1 | 531 | 5utr | 4 | yes | yes |
| chr1 | 10002814 | 10002816 | - | NM_032368 | LZIC | 13 | 5utr | 2 | no | yes |
| chr1 | 10093216 | 10093218 | + | NM_006048 | UBE4B | 178 | 5utr | 2 | yes | no |
| chr1 | 10459092 | 10459094 | + | NM_002631 | PGD | 10 | 5utr | 2 | no | yes |
| chr1 | 10490518 | 10490520 | + | NM_199006 | APITDI-CORT | 362 | 5utr | 2 | yes | yes |
| chr1 | 10532550 | 10532552 | - | NM_213566 | DFFA | 64 | 5utr | 2 | yes | yes |
| chr1 | 11072709 | 11072719 | + | NM_007375 | TARDBP | 41 | 5utr | 10 | yes | no |
| chr1 | 11120038 | 11120040 | - | NM_003132 | SRM | 54 | 5utr | 2 | yes | yes |
| chr1 | 11741203 | 11741205 | - | NM_006341 | MAD2L2 | 69 | 5utr | 2 | yes | yes |
| chr1 | 11796192 | 11796194 | + | NM_001040196 | AGTRAP | 53 | 5utr | 2 | yes | yes |
| chr1 | 12040501 | 12040503 | + | NM_014874 | MFN2 | 266 | 5utr | 2 | yes | yes |
| chr1 | 12908302 | 12908306 | - | NM_001013631 | HNRNPCL1 | 67 | 5utr | 4 | yes | no |

At present, it is not possible to determine the absolute stoichiometry of $m^6A_m$ or $A_m$ at the first position of mRNA at a transcriptome-wide level. Conceivably, if the stoichiometry of $m^6A_m$ is not 100% on a specific $m^6A_m$-classified mRNA, the effect of $m^6A_m$ may be underestimated. For experiments using BrU pulse-chase labelling, applicant sought to examine mRNAs with high stoichiometry $m^6A_m$. As a surrogate for stoichiometry, the miCLIP/RNA-seq ratio was measured in a 20 nucleotide window surrounding the 5' $m^6A_m$ region using bedtools coverage. For qRT-PCR analysis in the BrU pulse-chase experiments examining individual mRNA half-life changes upon NES-FTO expression, $m^6A_m$ mRNAs with high miCLIP/RNA-seq ratio were chosen (Table 3).

TABLE 3 miCLIP/RNA-Seq Ratio of Exemplary mRNAs

| refseq_mrna | hgnc_symbol | miclip_normalized | input_normalized | rel_stoic | group |
|---|---|---|---|---|---|
| NM_000019 | ACAT1 | 36.8253 | 39.4946 | 0.932413545 | low |
| NM_000026 | ADSL | 41.8065 | 34.8088 | 1.201032498 | medium |
| NM_000034 | ALDOA | 30.0651 | 8.7022 | 3.454884972 | high |
| NM_000071 | CBS | 12.6309 | 48.1968 | 0.262069266 | low |
| NM_000075 | CDK4 | 14.0541 | 8.0328 | 1.749589184 | medium |
| NM_000097 | CPOX | 22.7712 | 18.7432 | 1.214604605 | medium |
| NM_000098 | CPT2 | 9.9624 | 3.347 | 2.976516283 | medium |

TABLE 3-continued miCLIP/RNA-Seq Ratio of Exemplary mRNAs

| refseq_mrna | hgnc_symbol | miclip_normalized | input_normalized | rel_stoic | group |
|---|---|---|---|---|---|
| NM_000100 | CSTB | 12.0972 | 7.3634 | 1.642882364 | medium |
| NM_000101 | CYBA | 88.7721 | 27.4454 | 3.234498313 | medium |
| NM_000107 | DDB2 | 13.3425 | 12.0492 | 1.107334927 | medium |
| NM_000117 | EMD | 10.1403 | 26.1066 | 0.38841902 | low |
| NM_000122 | ERCC3 | 10.4961 | 4.6858 | 2.239980366 | medium |
| NM_000127 | EXT1 | 7.116 | 5.3552 | 1.328801912 | medium |
| NM_000143 | FH | 28.8198 | 8.0328 | 3.587765163 | high |
| NM_000146 | FTL | 24.7281 | 53.552 | 0.461758664 | low |
| NM_000158 | GBE1 | 3.0243 | 0.6694 | 4.517926501 | high |
| NM_000169 | GLA | 40.0275 | 14.7268 | 2.718003911 | medium |
| NM_000175 | GPI | 4.8033 | 2.0082 | 2.391843442 | medium |
| NM_000182 | HADHA | 13.8762 | 6.694 | 2.072930983 | medium |
| NM_000189 | HK2 | 14.232 | 5.3552 | 2.657603824 | medium |
| NM_000191 | HMGCL | 13.8762 | 4.0164 | 3.454884972 | high |
| NM_000194 | HPRT1 | 15.2994 | 20.7514 | 0.737270738 | low |
| NM_000262 | NAGA | 9.2508 | 2.0082 | 4.606513295 | high |
| NM_000263 | NAGLU | 7.6497 | 6.694 | 1.142769644 | medium |
| NM_000270 | PNP | 13.5204 | 11.3798 | 1.188105239 | medium |
| NM_000281 | PCBD1 | 6.4044 | 6.0246 | 1.06304153 | medium |
| NM_000286 | PEX12 | 6.9381 | 1.3388 | 5.182327457 | high |
| NM_000289 | PFKM | 9.0729 | 0.6694 | 13.5537795 | high |
| NM_000291 | PGK1 | 12.6309 | 6.694 | 1.886898715 | medium |
| NM_000294 | PHKG2 | 9.0729 | 6.694 | 1.35537795 | medium |
| NM_000320 | QDPR | 10.674 | 2.6776 | 3.986405736 | high |
| NM_000321 | RB1 | 8.3613 | 2.6776 | 3.122684494 | medium |
| NM_000367 | TPMT | 19.569 | 12.0492 | 1.624091226 | medium |

Classification of mRNAs Based on the First Nucleotide:

In experiments where $m^6A_m$-initiated mRNAs was compared to $A_m$-, $C_m$-, $G_m$-, and $U_m$-initiated mRNAs, the mRNAs were classified based on the nucleotide at the annotated TSS. Annotated TSS were extracted from the Ensembl BioMart database (Smedley et al., "The BioMart Community Portal: An Innovative Alternative to Large, Centralized Data Repositories," *Nucleic Acids Res.* 43(W1): W589-W598 (2015), which is hereby incorporated by reference in its entirety). A list of exemplary transcripts with their respective annotated transcription start site is found in Table 4.

TABLE 4

Exemplary mRNA Transcripts and Transcription Start Sites

| refseq_mrna | annotated_starting_nt | refseq_mrna | annotated_starting_nt | refseq_mrna | annotated_starting_nt |
|---|---|---|---|---|---|
| NM_000014 | U | NM_000047 | A | NM_000082 | C |
| NM_000015 | U | NM_000048 | G | NM_000083 | A |
| NM_000017 | A | NM_000049 | U | NM_000084 | C |

TABLE 4-continued

Exemplary mRNA Transcripts and Transcription Start Sites

| refseq_mrna | annotated_starting_nt | refseq_mrna | annotated_starting_nt | refseq_mrna | annotated_starting_nt |
|---|---|---|---|---|---|
| NM_000018 | A | NM_000050 | G | NM_000085 | A |
| NM_000019 | m6Am | NM_000051 | C | NM_000087 | A |
| NM_000020 | A | NM_000053 | A | NM_000088 | A |
| NM_000021 | A | NM_000054 | C | NM_000089 | G |
| NM_000022 | C | NM_000055 | C | NM_000090 | G |
| NM_000023 | C | NM_000056 | A | NM_000091 | G |
| NM_000024 | G | NM_000057 | A | NM_000092 | U |
| NM_000025 | C | NM_000059 | G | NM_000093 | C |
| NM_000026 | m6Am | NM_000061 | U | NM_000094 | C |
| NM_000027 | U | NM_000062 | C | NM_000095 | U |
| NM_000028 | C | NM_000064 | U | NM_000097 | m6Am |
| NM_000029 | U | NM_000065 | U | NM_000098 | m6Am |
| NM_000030 | C | NM_000066 | U | NM_000100 | m6Am |
| NM_000031 | C | NM_000067 | C | NM_000101 | m6Am |
| NM_000032 | U | NM_000068 | C | NM_000102 | U |
| NM_000033 | G | NM_000069 | A | NM_000103 | C |
| NM_000034 | m6Am | NM_000070 | C | NM_000104 | U |
| NM_000035 | U | NM_000071 | m6Am | NM_000106 | C |
| NM_000036 | U | NM_000072 | C | NM_000107 | m6Am |
| NM_000037 | U | NM_000073 | A | NM_000108 | A |
| NM_000038 | G | NM_000074 | A | NM_000109 | G |
| NM_000039 | G | NM_000075 | m6Am | NM_000110 | C |
| NM_000040 | U | NM_000076 | U | NM_000111 | U |
| NM_000041 | G | NM_000077 | G | NM_000112 | G |
| NM_000042 | C | NM_000078 | A | NM_000113 | C |
| NM_000043 | A | NM_000079 | U | NM_000115 | U |
| NM_000045 | G | NM_000080 | G | NM_000116 | G |
| NM_000046 | U | NM_000081 | C | NM_000117 | m6Am |

Metagene Analysis Using miCLIP Reads:

For FIGS. 1F-1G, a high-coverage m6A individual-nucleotide-resolution cross-linking and immunoprecipitation ("miCLIP") data set in HEK293T cells was generated (Linder et al., "Single-Nucleotide-Resolution Mapping of m6A and m6Am Throughout the Transcriptome," Nat. Methods 12:767-772 (2015), which are hereby incorporated by reference in its entirety). Metagenes were constructed for the miCLIP-identified unique 6 mA reads using an in-house peri annotation pipeline and custom R scripts. Briefly, the 6 mA reads were mapped to different RNA features (5' UTR, CDS, and 3' UTR) of the human genome (hg19). Position of the reads was normalized to the median feature length of the RNAs to which the tag mapped. A frequency distribution plot was generated by counting number of reads in contiguous bins on a virtual mRNA transcript, whose feature lengths represent the median feature lengths of RNAs under analysis either of each individual sample or of the control sample. A kernel density (Gaussian) estimate was plotted.

RNA-SEQ Analysis:

To avoid potential clonal variation, $10^6$ cells from each of the three DCP2 CRISPR lines were pooled together (referred to as DCP2-knockout cells), passaged once, and immediately used for RNA-seq. The DCP2 CRISPR line RNA samples were subject to depletion of ribosomal RNA using RiboMinus Eukaryote System v. 2 (Life Technologies), followed by cDNA library preparation using the Illumina TruSeq RNA Sample Preparation Kit v.2. The sequencing (2×100-bp paired-end) was performed by RUCDR Infinite Biologics (Piscataway) using the Illumina Hiseq 2500 according to the manufacturer's protocol. Two independent biological replicates were sequenced for each condition. The RNA-seq library for miCLIP normalization was prepared using a cloning strategy parallel to the one used in miCLIP (Linder et al., "Single-Nucleotide-Resolution Mapping of m6A and m6Am Throughout the Transcriptome," *Nat. Methods* 12:767-772 (2015) and Heyer et al., "An Optimized Kit-Free Method for Making Strand-Specific Deep Sequencing Libraries From RNA Fragments," *Nucleic Acids Res.* 43:e2 (2015), which are hereby incorporated by reference in their entirety).

For all other RNA-seq analyses, total RNA was diluted to a concentration of 50 ng $\mu l^{-1}$ and submitted to the Weill Cornell Medicine Epigenomics Core for isolation of mRNA and library preparation using the Illumina TruSeq Stranded mRNA Library Prep Kit (RS-122-2101, Illumina). The libraries were sequenced on the Illumina HiSeq 2500 instrument, in either single-read or paired-end mode, with 50-100 bases per read. At least two independent biological replicates were sequenced for each condition.

Gene expression was measured using STAR (Dobin et al., "STAR: Ultrafast Universal RNA-Seq Aligner," *Bioinformatics* 29:15-21 (2013), which is hereby incorporated by reference in its entirety) read counts (version 2.4.1; -quantMode TranscriptomeSAM GeneCounts), which were processed with either the DESeq2 pipeline[43] (version 1.8.1) or the RSEM pipeline[50] (version 1.2.25). Analysis and visualization of RNA-seq datasets was carried out with custom in-house-generated R scripts using RStudio (Version 0.99.489). Only transcripts with normalized read counts >1 were included in the analyses.

Figure 2:
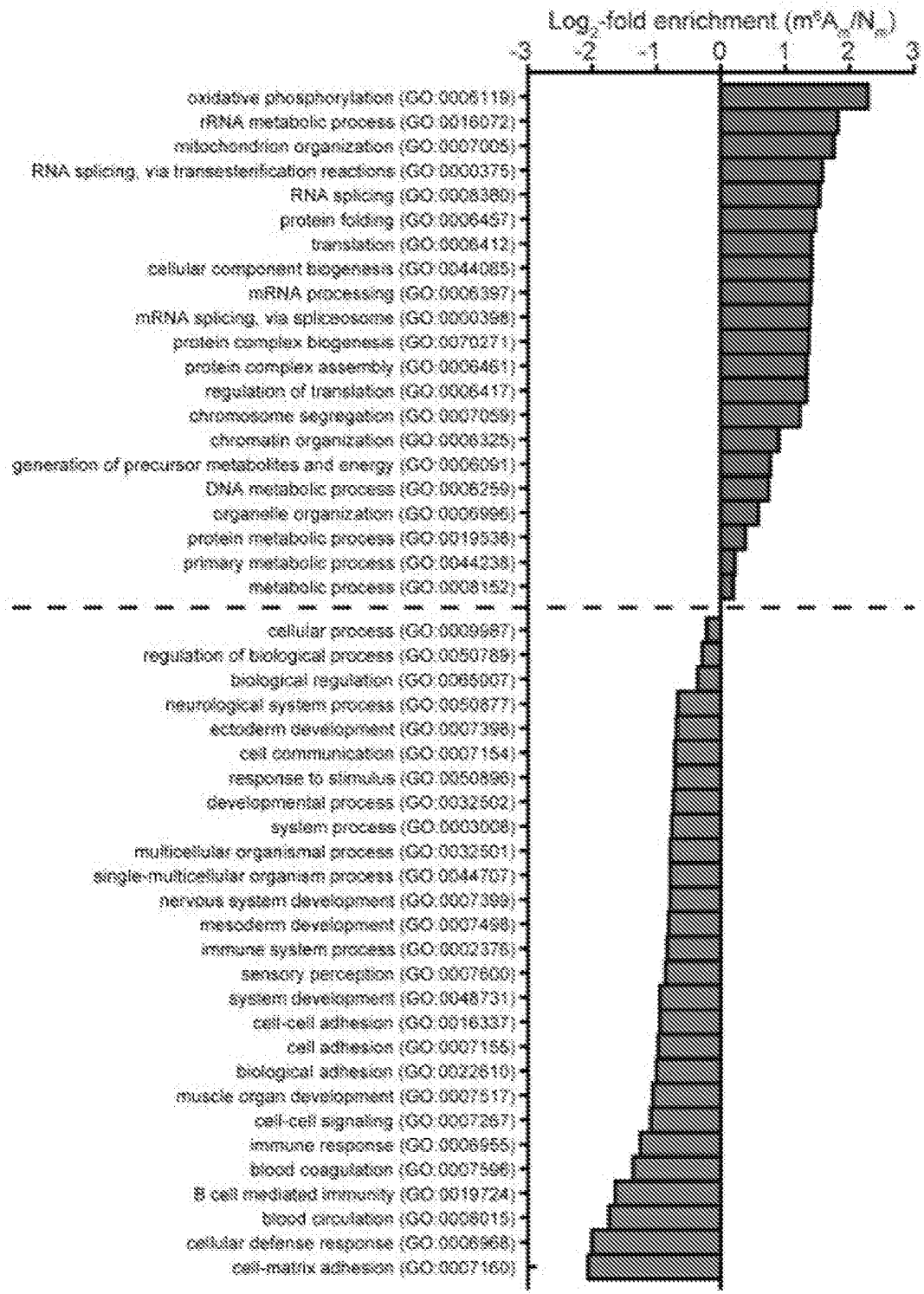
FIG. 2 is a graph showing Gene Ontology ("GO") analysis of m⁶A$_m$ mRNAs, which illustrates that m⁶A$_m$-containing mRNAs are enriched for oxidative phosphorylation, metabolic pathways, and components of the RNA processing machinery. A PANTHER overrepresentation test and Bonferroni correction with a P value threshold of <0.01 were used. All annotated non-m⁶A$_m$-containing mRNAs ("N$_m$") were used as the background gene list. m⁶A$_m$ mRNAs are overrepresented in cellular pathways associated with oxidative phosphorylation and metabolism as well as mRNA processing and translation, suggesting that m⁶A$_m$ controls cellular pathways by stabilizing specific populations of mRNAs.

Previously published RNA-seq datasets used in the current study were extracted from Gene Expression Omnibus (GEO, NCBI) and, if no processed data was available, the fastq files were reanalyzed with the pipelines described above. mRNA half-life data was either calculated based on the decay rates derived from a HEK293T cell data set or was extracted from previously published half-life data sets in HeLa cells (Wang et al., "N6-Methyladenosine-Dependent Regulation of Messenger RNA Stability," *Nature* 505:117-120 (2014), which is hereby incorporated by reference in its entirety). Only mRNAs with a half-life between 0 hours and 25 hours were used in the analysis of mRNA half-life based on the identity of the first encoded nucleotide. For classification of short- and long-lived mRNAs, half-life values were divided into quartiles. mRNAs in the lowest quartile (0-3 hours) were defined as short-lived, whereas mRNAs in the highest quartile (10-24 hours) were defined as long-lived. The analysis of DICER- and AGO2-knockdown effects on $m^6A_m$ mRNAs was performed using previously published datasets (Rehwinkel et al., "A Crucial Role for GW182 and the DCP1:DCP2 Decapping Complex in miRNA-Mediated Gene Silencing," *RNA* 11:1640-1647 (2005), which is hereby incorporated by reference in its entirety). $m^6A_m$ mapped in mouse liver (Linder et al., "Single-Nucleotide-Resolution Mapping of m6A and m6Am Throughout the Transcriptome," *Nat. Methods* 12:767-772 (2015), which is hereby incorporated by reference in its entirety) was used in order to correspond with the mouse liver expression analysis in these datasets. When indicated, the analysis was limited to mRNAs with TargetScan-predicted microRNA-binding sites and a context score cut-off ≤0.1 (Grimson et al., "MicroRNA Targeting Specificity in Mammals: Determinants Beyond Seed Pairing," *Mol. Cell* 27:91-105 (2007), which is hereby incorporated by reference in its entirety). Non-target mRNAs in FIG. 2F were filtered for mRNAs that contain 3' UTR sizes ≤300 nt to reduce the likelihood of analyzing mRNAs with alternative 3' UTRs or alternative polyadenylation sites. The analysis of the effect of single microRNA transfection on $m^6A_m$mRNAs was performed using previously published datasets of miR-155 duplex transfected HeLa cells (Schmitter et al., "Effects of Dicer and Argonaute Down-Regulation on mRNA Levels in Human HEK293 cells," *Nucleic Acids Res.* 34:4801-4815 (2006), which is hereby incorporated by reference in its entirety). In these experiments, the analysis was limited to CLIP-supported microRNA-mRNAs interactions according to starBase v.2.0 (Yang et al., "starBase: A Database for Exploring MicroRNA-mRNA Interaction Maps From Argonaute CLIP-Seq and Degradome-Seq Data," *Nucleic Acids Res.* 39:D202-D209 (2011), which is hereby incorporated by reference in its entirety).

Ribosome Profiling:

To determine if $m^6A_m$ is associated with changes in translation efficiency, a previously published ribosome profiling dataset was analyzed (Iwasaki et al., "Rocaglates Convert DEAD-Box Protein eIF4A Into a Sequence-Selective Translational Repressor," *Nature* 534:558-561 (2016), which is hereby incorporated by reference in its entirety). Ribosome footprint reads and corresponding RNA-seq reads were processed essentially as described (Ingolia et al., "The Ribosome Profiling Strategy for Monitoring Translation In Vivo by Deep Sequencing of Ribosome-Protected mRNA Fragments," *Nat. Protocols* 7:1534-1550 (2012), which is hereby incorporated by reference in its entirety). First, adaptors were trimmed using Flexbar v.2.5. For ribosome footprints, only reads from which the adaptor was trimmed were retained. Reads mapping to ribosomal RNAs were removed with bowtie v.1.1.2. Remaining reads were then aligned to the hg19 genome with STAR v.2.5.2a in a splicing-aware manner and using UCSC refSeq as a transcript model database (version from 2 Jun. 2014 downloaded from Illumina iGenomes). Two mismatches were allowed and only unique alignments were reported. Aligned reads were then counted on transcript regions using custom R scripts considering only transcripts with annotated 5' and 3' UTRs. Translation efficiency was calculated as previously described (Schmitter et al., "Effects of Dicer and Argonaute Down-Regulation on mRNA Levels in Human HEK293 cells," *Nucleic Acids Res.* 34:4801-4815 (2006), which is hereby incorporated by reference in its entirety), with pre-filtering for transcripts that had at least ten counted reads.

Statistics and Software:

P values were calculated with a two-tailed unpaired Student's t-test or, for the comparison of more than two groups, with a one- or two-way ANOVA followed by Bonferroni's or Tukey's post hoc test. Reproducibility of half-life and translation efficiency measurements was assessed by calculating the Pearson correlation coefficient between replicates. The influence of covariates on the effect of $m^6A_m$-containing mRNAs compared to non-$m^6A_m$ mRNAs on mRNA half-life was studied by ANCOVA analysis using SPSS Statistics software (IBM, v.22). The covariates include the number of mRNA-destabilizing AU-rich, GU-rich and U-rich elements (Fallmann et al., "AREsite2: An Enhanced Database for the Comprehensive Investigation of AU/GU/U-Rich Elements," *Nucleic Acids Res.* 44(D1):D90-D95 (2016), which is hereby incorporated by reference in its entirety), gene expression (log 2[FPKM], FPKM>1), translation efficiency ($\log_2$[TE], TE>0), GC composition and length of 5' and 3' UTR, number of exons in 5' and 3' UTRs, number of conserved miRNA target sites ($P_{CT}$>0) (Friedman et al., "Most Mammalian mRNAs are Conserved Targets of MicroRNAs," *Genome Res.* 19:92-105

(2009), which is hereby incorporated by reference in its entirety), minimum-free energy to length ratio (Lorenz et al., "ViennaRNA Package 2.0. Algorithms," *Mol. Biol.* 6:26 (2011), which is hereby incorporated by reference in its entirety), and the number of G-quadruplexes in the 5' UTR (Huppert et al., "G-quadruplexes: The Beginning and End of UTRs," *Nucleic Acids Res.* 36:6260-6268 (2008) and Beaudoin & Perreault, "5'-UTR G-Quadruplex Structures Acting as Translational Repressors," *Nucleic Acids Res.* 38:7022-7036 (2010), which are hereby incorporated by reference in their entirety). GC composition, UTR lengths, and the number of exons were calculated from refseq mRNA annotations (hg19) from the UCSC Genome browser. P values of 0.05 or less were considered significant. Initial reaction velocities for enzyme kinetics were analyzed by nonlinear regression curve-fitting using Graphpad Prism software (version 5.0f) to obtain $k_{cat}$, $K_m$ and $V_m$. Gene Ontology ("GO") functional annotation was performed using PANTHER Overrepresentation Test (release 20150430) and Bonferroni correction with a P value threshold of <0.01. Non-$m^6A_m$-containing mRNAs were used as the background gene list.

Data Availability:

Sequencing data that support the findings of this study have been deposited in the GEO database under accession number GSE78040.

Example 1—FTO Targets Methyladenine at Transcription Start Sites

Figures 3A, 3B, 3C, 3D, 3E, 3F, 3G:
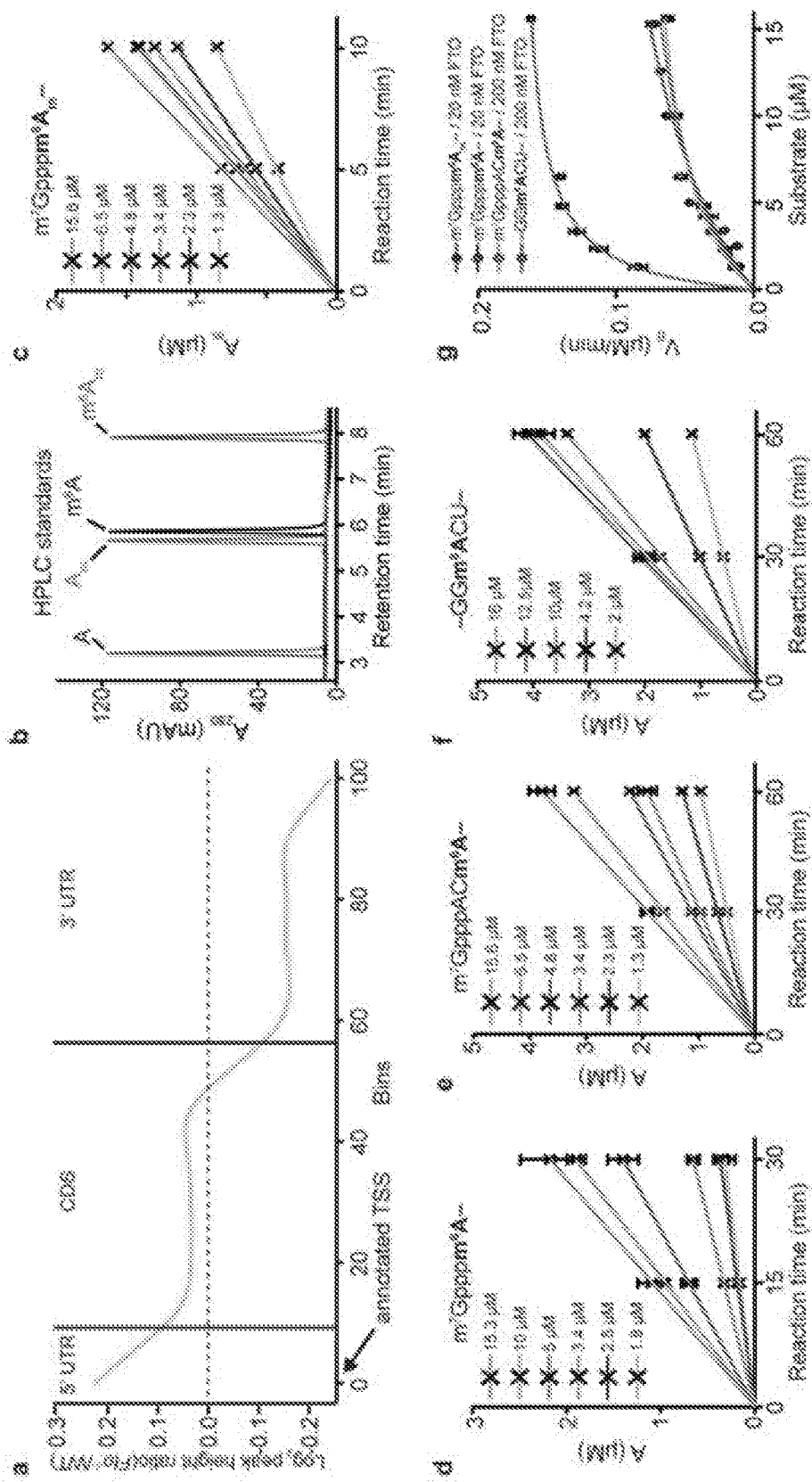
FIGS. 3A-3G show that rd'A enrichment is increased within the 5' UTR of Fto-knockout mice relative to wild-type mice and that FTO prefers m⁶A$_m$ over m⁶A. In the graph of FIG. 3A, m⁶A peak mass was calculated for all peaks that were found in both Fto-knockout mice ("Fto⁻/⁻") and wild-type ("WT") mice. The ratio of each individual peak's mass relative to the average peak mass for each sample was then determined, providing a relative peak mass. The relative peak mass for Fto⁻/⁻ mice was divided by the relative peak mass for wild-type mice for each m⁶A peak. A metagene analysis was performed to plot the distribution of these peak mass ratios (knockout/wild type) along the length of an mRNA. This analysis reveals that the changes in peak mass ratio for knockout mice relative to wild-type mice are increased in the 5' UTR. These findings provided the first hint that FTO activity might be directed towards m⁶A$_m$. The basis for the reduced peak mass ratio in the 3' UTR is unclear. Because FTO is a demethylating enzyme, loss of FTC) should increase nucleotide methylation. Thus, the reduced methylation of m$^6$A residues in the 3' UTR is likely to be an indirect effect of FTC) deficiency. CDS, coding sequence; TSS, transcription start site.

FTO exhibits demethylation activity towards $m^6A$ in assays performed in vitro (Jia et al., "N6-Methyladenosine in Nuclear RNA is a Major Substrate of the Obesity-Associated FTO," *Nat. Chem. Biol.* 7:885-887 (2011), which is hereby incorporated by reference in its entirety). However, it was previously observed that most $m^6A$ residues are unaffected in FTO-deficient mice (Hess et al., "The Fat Mass and Obesity Associated Gene (Fto) Regulates Activity of the Dopaminergic Midbrain Circuitry," *Nat. Neurosci.* 16:1042-1048 (2013), which is hereby incorporated by reference in its entirety). Only a few $m^6A$ residues showed increased abundance based on transcriptome-wide mapping using antibodies directed against $N^6$-methyladenine ("6 mA") (Hess et al., "The Fat Mass and Obesity Associated Gene (Fto) Regulates Activity of the Dopaminergic Midbrain Circuitry," *Nat. Neurosci.* 16:1042-1048 (2013), which is hereby incorporated by reference in its entirety). To understand this selectivity, it was investigated whether FTO demethylates $m^6A$ residues based on their position within mRNAs. The change in $m^6A$ stoichiometry for each $m^6A$ peak mapped in the Fto-knockout was measured relative to the wild-type transcriptome. A previously described stoichiometry measurement in which the number of $m^6A$-containing RNA fragments at each peak is normalized to transcript abundance was utilized (Meyer et al., "Comprehensive Analysis of mRNA Methylation Reveals Enrichment in 3' UTRs and Near Stop Codons," *Cell* 149:1635-1646 (2012), which is hereby incorporated by reference in its entirety). Notably, the $m^6A$ stoichiometry in the Fto-knockout transcriptome was increased for $m^6A$ residues closer to the 5' end of the transcript (FIG. 3A).

Antibodies used in these early $m^6A$ mapping studies were recently shown to bind both $m^6A$ and $m^6A_m$ (Linder et al., "Single-Nucleotide-Resolution Mapping of m6A and m6Am Throughout the Transcriptome," *Nat. Methods* 12:767-772 (2015), which are hereby incorporated by reference in its entirety). These two nucleotides are found in mRNA and both contain the 6 mA base (Wei et al., "N6, O2'-Dimethyladenosine a Novel Methylated Ribonucleoside Next to the 5' Terminal of Animal Cell and Virus mRNAs," *Nature* 257:251-253 (1975), which is hereby incorporated by reference in its entirety). As a result, early transcriptome-wide mapping studies of $m^6A$ also contain misannotated peaks that are instead derived from $m^6A_m$ (Linder et al., "Single-Nucleotide-Resolution Mapping of m6A and m6Am Throughout the Transcriptome," *Nat. Methods* 12:767-772 (2015), which are hereby incorporated by reference in its entirety).

The distribution of FTO-regulated peaks in the 5' untranslated region (UTR) is reminiscent of transcription start sites in mRNA (FIG. 3A), which are often marked by $m^6A_m$ (Linder et al., "Single-Nucleotide-Resolution Mapping of m6A and m6Am Throughout the Transcriptome," *Nat. Methods* 12:767-772 (2015), which are hereby incorporated by reference in its entirety). Recent single-nucleotide-resolution map of $m^6A_m$ showed that $m^6A_m$ and transcription start sites overlap in mRNA (Linder et al., "Single-Nucleotide-Resolution Mapping of m6A and m6Am Throughout the Transcriptome," *Nat. Methods* 12:767-772 (2015), which are hereby incorporated by reference in its entirety). This pattern of transcription start sites occurs because many mRNAs can be initiated at multiple positions downstream of the annotated start site. Thus, it was hypothesized that the FTO-regulated peaks reflect $m^6A_m$ rather than $m^6A$.

Example 2—FTO Demethylates $m^6A_m$ in a $m^7G$ Cap-Dependent Manner

Figures 4A, 4B, 4C, 4D:
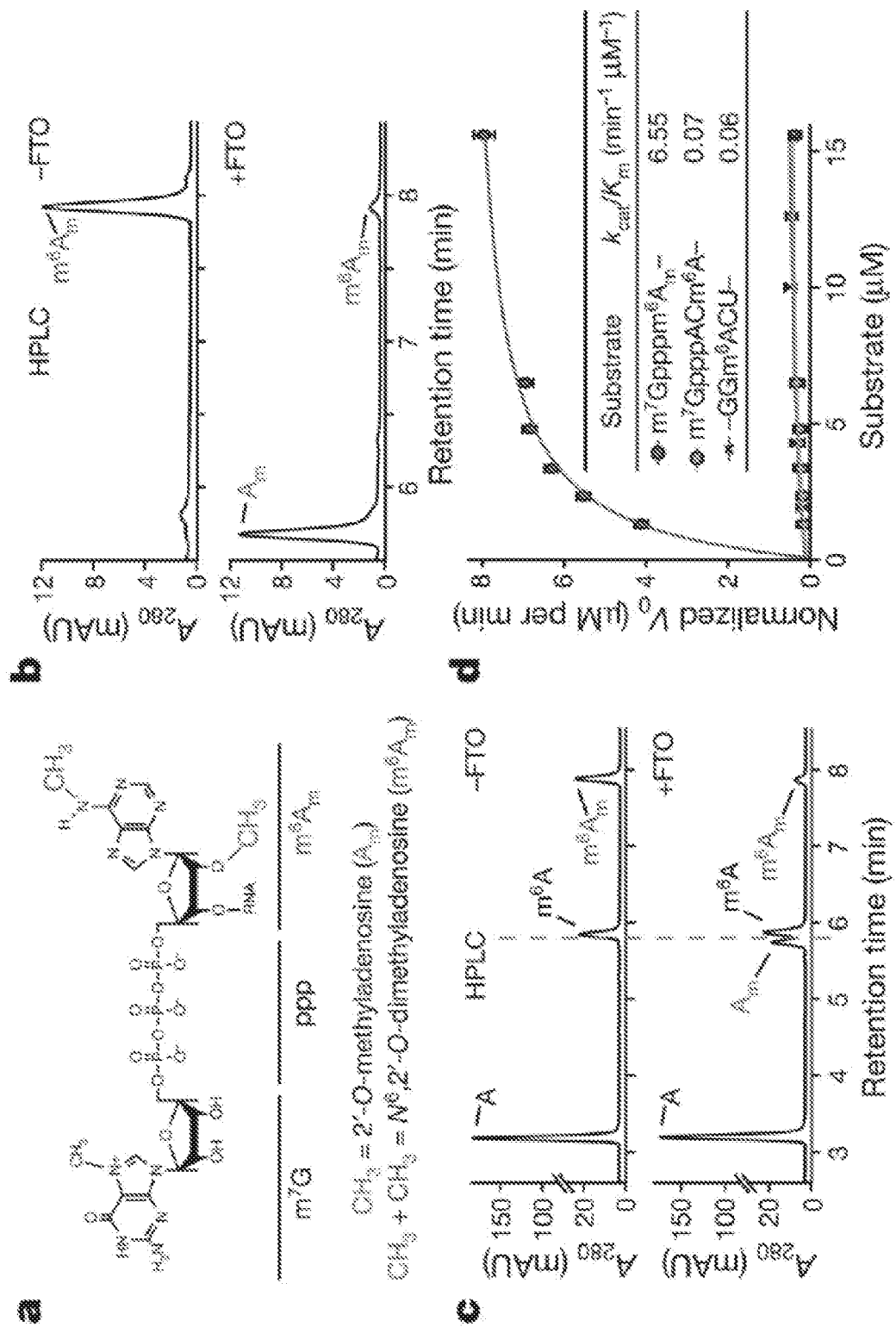

To determine whether FTO targets $m^6A_m$, FTO-mediated demethylation of a 21-nucleotide-long RNA with a 5' $m^7G$ cap followed by $m^6A_m$ was measured. FTO treatment readily converted $m^6A_m$ to $A_m$, indicating demethylation at the $N^6$-position (FIG. 3B, FIG. 4B). Next, FTO (100 nM) was added to an equimolar mixture of the $m^6A_m$ RNA and an RNA containing $m^6A$ in its physiological consensus. FTO demethylated nearly all $m^6A_m$ in 60 minutes, while $m^6A$ demethylation was not readily detected (FIG. 4C).

Demethylation of $m^6A$ was only readily detected using higher concentrations of FTO (200 nM), consistent with previous reports which used a 5:1 ratio of substrate and enzyme (Jia et al., "N6-Methyladenosine in Nuclear RNA is a Major Substrate of the Obesity-Associated FTO," *Nat. Chem. Biol.* 7:885-887 (2011), which is hereby incorporated by reference in its entirety). However, demethylation of $m^6A_m$ was achieved with substantially less FTO (20 nM) (FIGS. 3C-3G, FIG. 4D). The reported $k_{cat}$ of FTO towards $m^6A$ is relatively low compared to related dioxygenases. However, the $k_{cat}$ for FTO towards $m^6A_m$ is at least 20 times higher and the catalytic efficiency ($k_{cat}/K_m$) of FTO is approximately 100-fold higher towards $m^6A_m$ than $m^6A$ (FIG. 4D).

Figures 5A, 5B, 5C, 5D:
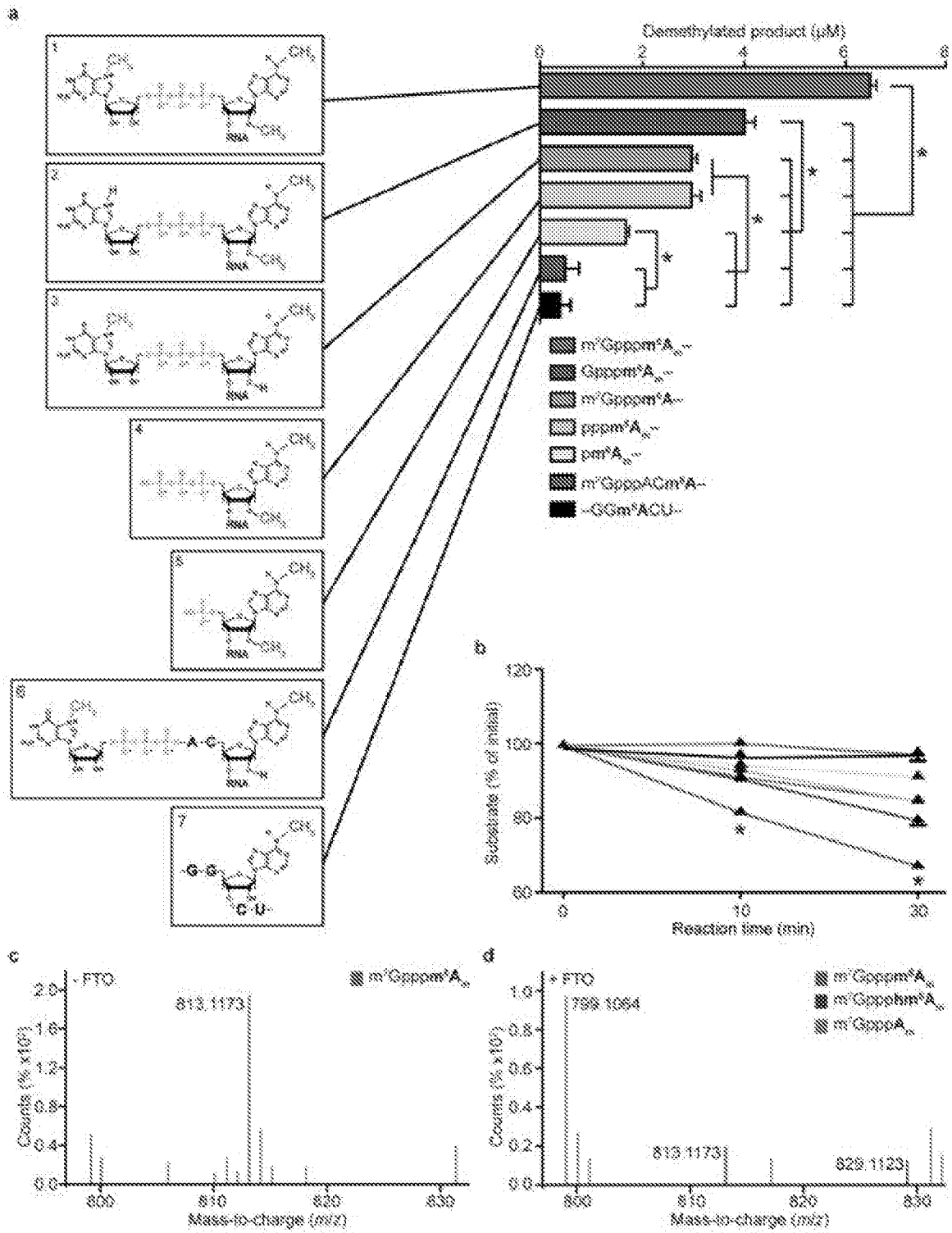
FIGS. 5A-5D illustrate how FTO-mediated demethylation of m$^6$A$_m$ depends on integral parts of the mRNA 5' cap and accurate mass measurement of the oxidative demethylation of the extended m$^7$Gpppm$^6$A$_m$-cap by FTO.

The activity of FTO towards $m^6A_m$ was dependent on specific structural elements of the extended $m^7G$ cap. FTO-mediated demethylation of $m^6A_m$ was impaired when $m^7G$ was substituted for G, and further reduction was seen when $m^7G$ was removed altogether (FIGS. 5A-5B). Demethylation was further reduced when the triphosphate was shortened to a monophosphate. Notably, the 2'-O-methyl substituent, which distinguishes $m^6A_m$ from $m^6A$, was also important for the demethylation activity of FTO. By contrast, FTO-mediated demethylation of $m^6A$ was poor in diverse sequence contexts (FIGS. 5A-5B).

Mass spectrometry confirmed FTO-mediated demethylation of $m^6A_m$ to $A_m$ (FIGS. 5C-5D). However, in addition to $A_m$, $N^6$-hydroxymethyl,2'-O-methyladenosine ("hm$^6A_m$") was also detected. Previous analysis of FTO activity towards m$^6$A showed that FTO-mediated demethylation occurs via a hydroxymethylated intermediate (Fu et al., "FTO-Mediated Formation of N6-Hydroxymethyladenosine and N6-Formyl adenosine in Mammalian RNA," *Nat. Commun.* 4:1798 (2013), which is hereby incorporated by reference in its entirety). Therefore, FTO-mediated demethylation of m$^6A_m$ may create additional cap diversity comprising oxidized 5' caps.

Example 3—FTO Controls the Balance Between m$^6A_m$ and $A_m$ In Vivo

Figures 6A, 6B, 6C:
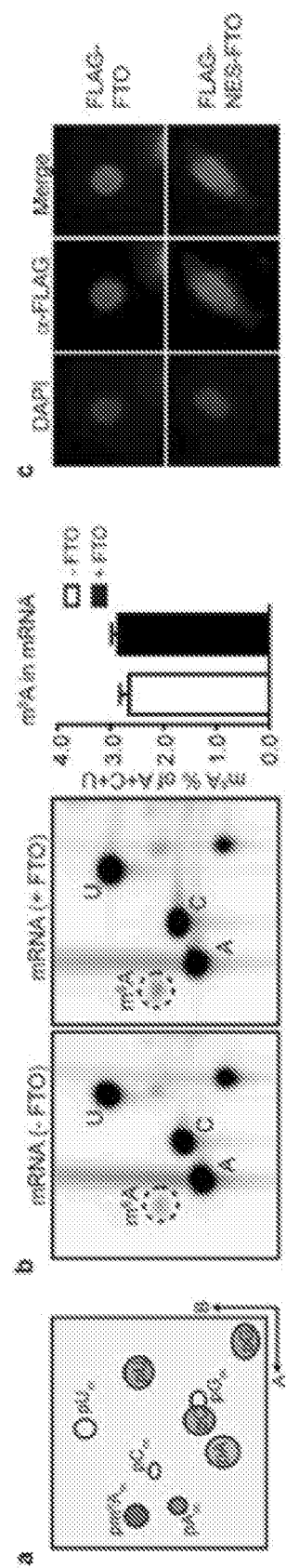
FIGS. 6A-6I show that m$^6$A$_m$ is the preferred substrate for FTO in vivo.
Figures 7A, 7B, 7C:
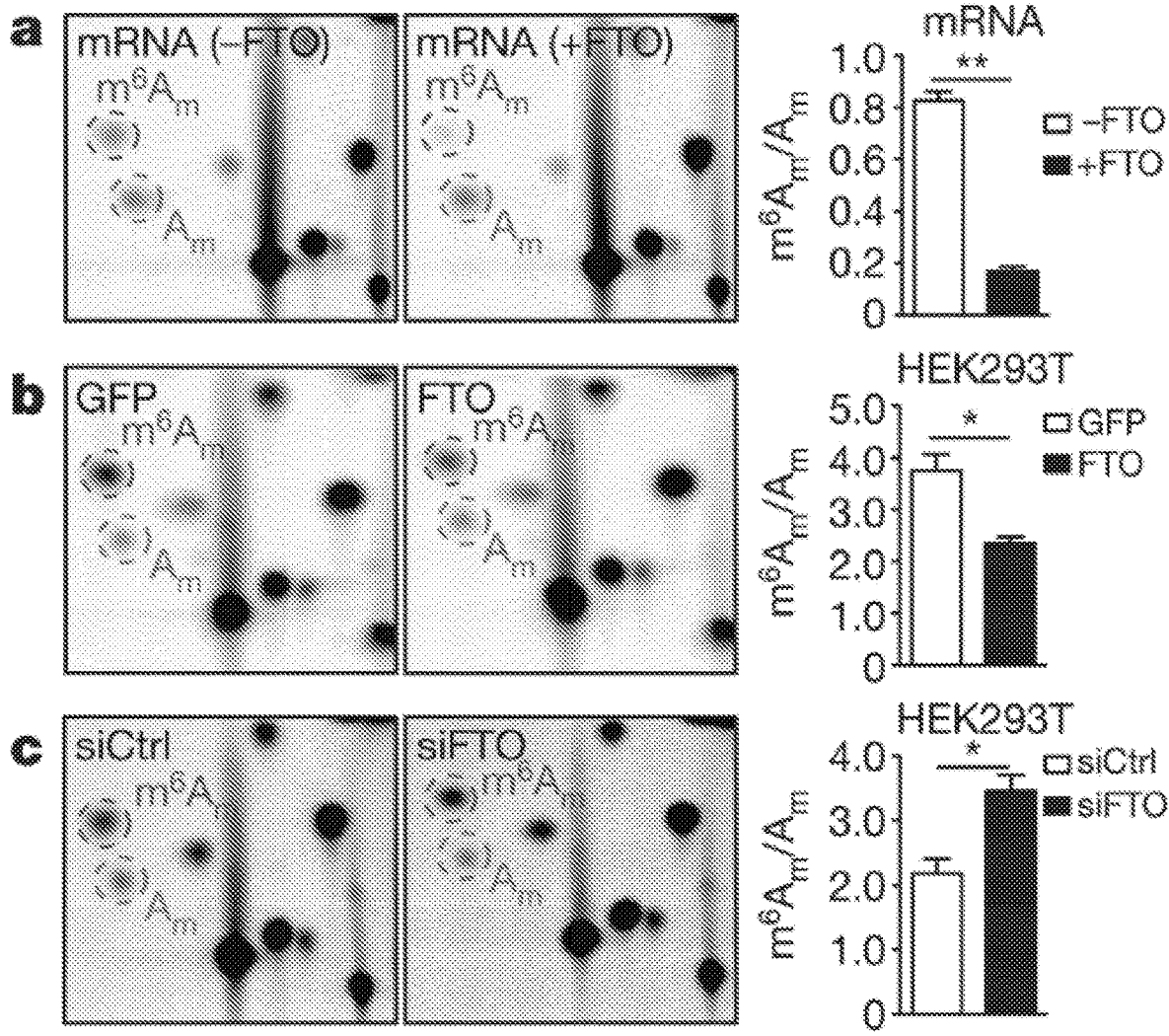
FIGS. 7A-7C show that $m^6A_m$ is the preferred substrate of FTO in vivo.
Figures 8A, 8B, 8C, 8D:
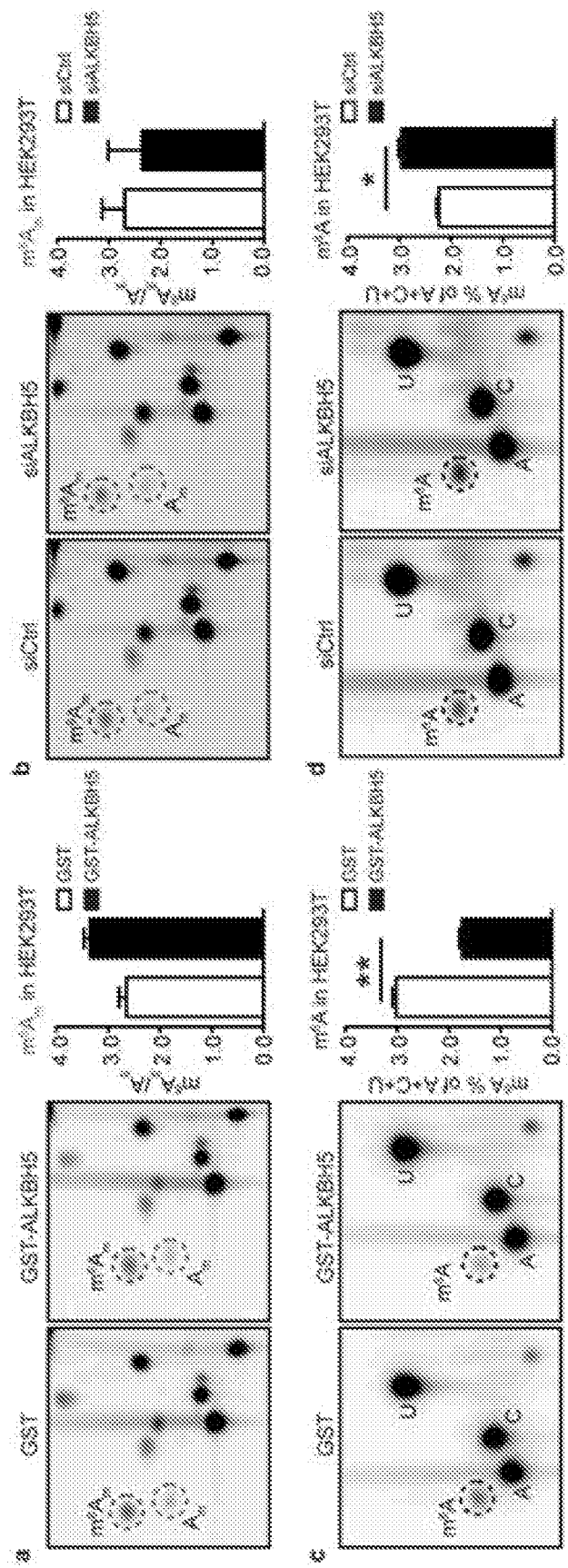
FIGS. 8A-8D show that ALKBH5 demethylates $m^6A$ but not $m^6A_m$ in mRNA in HEK293T cells.

Whether FTO demethylates m$^6A_m$ in cellular mRNA was next investigated. Thin-layer chromatography ("TLC") was used to quantify the ratio of m$^6A_m$ to $A_m$ in mRNA (Kruse et al., "A Novel Synthesis and Detection Method for Cap-Associated Adenosine Modifications in Mouse mRNA," *Sci. Rep.* 1:126 (2011), which is hereby incorporated by reference in its entirety). The m$^7$G cap was enzymatically removed from mRNA and the exposed 5' nucleotide was radiolabeled with [γ-$^{32}$P]-ATP. Two-dimensional TLC of the nucleotide hydrolysate reveals the identity of the 5' nucleotide (FIG. 6A) (Kruse et al., "A Novel Synthesis and Detection Method for Cap-Associated Adenosine Modifications in Mouse mRNA," *Sci. Rep.* 1:126 (2011), which is hereby incorporated by reference in its entirety). Treatment of cellular mRNA with recombinant FTO resulted in an approximately 80% reduction of the m$^6A_m$/$A_m$ ratio (FIG. 7A). Notably, the same mRNA samples did not show decreased m$^6$A upon FTO treatment (FIG. 6B). These results suggest that FTO does not efficiently demethylate m$^6$A in mRNA.

Figure 6D:
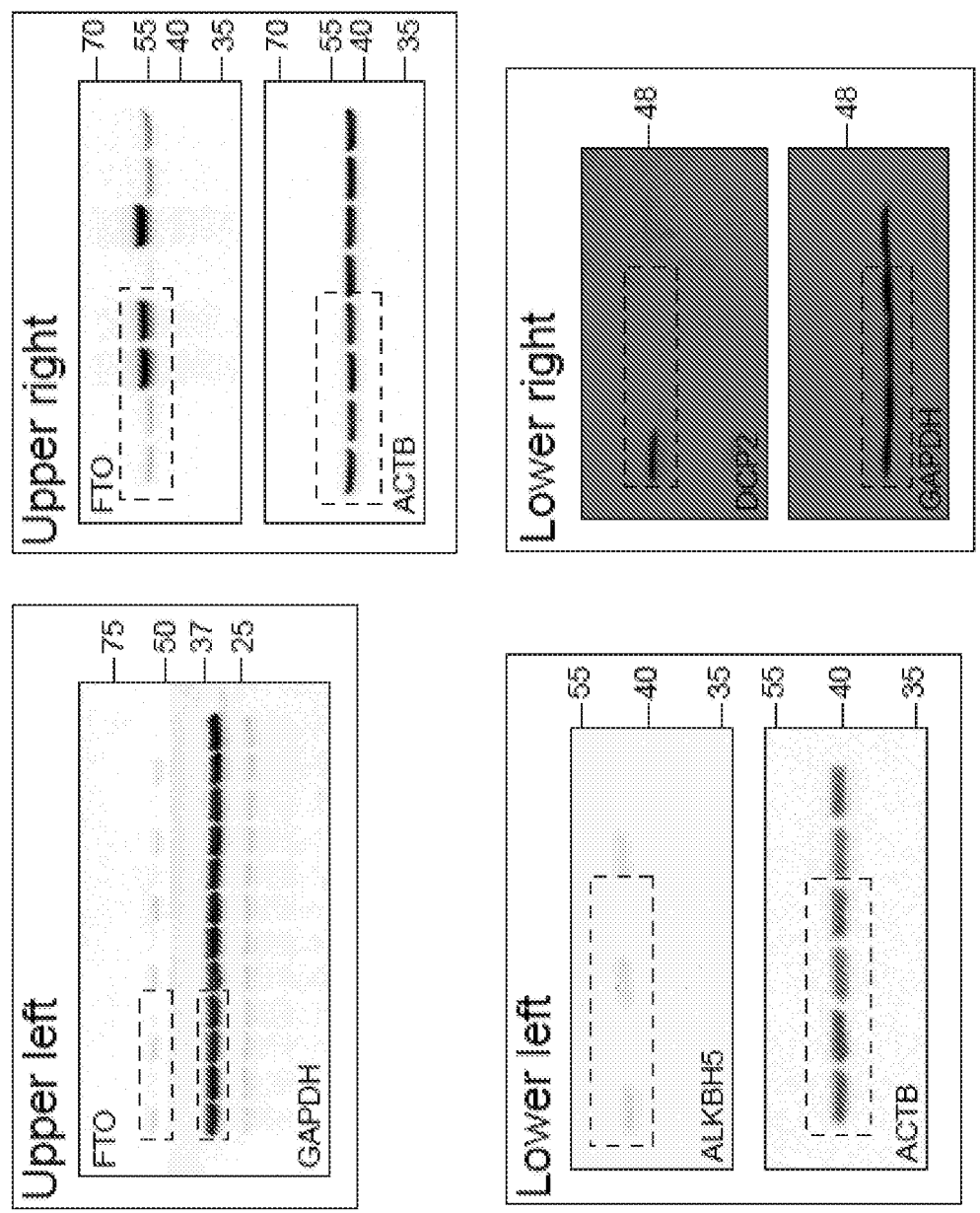
Figure 6E:
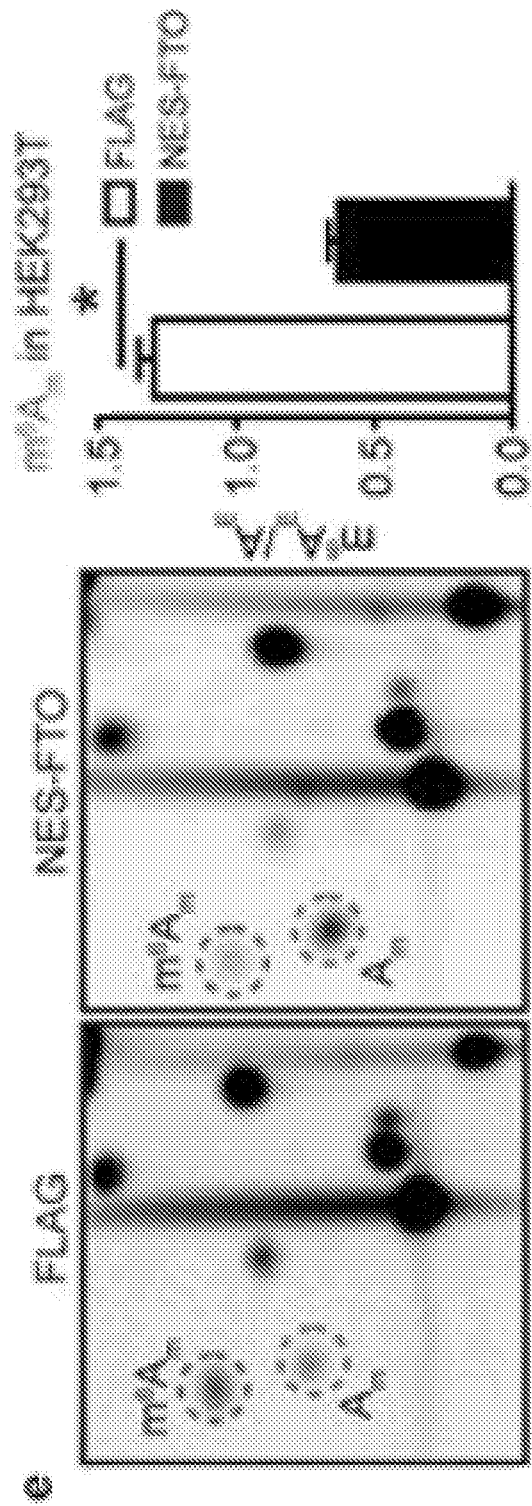
Figures 6F, 6G, 6H, 6I:
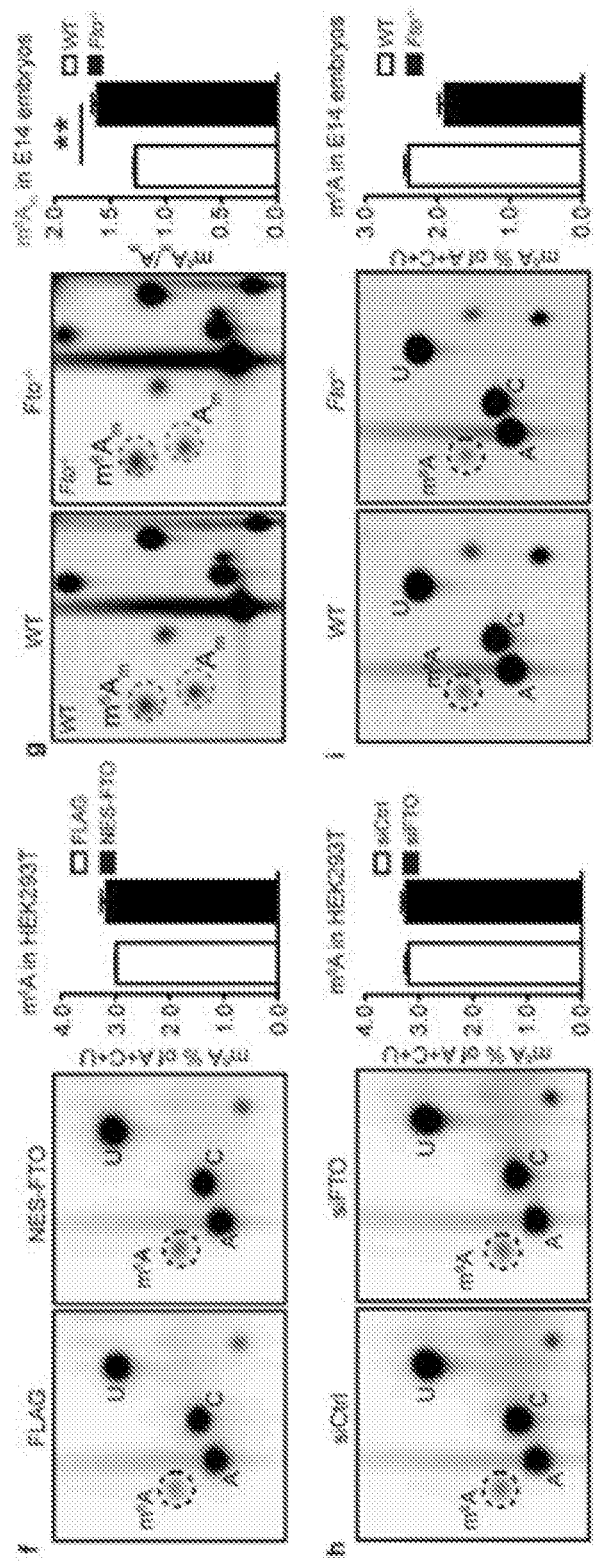

To determine whether FTO demethylates m$^6A_m$ in cells, HEK293T cells were transfected with Flag-FTO. This resulted in a significantly reduced m$^6A_m$/$A_m$ ratio relative to control cells (FIG. 7B). Although FTO is primarily nuclear, hypothalamic neurons exhibit cytosolic FTO after food deprivation (Vujovic et al., "Fasting Induced Cytoplasmic Fto Expression in some Neurons of Rat Hypothalamus," *PLoS One* 8:e63694 (2013), which is hereby incorporated by reference in its entirety). Since there is no reported approach to efficiently induce cytosolic localization of FTO in cultured cells, FTO containing a nuclear-export signal ("NES-FTO") was expressed in HEK293T cells (FIGS. 6C-6D). This resulted in a more pronounced drop in the m$^6A_m$/$A_m$ ratio than wild-type FTO expression (FIG. 6E). At this expression level, NES-FTO did not reduce m$^6$A levels (FIG. 6F). Thus, FTO demethylates m$^6A_m$ in cells and cytosolic translocation of FTO may further enhance the demethylation of cytoplasmic m$^6A_m$ mRNAs.

FTO knockdown further increased the already high (Kruse et al., "A Novel Synthesis and Detection Method for Cap-Associated Adenosine Modifications in Mouse mRNA," *Sci. Rep.* 1:126 (2011), which is hereby incorporated by reference in its entirety) m$^6A_m$/$A_m$ ratio in cells (FIG. 7C). Similarly, the m$^6A_m$/$A_m$ ratio was increased in Fto-knockout mouse embryos compared to wild type (FIG. 6G). No increase in m$^6$A levels was detectable in FTO-knockdown cells or Fto-knockout mouse embryos (FIGS. 6H-6I). By contrast, ALKBH5 knockdown increased m$^6$A levels without increasing m$^6A_m$ levels and ALKBH5 expression selectively demethylated m$^6$A but not m$^6A_m$ (FIGS. 8A-8D). These results suggest that FTO targets m$^6A_m$ whereas ALKBH5 targets m$^6$A in vivo.

Example 4—m$^6A_m$ mRNAs Exhibit Increased Half-Life in Cells

To determine whether m$^6A_m$ confers unique effects on mRNA, cellular mRNAs were first classified based on whether they begin with m$^6A_m$, $A_m$, 2'-O-methylcytidine ("$C_m$"), 2'-O-methylguanosine ("$G_m$"), or 2'-O-methyluridine ("$U_m$"). mRNAs beginning with m$^6A_m$ were identified by miCLIP (Linder et al., "Single-Nucleotide-Resolution Mapping of m6A and m6Am Throughout the Transcriptome," *Nat. Methods* 12:767-772 (2015), which is hereby incorporated by reference in its entirety) (Table 2). miCLIP-mapped m$^6A_m$ residues were validated based on their overlap with transcription start sites and their preferential localization in a sequence context matching the core initiator motif (Forrest et al., "A Promoter-Level Mammalian Expression Atlas," *Nature* 507:462-470 (2014), which is hereby incorporated by reference in its entirety) (FIGS. 9A-9B, Table 2). mRNAs that did not contain m$^6A_m$ were considered to begin with $A_m$, $C_m$, $G_m$, or $U_m$ based on the annotated starting nucleotide (Table 4).

Figures 9A, 9B, 9C, 9D, 9E, 9F, 9G:
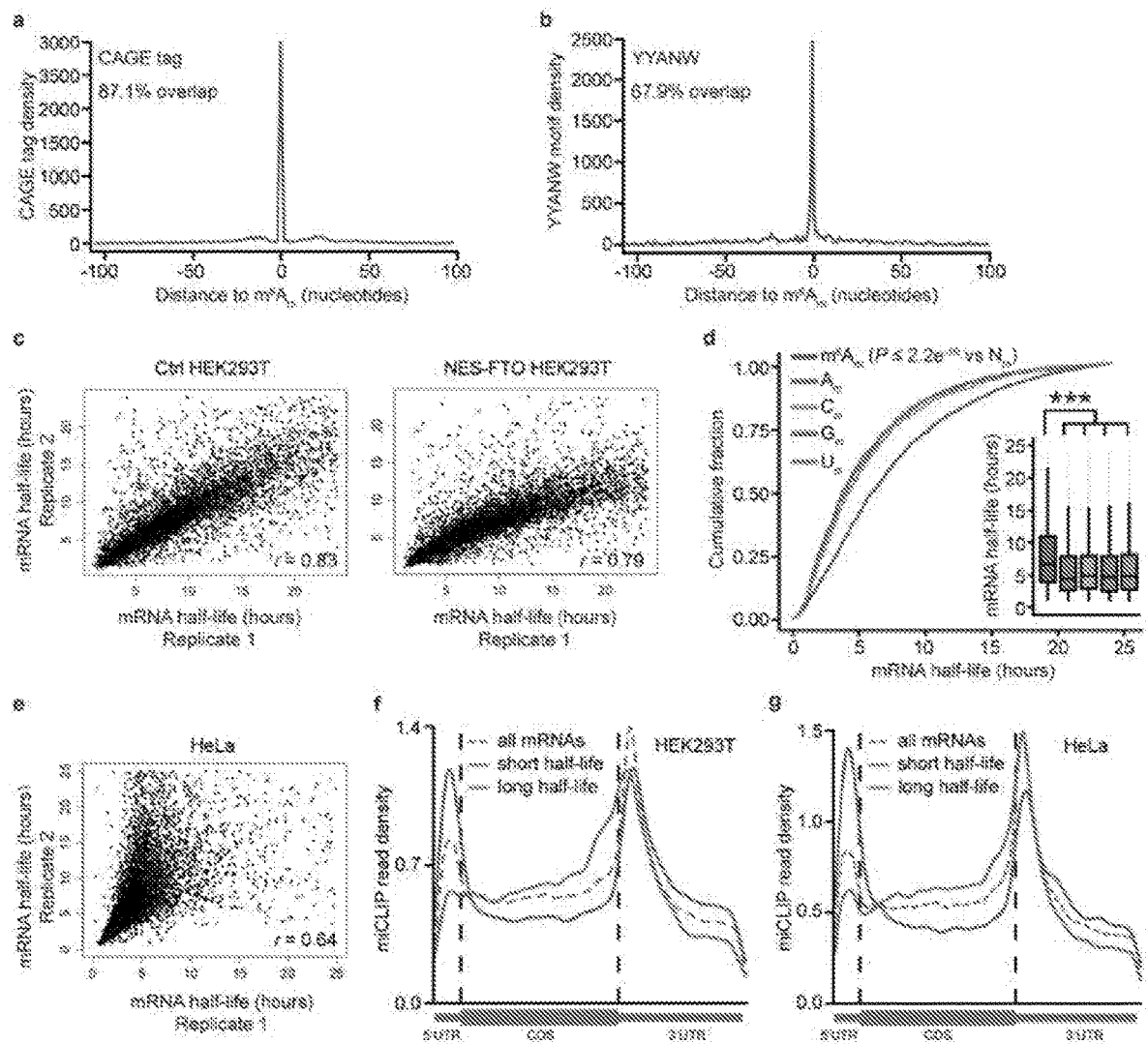
FIGS. 9A-G show that newly mapped m$^6$A$_m$ clusters overlap with transcription start sites ("TSS") and the YYANW initiator core motif and mark mRNAs for increased half-life. To confirm that that the residues identified as m$^6$A$_m$ in miCLIP reflect transcription initiation sites, known TSS and transcription initiation sequences around each m$^6$A$_m$-containing region were searched. Notably, owing to the calling algorithm, these regions do not contain any 5' UTR m$^6$A. To identify genome-wide positions of the TSS, published CAGE-seq datasets were used. Shown is the nucleotide distance of the called m$^6$A$_m$ from TSS (FIG. 9A) and YYANW (FIG. 9B). These results demonstrate that TSS and the YYANW core initiator sequence are highly clustered at m$^6$A$_m$-containing regions (5'-most nucleotide is at position 0 on the x-axis). This suggests that the called m$^6$A$_m$-containing regions reflect true TSS.
Figures 10A, 10B, 10C, 10D:
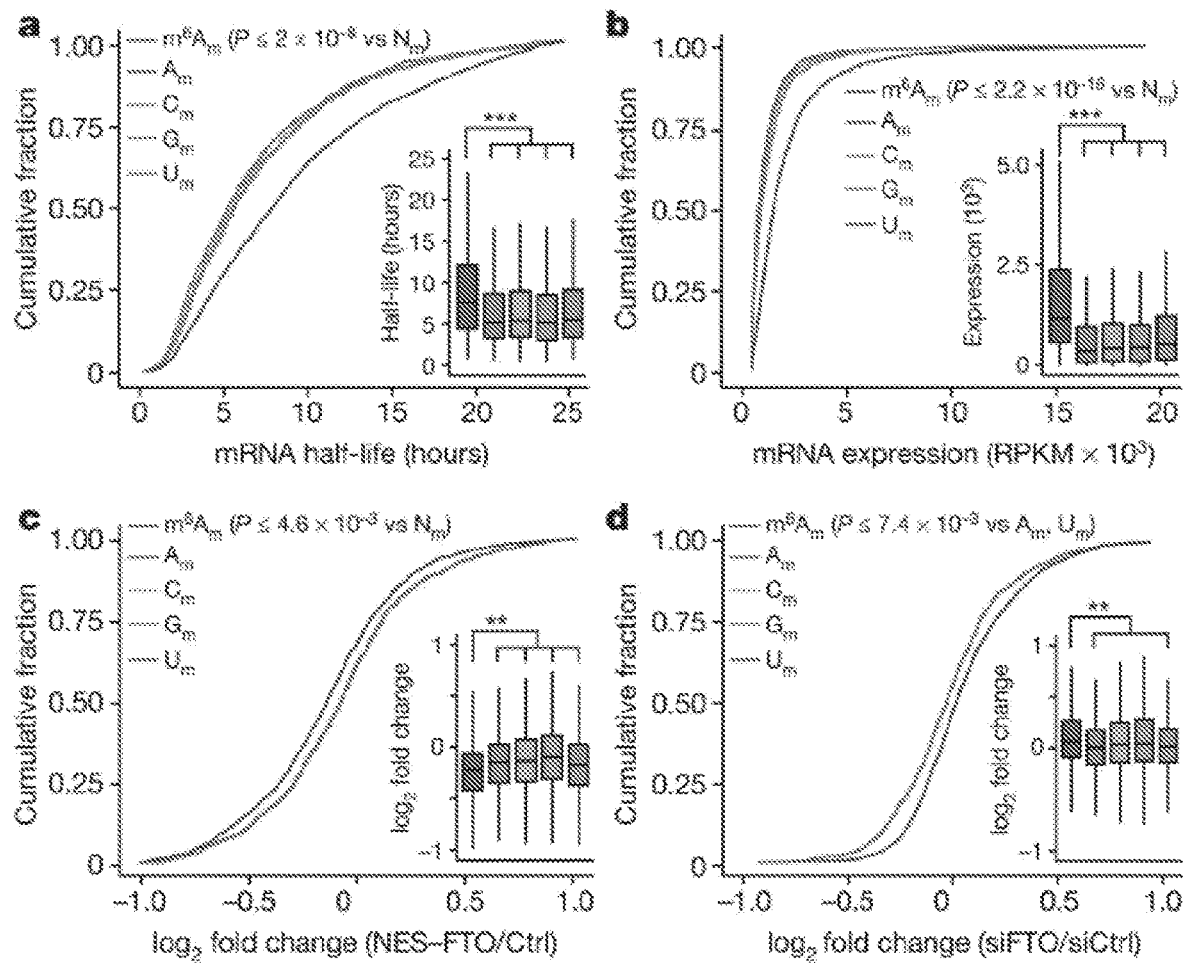
FIGS. 10A-10D show that the presence of m$^6$A$_m$ is associated with increased mRNA half-life.

Whether mRNA stability is linked to the identity of the first nucleotide was next investigated. mRNAs beginning with $A_m$, $C_m$, $G_m$, and $U_m$ exhibited a very similar distribution of half-lives, with an average of around 6 hours in HEK293T cells (FIG. 10A). However, mRNAs that begin with an m$^6A_m$ were markedly more stable, with an average increase in half-life of approximately 2.5 hours (FIG. 10A, FIGS. 9C-9E, Table 5). A link between m$^6A_m$ and mRNA stability is also seen when examining the distribution of m$^6$A and m$^6A_m$ miCLIP reads in long-lived and short-lived mRNAs (FIGS. 9F-9G).

TABLE 5

| ANCOVA Analysis of m$^6A_m$ Effect on mRNA Half-Life | |
|---|---|
| Covariate | ANCOVA P-value |
| None | 2.63E-93 |
| Number of ARE, GRE, and URE* | 1.40E-45 |
| RNA expression (log2(FPKM)) | 2.43E-80 |
| Number of CAGE sites | 6.77E-100 |
| Translation efficiency (log2(TE)) | 5.90E-33 |
| Number of TOP motifs in 5' UTR | 3.05E-09 |
| GC composition in 5' UTR | 5.34E-48 |
| Length of 5' UTR | 1.30E-52 |
| Length of 3' UTR | 1.23E-47 |
| Number of exons in 5' UTR | 1.11E-48 |
| Number of exons in 3' UTR | 1.48E-48 |
| Number of conserved miRNA sites | 3.94E-44 |
| 5' UTR MFE** to length ratio | 2.54E-60 |
| Number of G-quadrupulexes in 5' UTR | 2.13E-56 |

*ARE, AU-rich elements; GRE, GU-rich elements; URE, U-rich elements
**MFE, Minimum free energy It was reasoned that if m$^6A_m$ stabilizes mRNA, then this would lead to increased m$^6A_m$ mRNA levels. Indeed, m$^6A_m$ mRNAs exhibit higher transcript levels than mRNAs that begin with $A_m$, $C_m$, $G_m$, or $U_m$ (FIG. 10B). Although the increased expression levels could be influenced by transcription rates, the half-life data suggests that increased mRNA stability contributes to the increased abundance of m$^6A_m$ mRNAs. Taken together, these data indicate that the first nucleotide is an important determinant of mRNA stability and abundance.

Additionally, $m^6A_m$ mRNAs may increase translation efficiency (FIGS. 1A-1F). This is in line with a previous study that observed increased translation efficiency of mRNAs containing methylated adenine at the transcription start site (Schwartz et al., "Perturbation of m6A Writers Reveals Two Distinct Classes of mRNA Methylation at Internal and 5' sites," *Cell Reports* 8:284-296 (2014), which is hereby incorporated by reference in its entirety).

Example 5—Alternations in $m^6A_m$ Levels Control mRNA Stability

Figures 11A, 11B, 11C, 11D, 11E:
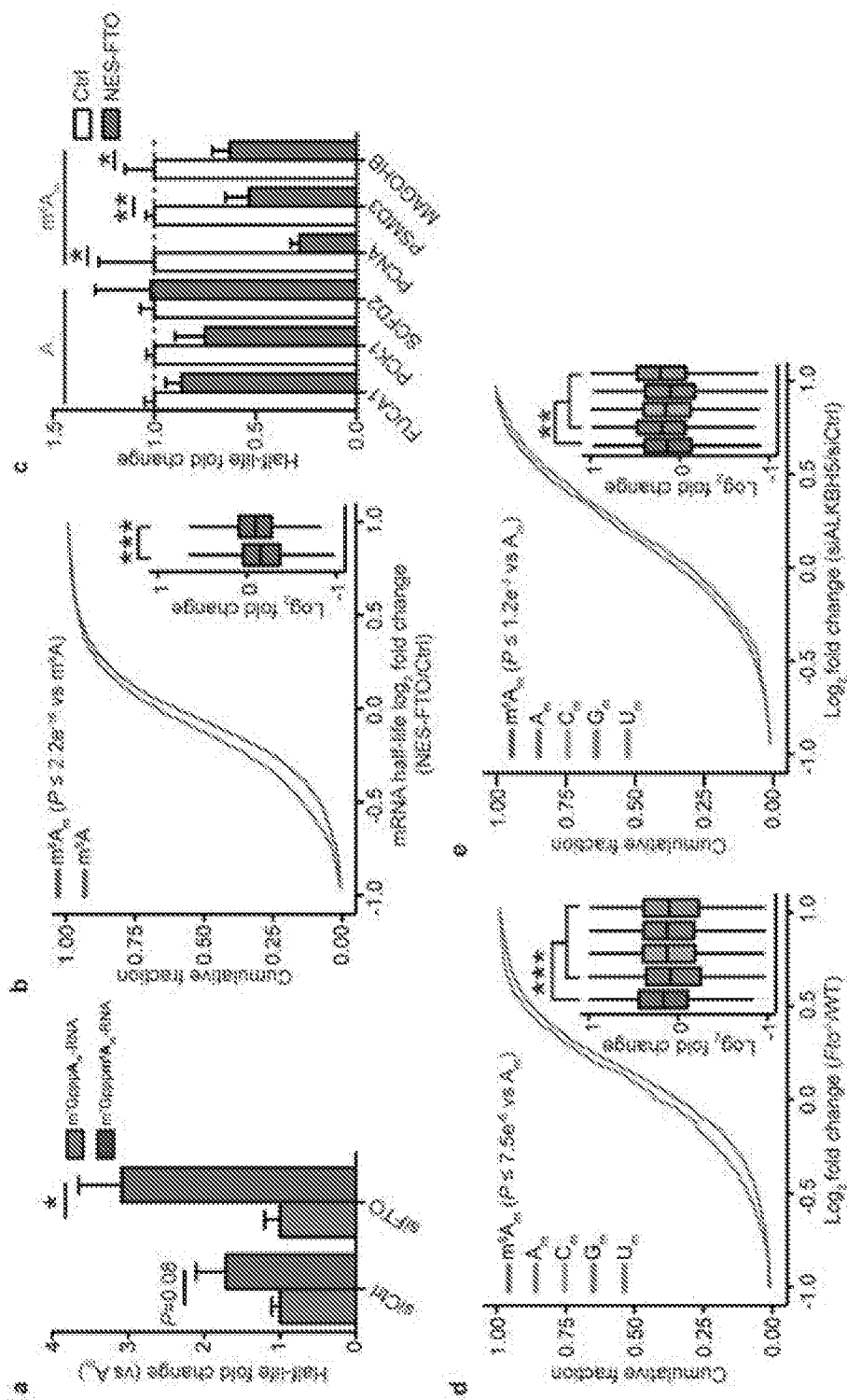
FIGS. 11A-E show the expression changes of $m^6A_m$, $m^6A_m$ and $A_m$ mRNAs upon NES-FTO expression and FTO or ALKBH5 deficiency.

To test directly whether $m^6A_m$ can confer stability to mRNA, polyadenylated mRNAs were synthesized in vitro, starting with either $m^7GpppA_m$ or $m^7Gpppm^6A_m$. Electroporation of these mRNAs into HEK293T cells showed that the $m^6A_m$ mRNA was more stable than the $A_m$-initiated mRNA (FIG. 11A).

Next, cellular $m^6A_m$ levels were selectively reduced by expressing NES-FTO and mRNA half-life was monitored. At the level of transfection used, changes in $m^6A$ were not detectable, but $m^6A_m$ levels were significantly reduced (FIGS. 6C-6F). Analysis of transcriptome-wide fold-changes in mRNA half-lives showed that NES-FTO expression causes a significant decrease in $m^6A_m$ mRNA half-life compared to mRNAs initiated with $A_m$ (FIG. 10C). $m^6A$-containing mRNAs were unaffected (FIG. 11B). The effect of NES-FTO on $m^6A_m$ mRNAs was also seen when monitoring the stability of individual transcripts using BrU pulse-chase labelling (FIG. 11C). These results suggest that demethylation of $m^6A_m$ reduces the stability of mRNAs that begin with this nucleotide.

Although $m^6A_m$ levels are typically high in most cell types (Wei et al., "N6, O2'-Dimethyladenosine a Novel Methylated Ribonucleoside next to the 5' Terminal of Animal Cell and Virus mRNAs," *Nature* 257:251-253 (1975) and Kruse et al., "A Novel Synthesis and Detection Method for Cap-Associated Adenosine Modifications in Mouse mRNA," *Sci. Rep.* 1:126 (2011), which are hereby incorporated by reference in their entirety), $m^6A_m$ levels were further increased by FTO knockdown and mRNA levels were measured using RNA-seq. Notably, mRNAs that start with $m^6A_m$ showed higher abundance after FTO knockdown compared to $A_m$-initiated mRNAs (FIG. 10D). This effect was also seen in Fto-knockout mouse liver compared to wild type (FIG. 11D). Notably, ALKBH5 knockdown did not affect $m^6A_m$ mRNAs (FIG. 11E). These results suggest that increasing $m^6A_m$ levels enhances the stability of these mRNAs.

Example 6—$m^6A_m$ Confers Reduced Susceptibility to Decapping

Figures 12A, 12B, 12C, 12D:
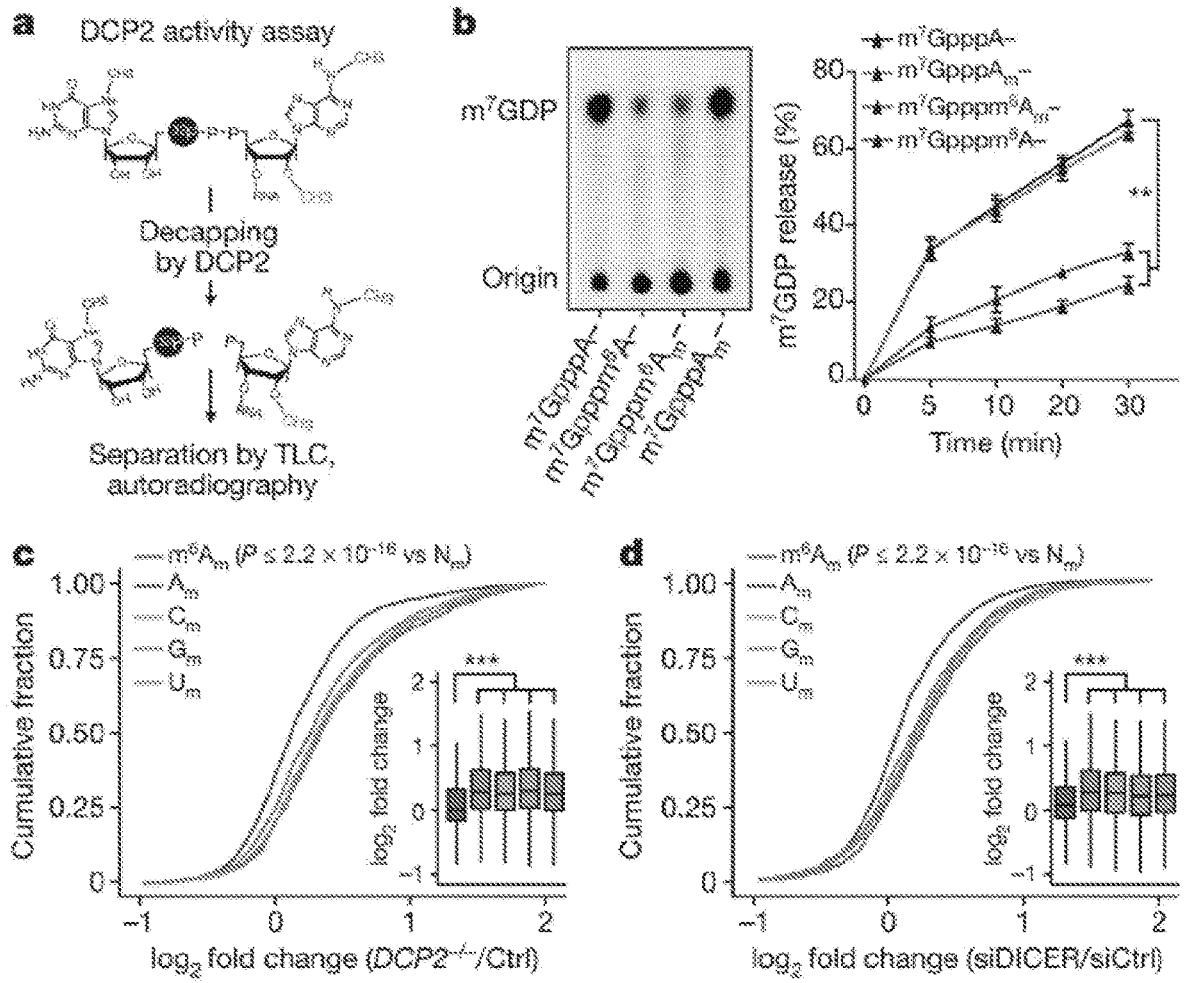
FIGS. 12A-12D show that $m^6A_m$ mRNAs are resistant to DCP2-mediated decapping.
Figures 13A, 13B, 13C, 13D, 13E, 13F, 13G, 13H:
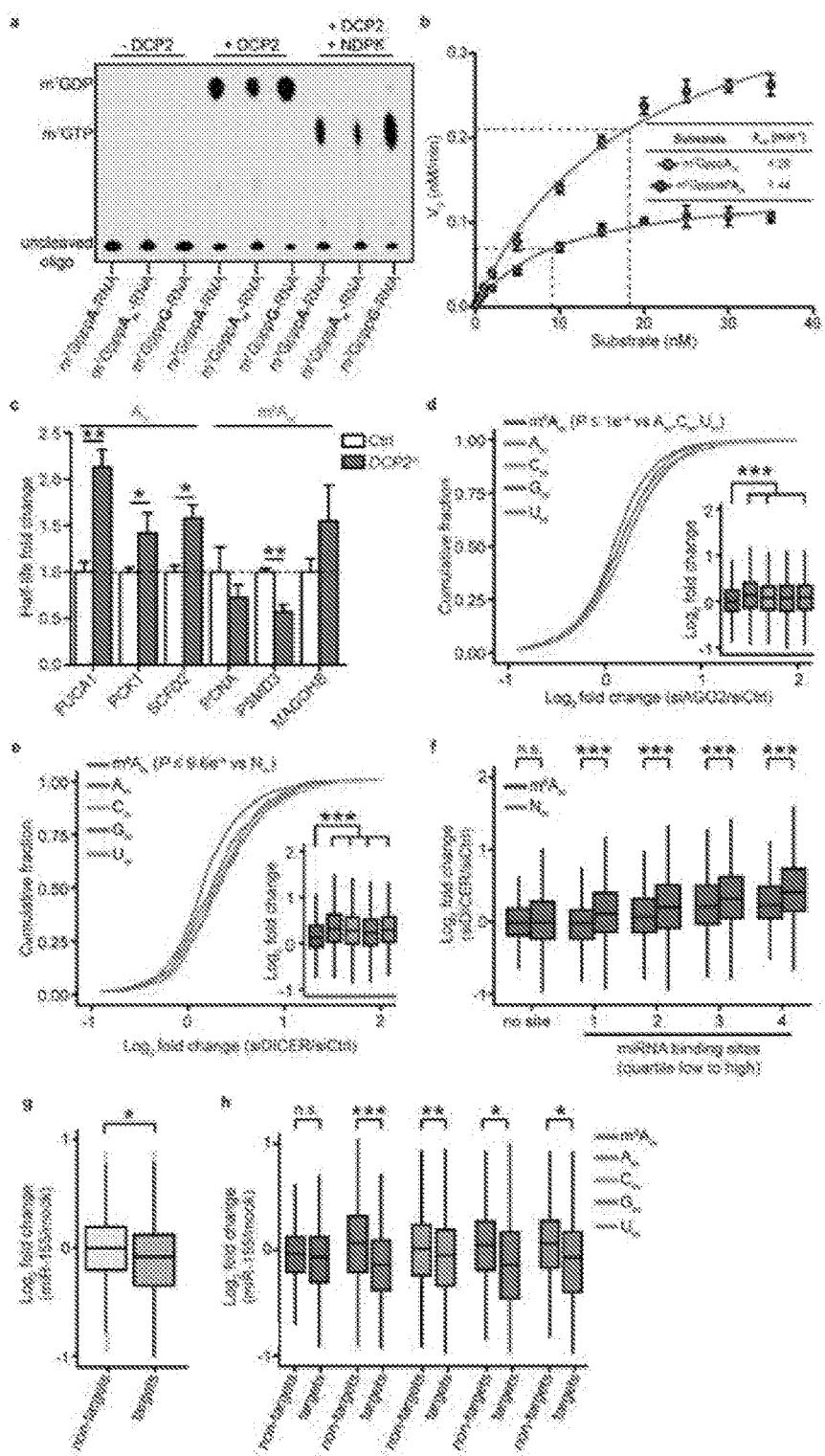
FIGS. 13A-13H show that $m^6A_m$ mRNAs are resistant to DCP2-mediated decapping and microRNA-mediated gene silencing.

Since mRNA degradation often involves decapping, the possibility that $m^6A_m$ affects this process was considered. Studies of the mRNA-decapping enzyme DCP2 (Wang et al., "The hDcp2 Protein is a Mammalian mRNA Decapping Enzyme," *PNAS* 99:12663-12668 (2002), which is hereby incorporated by reference in its entirety) have previously used RNAs with an $m^7G$ cap, but did not examine the effect of the methylation state of the subsequent nucleotide. $m^7G$-capped RNAs ($m^7GpppRNA$) with a $^{32}P$-labelled γ-phosphate proximal to the $m^7G$ were generated. DCP2-mediated decapping releases radiolabeled $m^7GDP$, which was detected by TLC (FIG. 12A, FIG. 13A). RNAs containing an $m^7G$ cap followed by an unmodified adenosine or $A_m$ showed equivalent efficiencies of decapping, indicating that the 2'-O-methyl modification does not affect DCP2-mediated decapping (FIG. 12B). However, RNAs with $m^7G$ followed by $m^6A_m$ or $m^6A$ showed significantly reduced decapping (FIG. 12B, FIG. 13B).

Whether $m^6A_m$ impairs decapping in cells was next investigated. It was reasoned that DCP2 deficiency would lead to increased $A_m$, $C_m$, $G_m$, and $U_m$mRNA levels relative to $m^6A_m$ mRNAs. Transcriptome-wide analysis showed increased levels of mRNAs that start with $A_m$, $C_m$, $G_m$, or $U_m$ in DCP2-deficient HEK293T cells compared to controls (FIG. 12C). $m^6A_m$mRNAs were less affected, indicating that they are less susceptible to DCP2-dependent degradation (FIG. 12C). As an additional control, the stability of individual mRNAs was monitored using BrU pulse-chase labelling. Notably, $A_m$ mRNAs showed stabilization upon DCP2 depletion, while $m^6A_m$ mRNAs were not significantly stabilized (FIG. 13C). These results suggest that $m^6A_m$ confers resistance to DCP2, resulting in increased mRNA stability.

Example 7—$m^6A_m$ Impairs MicroRNA-Mediated mRNA Degradation

One unresolved question in microRNA-mediated degradation is why some mRNAs are efficiently degraded by microRNAs while others show less robust degradation (Wu et al., "Let Me Count the Ways: Mechanisms of Gene Regulation by miRNAs and siRNAs," *Mol. Cell* 29:1-7 (2008), which is hereby incorporated by reference in its entirety). MicroRNA-mediated mRNA degradation involves decapping (Rehwinkel et al., "A Crucial Role for GW182 and the DCP1:DCP2 Decapping Complex in miRNA-Mediated Gene Silencing," *RNA* 11:1640-1647 (2005), which is hereby incorporated by reference in its entirety). Thus, whether microRNA-mediated degradation could be influenced by the presence of $m^6A_m$ was next investigated.

To test this, gene expression data sets of HEK293 cells deficient in DICER and AGO2 were examined (Schmitter et al., "Effects of Dicer and Argonaute Down-Regulation on mRNA Levels in Human HEK293 cells," *Nucleic Acids Res.* 34:4801-4815 (2006), which is hereby incorporated by reference in its entirety). In both cases, microRNA-mediated mRNA degradation is impaired, resulting in increased levels of microRNA-targeted mRNAs. If $m^6A_m$ mRNAs were less susceptible to microRNA-mediated degradation, they would exhibit less-pronounced upregulation upon loss of DICER or AGO2. Indeed, mRNAs starting with $A_m$, $C_m$, $G_m$, or $U_m$ exhibited a significantly higher increase in expression than $m^6A_m$ mRNAs (FIG. 12D, FIGS. 13D-13F). Thus, $m^6A_m$mRNAs are less susceptible to microRNA-mediated degradation.

Next, whether $m^6A_m$ mRNAs show reduced susceptibility to microRNA-mediated mRNA degradation upon introduction of a single microRNA was investigated. To do so, gene expression data sets from miR-155-transfected HeLa cells (Guo et al., "Mammalian MicroRNAs Predominantly Act to Decrease Target mRNA Levels," *Nature* 466:835-840 (2010), which is hereby incorporated by reference in its entirety) and mRNAs with predicted miR-155-binding sites were investigated. This analysis revealed that $m^6A_m$ mRNAs were significantly more resistant to miR-155-mediated mRNA degradation compared to other mRNAs (FIGS. 13G-13H). These data suggest that $m^6A_m$ reduces the susceptibility of mRNAs to endogenous decay pathways such as microRNA-mediated mRNA degradation.

Discussion of Examples 1-7

The present application identifies $m^6A_m$ as a dynamic and reversible epitranscriptomic mark. In contrast to the concept that epitranscriptomic modifications are found internally in mRNA, Examples 1-7 supra demonstrate that the 5' cap harbors epitranscriptomic information that determines the fate of mRNA. The presence of $m^6A_m$ in the extended cap confers increased mRNA stability, while $A_m$ is associated with baseline stability. $m^6A_m$ has long been known to be a pervasive modification in a large fraction of mRNA caps in the transcriptome (Wei et al., "N6, O2'-Dimethyladenosine a Novel Methylated Ribonucleoside Next to the 5' Terminal of Animal Cell and Virus mRNAs," Nature 257:251-253 (1975), which is hereby incorporated by reference in its entirety), making it the second most prevalent modified nucleotide in cellular mRNA. Dynamic control of $m^6A_m$ can therefore influence a large portion of the transcriptome.

The concept of reversible base modifications is appealing since it raises the possibility that the fate of an mRNA can be determined by switching a modification on and off. Examples 1-7 supra show that FTO is an $m^6A_m$ 'eraser' and forms $A_m$ in cells. FTO resides in the nucleus, where it probably demethylates nuclear RNA and newly synthesized mRNAs. Demethylation of cytoplasmic $m^6A_m$ mRNAs may be induced by stimuli that induce cytosolic translocation of FTO.

The specificity of FTO towards $m^6A_m$ in cells is supported by the finding that depletion of FTO increases $m^6A_m$ mRNA levels relative to $A_m$ mRNAs, while $m^6A$-containing mRNAs are largely unaffected. Although FTO prefers $m^6A_m$, high levels of FTO overexpression cause small but measurable reductions in $m^6A$ levels in specific mRNAs (Meyer et al., "5' UTR m6A Promotes Cap-Independent Translation," Cell 163:999-1010 (2015), which is hereby incorporated by reference in its entirety). Additionally, an earlier study reported small increases in total $m^6A$ levels in cell lines following FTO knockdown (Jia et al., "N6-Methyladenosine in Nuclear RNA is a Major Substrate of the Obesity-Associated FTO," Nat. Chem. Biol. 7:885-887 (2011), which is hereby incorporated by reference in its entirety). $m^6A$ measurement in FTO-depleted cells is complicated by the fact that FTO depletion causes increases in $m^6A_m$ mRNA expression levels, which can lead to indirect changes in $m^6A$ levels. Higher mRNA expression also results in increased $m^6A$ peak calling owing to the stochastic nature of detecting $m^6A$ modifications in low-abundance mRNAs (Liu et al., "Decomposition of RNA Methylome Reveals Co-Methylation Patterns Induced by Latent Enzymatic Regulators of the Epitranscriptome," Mol. Biosyst. 11:262-274 (2015), which is hereby incorporated by reference in its entirety).

Prior to the development of single-nucleotide-resolution $m^6A$ and $m^6A_m$ mapping techniques (Linder et al., "Single-Nucleotide-Resolution Mapping of m6A and m6Am Throughout the Transcriptome," Nat. Methods 12:767-772 (2015), which is hereby incorporated by reference in its entirety), $m^6A$ mapping inadvertently included $m^6A_m$ sites that were misannotated as $m^6A_m$ These older techniques should more accurately be designated as 6 mA mapping (that is, the methylated base) to reflect their inability to distinguish $m^6A_m$ and $m^6A$. Similarly, $m^6A$ immunoblot and $m^6A$-IP qRT-PCR cannot distinguish between $m^6A$ and $m^6A_m$. The present application demonstrates that upregulated peaks in the Fto-knockout transcriptome (Hess et al., "The Fat Mass and Obesity Associated Gene (Fto) Regulates Activity of the Dopaminergic Midbrain Circuitry," Nat. Neurosci. 16:1042-1048 (2013), which is hereby incorporated by reference in its entirety), which are enriched in the 5' UTR, probably reflect FTO-regulated $m^6A_m$ sites. A similar increase in 5' UTR peaks was reported in a $m^6A$ mapping study of Fto-deficient mouse fibroblasts (Zhou et al., "Dynamic m6A mRNA Methylation Directs Translational Control of Heat Shock Response," Nature 526:591-594 (2015), which is hereby incorporated by reference in its entirety). The 5' UTR enrichment of these peaks suggests that these residues may also reflect $m^6A_m$.

Previous studies on FTO should be reconsidered in light of its preferential activity towards $m^6A_m$. FTO has been linked to altered splicing of mRNAs, which may indicate a role for $m^6A_m$ in this process (Zhao et al., "FTO-Dependent Demethylation of N6-Methyladenosine Regulates mRNA Splicing and is Required for Adipogenesis," Cell Res. 24:1403-1419 (2014), which is hereby incorporated by reference in its entirety). FTO knockdown increases the translation of HSPAJA (Meyer et al., "5' UTR m6A Promotes Cap-Independent Translation," Cell 163:999-1010 (2015) and Zhou et al., "Dynamic m6A mRNA Methylation Directs Translational Control of Heat Shock Response," Nature 526:591-594 (2015), which are hereby incorporated by reference in their entirety). Although site-directed mutagenesis supports a role for 5' UTR $m^6A$ in the translation of this mRNA (Zhou et al., "Dynamic m6A mRNA Methylation Directs Translational Control of Heat Shock Response," Nature 526:591-594 (2015), which is hereby incorporated by reference in its entirety), $m^6A_m$ also probably contributes to this effect owing to its sensitivity to FTO. FTO-deficient mice display diverse phenotypes ranging from growth retardation to metabolic changes and abnormalities in brain reward pathways (Hess et al., "The Fat Mass and Obesity Associated Gene (Fto) Regulates Activity of the Dopaminergic Midbrain Circuitry," Nat. Neurosci. 16:1042-1048 (2013) and Fischer et al., "Inactivation of the Fto Gene Protects from Obesity," Nature 458:894-898 (2009), which are hereby incorporated by reference in their entirety). Humans with FTO loss-of-function mutations exhibit growth retardation and malformations (Boissel et al., "Loss-of-Function Mutation in the Dioxygenase-Encoding FTO Gene Causes Severe Growth Retardation and Multiple Malformations," Am. J. Hum. Genet. 85:106-111 (2009), which is hereby incorporated by reference in its entirety). Since $m^6A_m$ mRNAs are enriched in functional categories linked to RNA splicing, translation and metabolism (FIGS. 2A-2F), alterations in these pathways may contribute to the physiological effects of FTO deficiency.

DCP2 is a 'reader' of the mRNA cap modification state, thereby contributing to the stability of $m^6A_m$ mRNAs. $m^6A_m$ impairs mRNA decapping, rendering $m^6A_m$ mRNAs less susceptible to microRNA-mediated mRNA degradation. Therefore, $m^6A_m$ probably contributes to the poorly understood variability in mRNA responses to microRNAs seen in cells (Jonas et al., "Towards a Molecular Understanding of MicroRNA-Mediated Gene Silencing," Nat. Rev. Genet. 16:421-433 (2015), which is hereby incorporated by reference in its entirety).

The effects of $m^6A_m$ contrast with those of $m^6A_m$ While $m^6A_m$ exhibits a stabilizing effect, $m^6A$ is associated with enhanced mRNA degradation (Sommer et al., "The Absolute Frequency of Labeled N-6-Methyladenosine in HeLa Cell Messenger RNA Decreases with Label Time," J. Mol. Biol. 124:487-499 (1978), which is hereby incorporated by reference in its entirety). However, both $m^6A_m$ and $m^6A$ residues in the 5' UTR are linked to increased translation (Meyer et al., "5' UTR m6A Promotes Cap-Independent Translation," Cell 163:999-1010 (2015), which is hereby incorporated by reference in its entirety), suggesting that these different methylated forms of adenosine in the 5' UTR enhance translation initiation. Thus, the location of the modified nucleotide and the specific combination of methyl groups on adenosine residues encode distinct functional consequences on the mRNA.

What is claimed:

1. A method of enhancing the translation ability and stability of an RNA molecule, said method comprising:
providing a cell-free composition comprising an RNA molecule to be translated, wherein the RNA molecule lacks an $N^6,2'$-O-dimethyladenosine ("$m^6A_m$") residue;
introducing an $m^6A_m$ residue at the first 5' nucleotide of the RNA molecule; and
adding an $m^7G$ nucleotide and triphosphate linker to the $m^6A_m$ residue to create a cap structure to enhance translation ability and stability of the RNA molecule relative to the RNA molecule lacking an $m^6A_m$ or a $m^7G$-ppp-$m^6A_m$ at the 5' end of the RNA molecule.

2. The method according to claim 1, wherein the RNA molecule is a synthetic RNA molecule.

3. The method according to claim 2, wherein the RNA molecule comprises one or more of a non-natural ribonucleotide, deoxyribonucleotide, pseudouridine, or other chemical modification that is compatible with translation by ribosomes.

4. The method according to claim 1, wherein the RNA molecule is a naturally-occurring RNA molecule.

5. The method according to claim 1, wherein said introducing and adding is carried out by ligating an RNA molecule comprising an $m^7G$-ppp-$m^6A_m$ structure at the 5' end of the RNA molecule to the RNA molecule to be translated.

6. A method of enhancing the translation ability and stability of an RNA molecule, said method comprising:
providing a cell-free composition comprising an RNA molecule to be translated, wherein the RNA molecule lacks an $m^6A$ residue;
introducing an $m^6A$ residue at the first 5' nucleotide of the RNA molecule;
adding an $m^7G$ nucleotide and triphosphate linker to the $m^6A$ residue to create a cap structure; and
methylating the $m^6A$ residue to form an $m^6A_m$ residue to enhance translation ability and stability of the RNA molecule relative to the RNA molecule lacking an $m^6A_m$ or a $m^7G$-ppp-$m^6A_m$ at the 5' end of the RNA molecule.

7. The method according to claim 6, wherein the RNA molecule is a synthetic RNA molecule.

8. The method according to claim 7, wherein the RNA molecule comprises one or more of a non-natural ribonucleotide, deoxyribonucleotide, pseudouridine, or other chemical modification that is compatible with translation by ribosomes.

9. The method according to claim 6, wherein the RNA molecule is a naturally-occurring RNA molecule.

10. The method according to claim 6, wherein said introducing and adding is carried out by ligating an RNA molecule comprising an $m^7G$-ppp-$m^6A$ structure at the 5' end of the RNA molecule to the RNA molecule to be translated.

11. A method of enhancing the translation and stability of an RNA molecule, said method comprising:

providing an RNA molecule and adding to the RNA molecule a 5' cap structure comprising a 7-methylguanosine ("m$^7$G"), a 5' triphosphate linker ("-ppp-"), and an N$^6$,2'-O-dimethyladenosine ("m$^6$A$_m$").

12. The method according to claim 11, wherein said RNA molecule comprises ribonucleotides, modified nucleotides, deoxynucleotides, or nucleotide mimetics compatible with ribosome-mediated translation.

13. A method of making an RNA molecule, said method comprising:

providing an RNA molecule having a methylated adenosine ("m$^6$A") residue at the first transcribed base of an mRNA molecule and capping the RNA molecule with a m$^7$G cap under conditions effective to convert the m6A residue to an N$^6$,2'-O-dimethyladenosine ("m$^6$A$_m$") residue to make an RNA molecule comprising an m6A$_m$ residue at the first 5' nucleotide of the RNA molecule.

14. A method of making an RNA molecule, said method comprising:

transcribing an RNA molecule in the presence of a primer comprising a methylated adenosine ("m$^6$A") residue at the 5' end of the primer in the presence of primer-dependent RNA polymerase and capping the RNA molecule with a 7mG cap under conditions effective to convert the m$^6$A residue to an N$^6$,2'-O-dimethyladenosine ("m$^6$A$_m$") residue to make an RNA molecule comprising an m$^6$A$_m$ residue in the first 5' nucleotide of the RNA molecule.

15. A method of making an RNA molecule, said method comprising:

transcribing an RNA molecule in the presence of a primer comprising a m$^7$G cap followed by an N$^6$,2'-O-dimethyladenosine ("m$^6$A$_m$") residue at the 5' end of the primer under conditions effective to make an RNA molecule comprising an m6A$_m$ residue in the first 5' nucleotide of the RNA molecule.

16. A method of making an RNA molecule, said method comprising:

providing a reaction solution comprising an mRNA molecule comprising a 5' m$^7$G cap followed by an adenosine residue as the first 5' residue and enzymes capable of 2'-O-methylating and N$^6$-methylating the adenosine residue to make an RNA molecule comprising an m$^6$A$_m$ residue in the first 5' nucleotide of the RNA molecule.

17. A method of making an RNA molecule, said method comprising:

providing an RNA molecule comprising a 5' N$^6$-methyladenosine ("m$^6$A") residue and adding to the RNA molecule a 5' m$^7$G cap.

18. The method according to claim 17, wherein said adding is carried out in the presence of a vaccinia capping enzyme.

19. The method according to claim 18 further comprising:

modifying the RNA molecule by introducing into the RNA molecule a 2'-O-methyl group on the m$^6$A residue to form m$^6$A$_m$.

20. A treatment method comprising:

contacting a cell with an RNA molecule comprising an N$^6$,2'-O-dimethyladenosine ("m6A$_m$") residue at the first 5' nucleotide of the RNA molecule under conditions effective to cause translation of the RNA molecule to treat the cell.

21. A treatment method comprising:

contacting a cell with a DNA molecule encoding an RNA molecule comprising a 5' m$^7$G cap and an N$^6$,2'-O-dimethyladenosine ("m$^6$A$_m$") residue in the first encoded 5' nucleotide of the RNA molecule under conditions effective for the DNA molecule to be transcribed to produce an RNA molecule comprising an m6A$_m$ residue in the first 5' nucleotide of the RNA molecule such that the RNA molecule is translated to treat the cell.

22. A method of synthesizing an RNA molecule, said method comprising:

transcribing a DNA molecule in a cell-free composition to synthesize an RNA molecule comprising a cap structure at the 5' end of the RNA molecule, wherein the cap structure comprises an m$^7$G or m$^7$G-like residue, a phosphate linker, and an m$^6$A$_m$ residue, wherein the phosphate linker links the m$^7$G or m$^7$G-like residue to the m$^6$A$_m$ residue.

23. The method according to claim 22, wherein the cap structure enhances the translation ability of the RNA molecule relative to the RNA molecule lacking the cap structure.

24. The method according to claim 22, wherein the cap structure enhances the stability of the RNA molecule relative to the RNA molecule lacking the cap structure.

25. The method according to claim 22, wherein the cap structure enhances the translation ability and stability of the RNA molecule relative to the RNA molecule lacking the cap structure.

26. The method according to claim 22, wherein the phosphate linker comprises 3 phosphates.

* * * * *

UNITED STATES PATENT AND TRADEMARK OFFICE
CERTIFICATE OF CORRECTION

PATENT NO. : 10,907,165 B2
APPLICATION NO. : 16/345786
DATED : February 2, 2021
INVENTOR(S) : Jaffrey et al.

Page 1 of 1

It is certified that error appears in the above-identified patent and that said Letters Patent is hereby corrected as shown below:

In the Claims

Claim 13 at Column 59, Line 18, delete "m6A" and insert --$m^6A$--

Claim 13 at Column 59, Line 20, delete "m6A$_m$" and insert --$m^6A_m$--

Claim 14 at Column 59, Line 28, delete "7mG" and insert --$m^7G$--

Claim 15 at Column 39, Line 39, delete "m6A$_m$" and insert --$m^6A_m$--

Claim 20 at Column 60, Line 14, delete "m6A$_m$" and insert --$m^6A_m$--

Claim 21 at Column 60, Line 25, delete "m6A$_m$" and insert --$m^6A_m$--

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*